(12) United States Patent
Anwar et al.

(10) Patent No.: US 11,576,580 B2
(45) Date of Patent: Feb. 14, 2023

(54) APPARATUS, SYSTEMS AND METHODS FOR INTRAOPERATIVE IMAGING

(71) Applicant: The Regents of the University of California, Oakland, CA (US)

(72) Inventors: Moshiur M. Anwar, San Francisco, CA (US); Catherine Park, San Francisco, CA (US); Bernard Boser, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 210 days.

(21) Appl. No.: 16/854,463

(22) Filed: Apr. 21, 2020

(65) Prior Publication Data
US 2020/0383576 A1 Dec. 10, 2020

Related U.S. Application Data

(63) Continuation of application No. 15/687,205, filed on Aug. 25, 2017, now Pat. No. 10,772,504, which is a continuation-in-part of application No. 15/074,614, filed on Mar. 18, 2016, now Pat. No. 9,820,653.

(51) Int. Cl.
*A61B 5/00* (2006.01)
*A61K 49/00* (2006.01)

(52) U.S. Cl.
CPC .......... *A61B 5/0071* (2013.01); *A61B 5/0084* (2013.01); *A61B 5/0091* (2013.01); *A61B 5/4836* (2013.01); *A61K 49/0032* (2013.01); *A61K 49/0058* (2013.01); *A61K 49/0067* (2013.01); *A61B 5/4381* (2013.01)

(58) Field of Classification Search
CPC A61B 5/0071; A61B 5/0084; A61K 49/0032; A61K 49/0058
See application file for complete search history.

(56) References Cited

U.S. PATENT DOCUMENTS

| | | | |
|---|---|---|---|
| 5,590,660 | A | 1/1997 | MacAulay |
| 5,716,595 | A | 2/1998 | Goldenberg |
| 6,485,413 | B1 | 11/2002 | Boppart et al. |
| 8,574,859 | B2 | 11/2013 | Lin |
| 9,304,280 | B2 | 4/2016 | Gular |
| 9,314,304 | B2 | 4/2016 | Lee |
| 2003/0138378 | A1 | 7/2003 | Hashimshony |
| 2003/0222325 | A1 | 12/2003 | Jacobson |
| 2006/0165350 | A1 | 7/2006 | Gelikonov |
| 2011/0009702 | A1 | 1/2011 | Morishita et al. |
| 2011/0059016 | A1 | 3/2011 | Ramanujam et al. |
| 2012/0224053 | A1 | 9/2012 | Vykoukal |
| 2012/0327248 | A1 | 12/2012 | Tack |
| 2014/0303452 | A1 | 10/2014 | Ghaffari |

FOREIGN PATENT DOCUMENTS

WO 2008119493 A1 10/2008

*Primary Examiner* — Rex R Holmes
(74) *Attorney, Agent, or Firm* — Sean Solberg

(57) ABSTRACT

The disclosed apparatus, systems and methods relate to devices, systems and methods for intra-operative imaging.

19 Claims, 46 Drawing Sheets

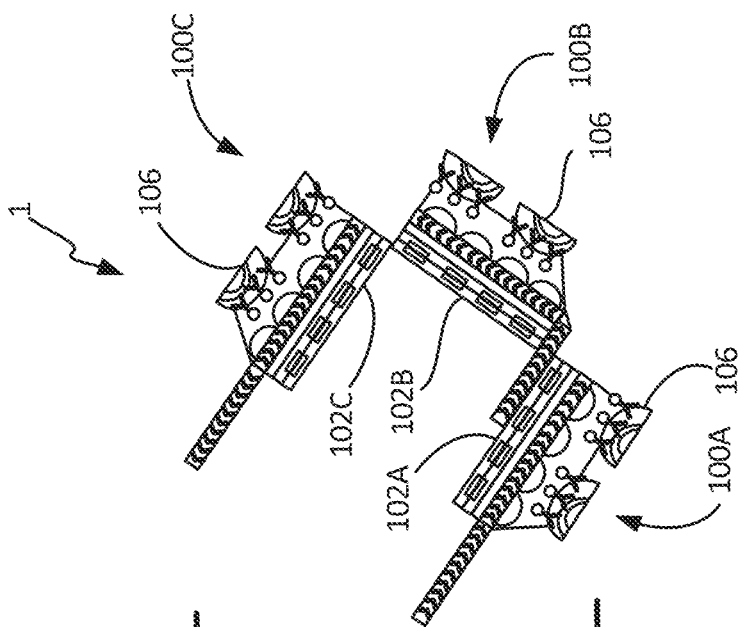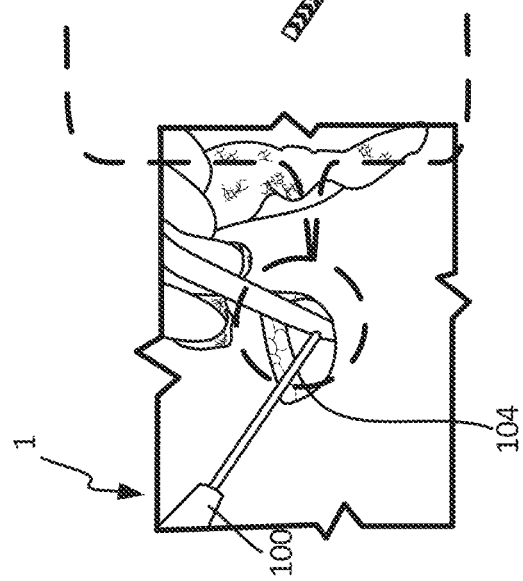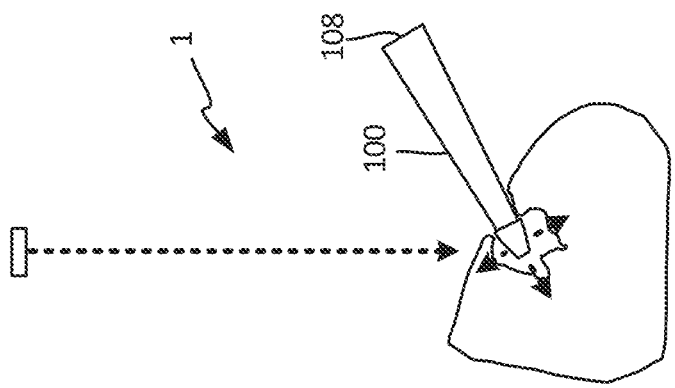

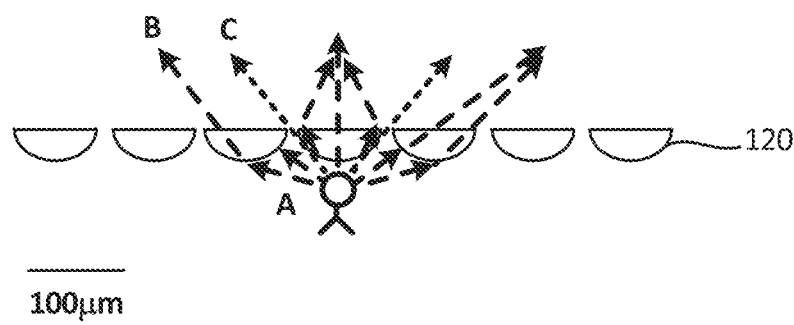
Fig. 3A
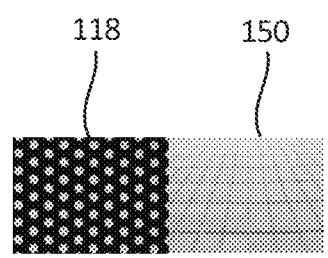
Microfabricated Stencil | Wafer of Stencils
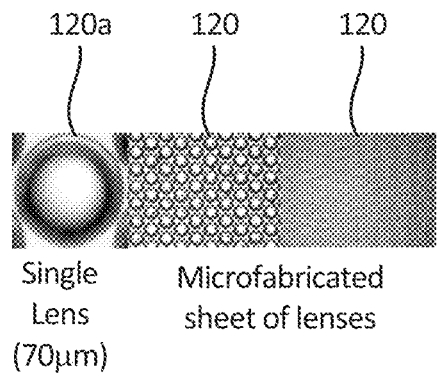
Fig. 3B
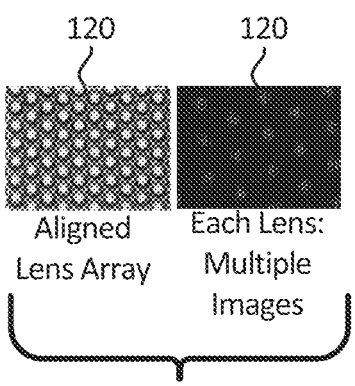
Aligned Lens Array | Each Lens: Multiple Images
Fig. 3C

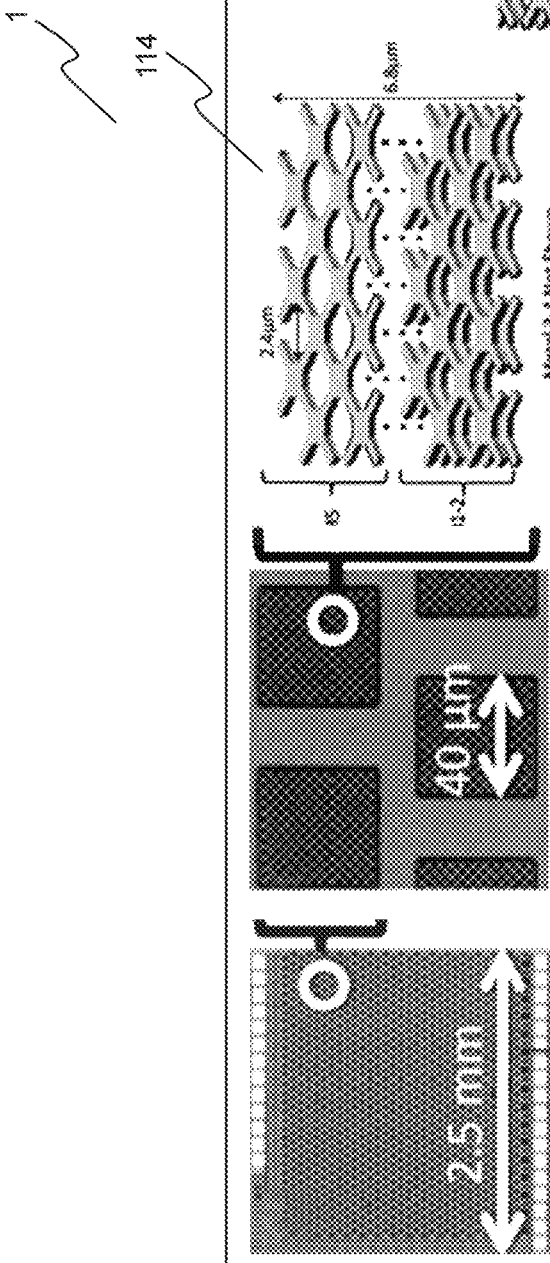
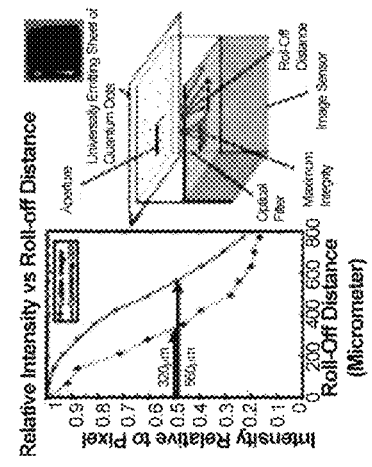
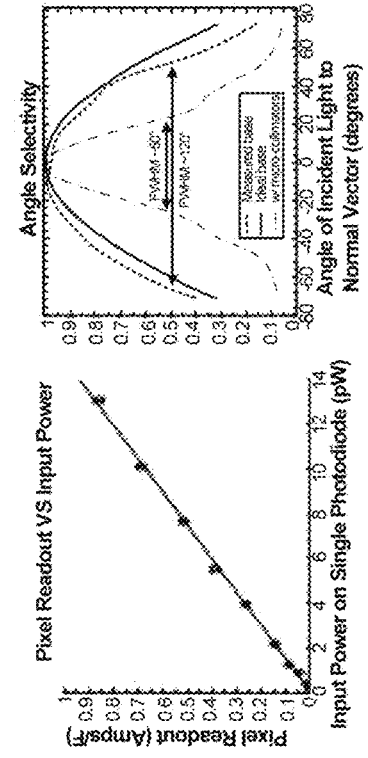
FIG. 6A  FIG. 6B  FIG. 6C  FIG. 6D  FIG. 6E  FIG. 6F  FIG. 6G

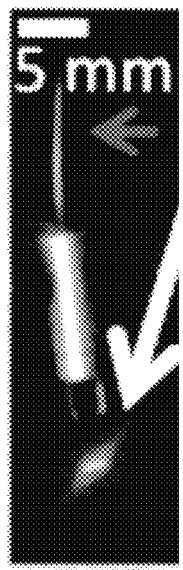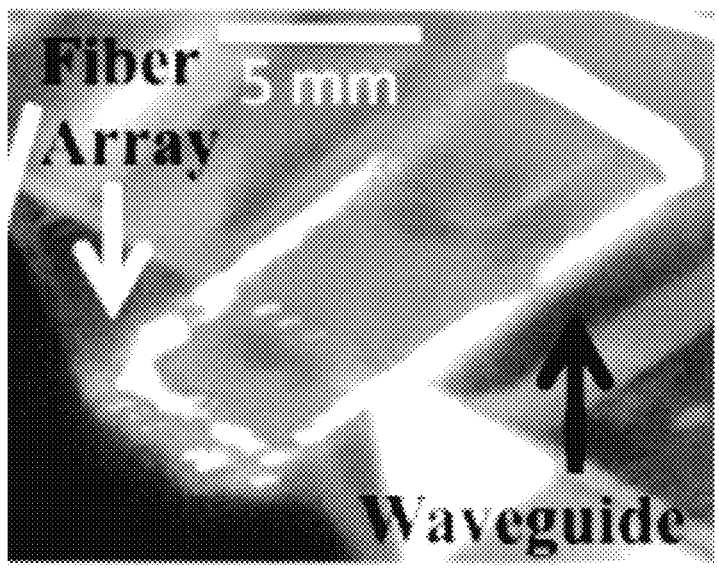
FIG. 11A    FIG. 11B
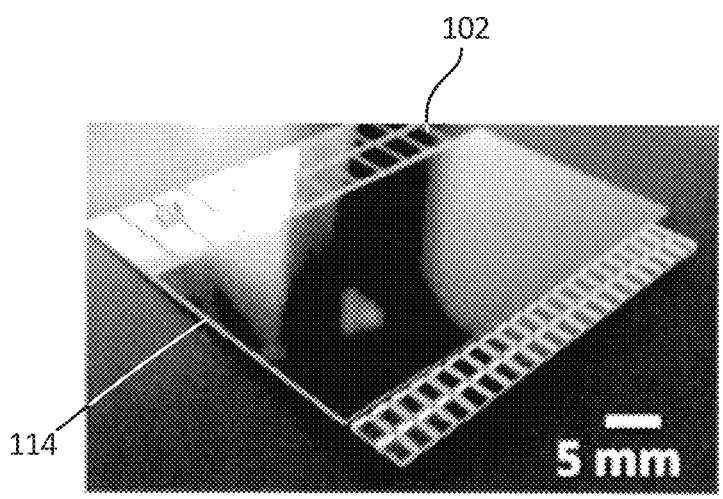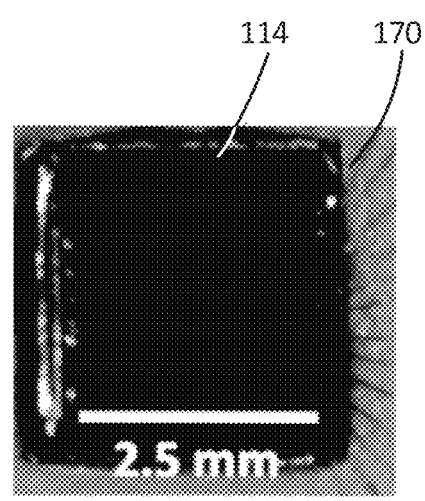
FIG. 12A    FIG. 12B

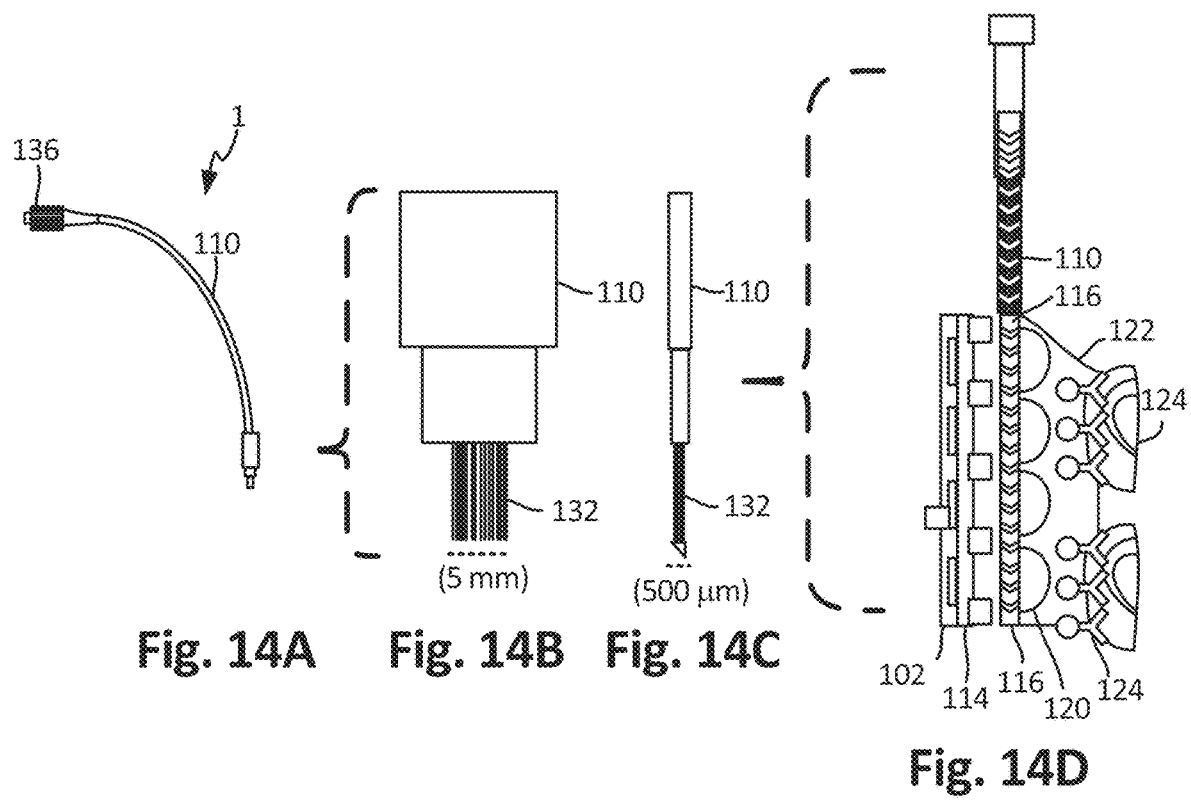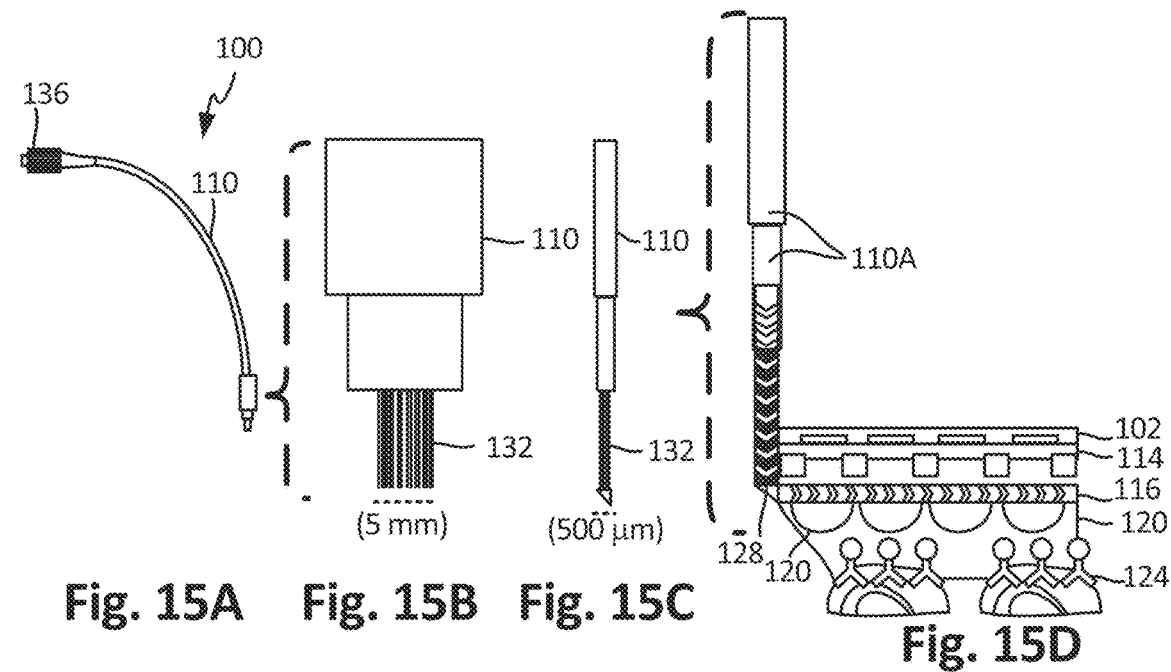

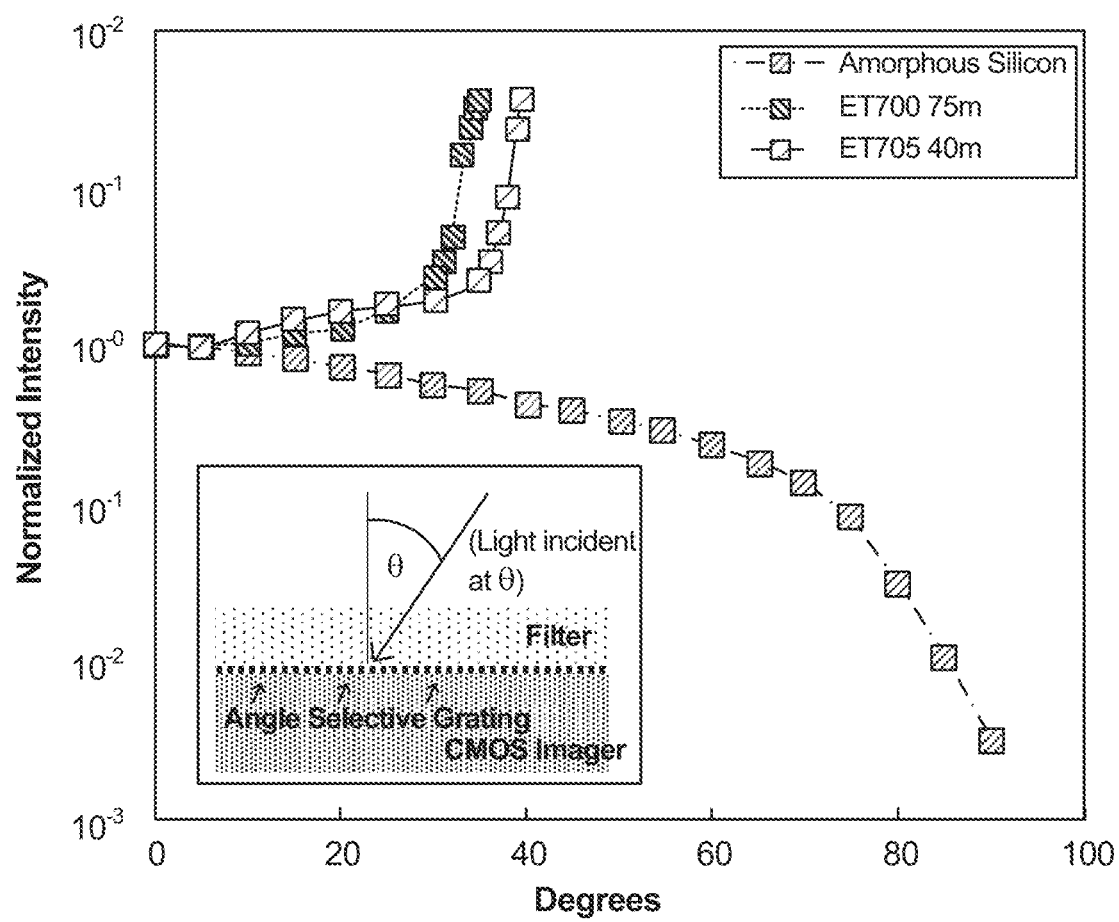
Fig. 19
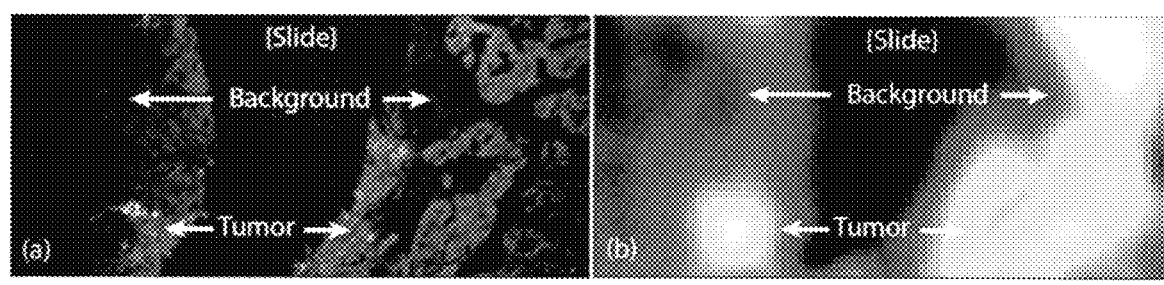
Fig. 20A                    Fig. 20B

| Previous | Current |
|---|---|
| 300 μm | 50-100 μm |
| <1 μm | <1 μm |
| 10 μm | 10-15 μm |
| 500 μm | 100 μm |
FIG. 24A
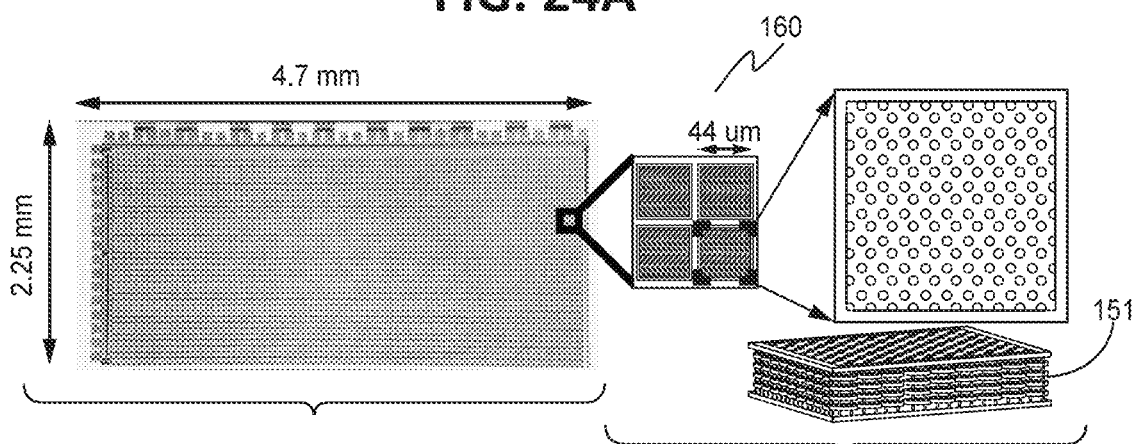
FIG. 24B
FIG. 24C
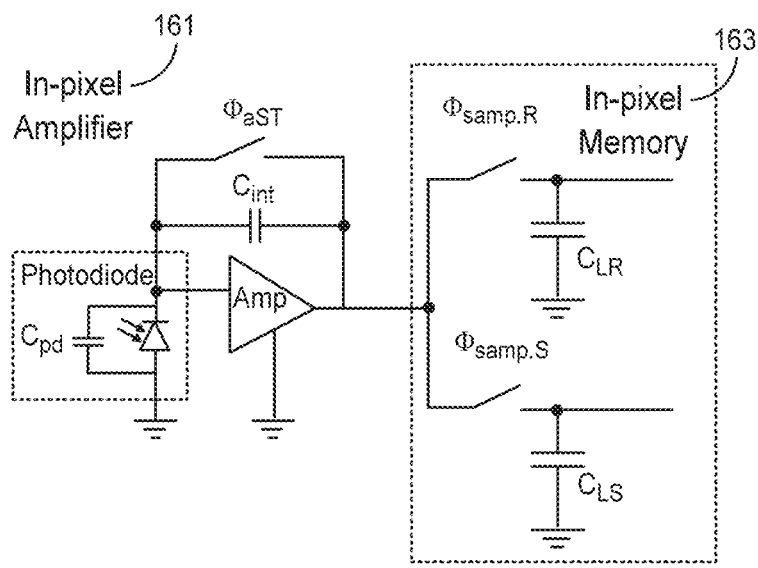
FIG. 24D

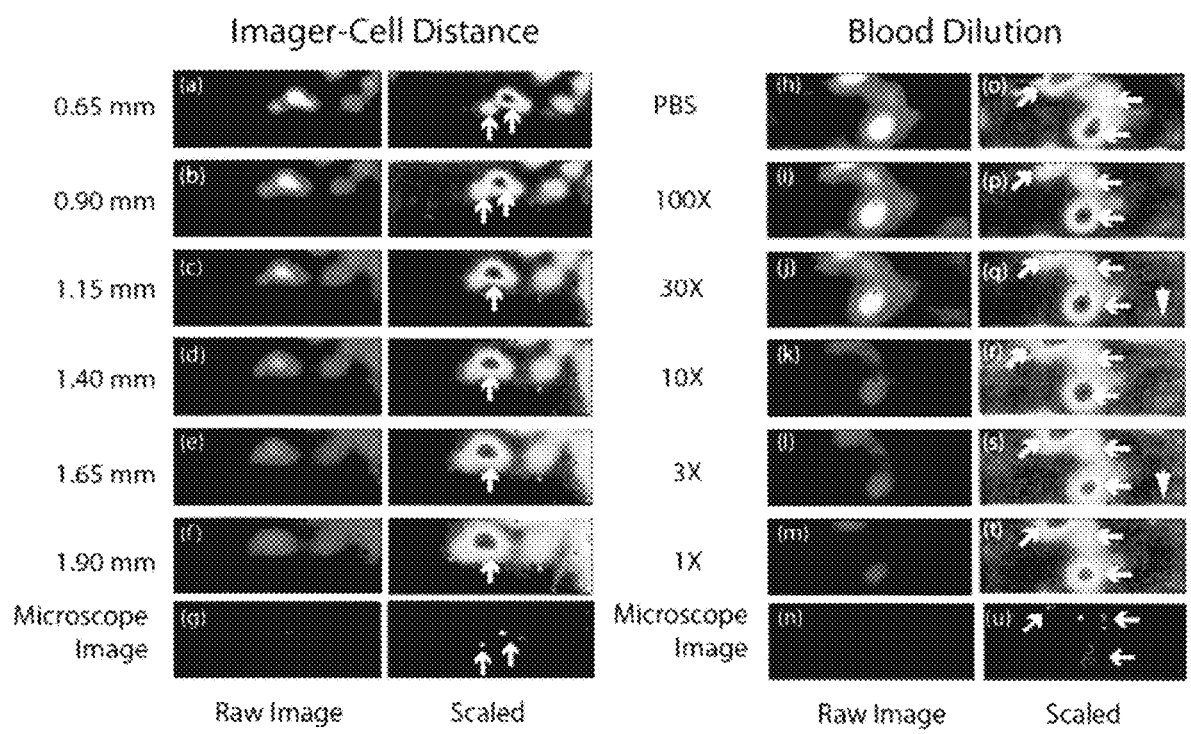
Fig. 30A
Fig. 30B
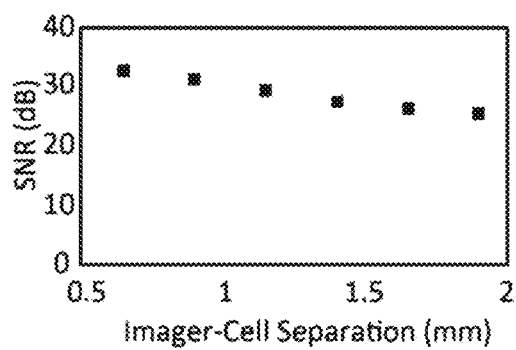
Fig. 30C
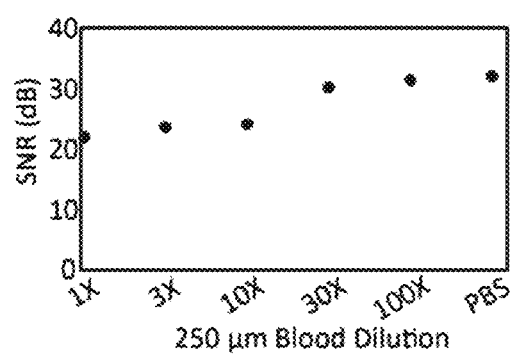
Fig. 30D

APPARATUS, SYSTEMS AND METHODS FOR INTRAOPERATIVE IMAGING

CROSS-REFERENCE TO RELATED APPLICATION(S)

This application is a continuation of U.S. application Ser. No. 15/687,205, filed Aug. 25, 2017 and entitled "Apparatus, Systems and Methods for Intraoperative Imaging," which is a continuation-in-part of U.S. application Ser. No. 15/074,614, filed Mar. 18, 2016, now U.S. Pat. No. 9,820,653 issued Nov. 21, 2017 and entitled "Methods, Systems, And Devices For Imaging Microscopic Tumors," which is a continuation of International PCT Patent Application No. PCT/US14/56788, filed on Sep. 22, 2014, and U.S. Provisional Application 61/880,750, filed Sep. 20, 2013, and entitled "Methods, Systems, And Devices For Imaging Microscopic Tumors," all of which are hereby incorporated herein in their entireties by this reference. This application also claims priority to U.S. Provisional Application No. 62/379,416 filed Aug. 25, 2016 and entitled "Apparatus, Systems and Methods for Intraoperative Imaging" which is hereby incorporated by reference in its entirety under 35 U.S.C. § 119(e).

GOVERNMENT SUPPORT

This invention was made with government support under grant no. TR000004 awarded by the National Institutes of Health. The government has certain rights in the invention.

TECHNICAL FIELD

The disclosed technology relates generally to surgical devices and techniques, and in particular, to the devices, methods, and design principles for an intra-operative imaging system for visualizing microscopic disease. This has implications in the minimally disruptive treatment of a variety of diseases.

BACKGROUND

The disclosure relates to apparatus, systems and methods for an intra-operative imaging system for visualizing microscopic disease.

Successful treatment of early stage cancer, such as prostate and breast cancer, depends on completely resecting all disease, both gross and microscopic, while sparing healthy tissue. Unfortunately, because microscopic disease is challenging to visualize intraoperatively, yet cancer cells are all too often left behind, significantly increasing the chance of cancer returning across disease sites. Consequently, the surgeon is faced with a difficult clinical decision: remove an additional margin of healthy appearing tissue, risking additional morbidity or risk leaving microscopic disease behind. Microscopic residual disease ("MRD") leads to increased local recurrence ("LR") and, potentially, reduced overall survival ("OS"). Therefore patients are often subjected to additional treatment (such as re-resection, radiation, and/or chemotherapy) to reduce the chance of recurrence; a result that could have been avoided if the entire tumor was initially removed. Although crude methods exist to evaluate tumor in the operating room, definitive identification of MRD can only be determined days later after molecular staining and microscopic visualization of the excised specimen in a pathology laboratory, rendering it ineffective for intraoperative guidance. Similarly microscopic lymph node involvement (mLNI) often goes undetected, and detecting mLNI intraoperatively is of significant importance. Therefore this imager covers both imaging on the tissue surface and several (1-10) millimeters below the surface.

Identification of MRD is a prime concern in almost every oncological case. The device presented here is meant to be a platform imager for use with any disease subsite where surgical resection is necessary for cure, and for which there is a targeted agent capable of labeling and identifying the cancer cell. One example is breast cancer, whereby microscopic tumor is left in the tumor bed in one out of four operations. Microscopic residual disease doubles the rate of recurrence and thereby decreases overall survival. Therefore a repeat operation is essential. This could have avoided if all disease was resected during the initial operation. Another example is in prostate cancer, where a positive margin (another term for microscopic residual disease) increases the chance of cancer recurrence. Due to the morbidity of reoperation, patients with MRD are often advised to receive post-operative radiotherapy, lasting approximately 6 weeks with significant cost and additional side effects. Therefore, there is a need to intraoperatively identify MRD within the tumor bed to guide complete resection in a single surgery preventing both the morbidity and cost associated with multiple therapeutic procedures.

To maintain excellent oncologic outcomes across cancer types, while reducing the need for additional post-operative therapy, intraoperative assessment of MRD and mLNI in real-time with precise localization is critically needed. Thus, there is a need in the art for improved intra-operative resection devices, systems and methods.

BRIEF SUMMARY

An intraoperative imager whereby the imaging device is placed within the tumor bed, and onto the tissue surface. This is a fundamental distinction between other devices that actually convert the optical photons to an electronic signal away from the tumor bed, either by imaging over a long distance or using a fiber optic.

The imaging system consists of a photosensitive array of optical detectors, a method of illuminating the tissue surface, a method of removing (filtering) the illumination (excitation light) and a method of enhancing spatial resolution of the light detected. The resulting image is processed to identify tumor cells.

Illumination is achieved by guiding light into the tumor cavity and illuminating the tissue surface directly opposing the intraoperative imager. This also includes a system whereby the tissue surface is illuminated in a series of changing patterns, and using the image from each pattern combined with a known measured point spread function from each, deconvolved to obtain a high-resolution image.

A system whereby an optical tag coupled to a targeted molecular agent is used to label cancer cells. This optical tag may be an organic fluorophore (examples include, but are not limited to indocyanine green) or an inorganic particle with optical properties, such as an up-converting nanoparticle discussed herein. A system whereby long fluorescent or luminescent lifetimes of an optical tag to the targeted molecular agent are used for time gated imaging.

In certain implementations of this system an optical filter is used to remove background (illumination) light. In certain implementations, this filter consists of an multilayer optical filter. In alternate implementations, a simpler optical filter can be used, such as a long, short or band pass filter. In alternate implementations, a filter is comprised of a material that absorbs light at the wavelength of the excitation (illumination) light and allows fluorescently emitted light to pass through to the imager.

In certain implementations of this system, the optical filter is not used, further thinning the device.

An imaging chip wherein a global shutter is used, enabling time-gated imaging (whereby the excitation light is modulated on and off, and the image is gathered while the excitation light is off).

The above imaging platform using a set of rapidly alternating wavelengths of light to enable imaging (and subtraction) of the background (dark current, offset, auto-fluorescence) by exciting with a wavelength slightly offset (for example 50-500 nm from the peak of the optical tag absorption), measuring the background, and then illuminating with the correct wavelength to image both the background plus the fluorescent signal. The two signals will then be subtracted to obtain the image. In certain implementations, the offset is about 100 nm.

An imaging chip whereby each pixel has integrated background subtraction. A comparator can also be integrated, giving a digital output (greater than or less than) comparing two sequential images. The imager would take and store a background image representing fluorescent and autofluorescent background, dark current, noise, and any pixel-level offset (imaging either with zero light or with light at a wavelength different from the excitation wavelength), and subsequently take an image using the excitation light. The two images can be subtracted at the pixel level, or off chip, as discussed above. This background subtraction can also incorporate illumination calibration to eliminate non-uniformity in the excitation light: a baseline image is taken with the input or excitation light equal in wavelength to the fluorescently emitted light, thereby passing directly through the optical filter and directly illuminating the sensor, allowing an image corresponding to the illumination to be stored. Subsequent fluorescent images (acquired with the illumination light at the fluorophore excitation wavelength) can be scaled by this amount.

A system whereby organic or inorganic fluorophore absorbs light in the infrared range (>1100 nm), and re-emit in the near infrared, visible or ultraviolet range (<1100 nm). In this implementation, the sample (cells, tissue, etc.) surface is illuminated through the image sensor (as infrared light can pass through silicon), but the re-emitted light at a lower wavelength is captured by the photodiode. Time gated imaging is also incorporated here such that the image is gathered after the excitation light is turned off reducing background. An example particle is the upconverting nanoparticle (UCNP). Like organic fluorophores UCNPs can be conjugated to a targeted molecular agent, such as antibodies that bind to cancer cells.

A system whereby the planar imager is thin enough to be directly embedded within surgical instrumentation or affixed to a probe without significantly altering the form-factor of the instrument to label cancer cells.

An imaging chip which is thin enough to be flexible, and mounted over a curved surface, such as on a probe or surgical instrument.

An imaging chip whereby upon identification of an area of tumor, a focal therapy is applied. This may consist of (but not limited to), chemotherapy or biologic administration, focally ablating with heat, radiofrequency ablation, ultrasound, radiation, increased light intensity combined with a fluorophore that exhibits toxicity effects when illuminated with a high intensity, known as photoimmunotherapy.

An imaging chip whereby upon identification of an area of tumor the location is relayed of another instrument providing focal therapy. Examples include intraoperative radiation therapy, radiofrequency ablation, ultrasound or heat.

An imaging chip whereby angle selective imaging is implemented by fabricating an array of collimators over the surface of the photodiode.

While multiple embodiments are disclosed, still other embodiments of the disclosure will become apparent to those skilled in the art from the following detailed description, which shows and describes illustrative embodiments of the disclosed apparatus, systems and methods. As will be realized, the disclosed apparatus, systems and methods are capable of modifications in various obvious aspects, all without departing from the spirit and scope of the disclosure. Accordingly, the drawings and detailed description are to be regarded as illustrative in nature and not restrictive.

BRIEF DESCRIPTION OF THE DRAWINGS

The following drawings form part of the present specification and are included to further demonstrate certain aspects of the present invention. The invention may be better understood by reference to one or more of these drawings in combination with the description of specific embodiments presented herein.

FIG. 2A depicts a schematic overview of certain exemplary embodiments of the imager as applied to a patient's body cavity.

FIG. 2B depicts one embodiment of the imager inserted into a body cavity of a patient.

FIG. 2C depicts a cross-section of the embodiment of FIG. 2B, showing the multiple imagers possible.

FIG. 3A depicts a side view of the waveguide and microlens array, according to an exemplary embodiment.

FIG. 3B depicts an angle of refraction, according to an exemplary embodiment.

FIG. 3C depicts various angles of refraction, according to certain embodiments.

FIG. 6A depicts a die photo of an imager, according to an exemplary embodiment.

FIG. 6B depicts a zoomed view of a 40 micrometer pixel with microcollimators, according to an exemplary embodiment.

FIG. 6C depicts a perspective view of stacked microcollimators, according to an exemplary embodiment.

FIG. 6D depicts angle selectivity to a laser illustrating sharp reduction at angles about 15 degrees, according to one embodiment.

FIG. 6E depicts the sensitivity compared with optical power input, according to one embodiment.

FIG. 6F depicts the impact of microcollimators on blur reduction, according to one embodiment.

FIG. 6G depicts the blur reduction of a fluorescent spot or quantum dots, showing a sharper image edge, according to one implementation.

FIG. 11A depicts a close-up photograph of an optical fiber that terminates into a linear array of fibers.

FIG. 11B is a close-up view of a quartz waveguide that can be coupled to the fibers of FIG. 11A in certain implementations.

FIG. 12A depicts a perspective view of a fused silica wafer coated with an optical interference filter, according to one implementation.

FIG. 12B is a top view of a CMOS imager with the interference filter epoxied to the surface.

FIG. 14A depicts a side view of a light guide having a multi-fiber core, according to one implementation.

FIG. 14B is a close-up front view of the core of FIG. 14A.

FIG. 14C is a wider angle view of the core of FIG. 14B.

FIG. 14D is a detailed close up view of the implementation of FIG. 14C.

FIG. 15A depicts a side view of a light guide having a multi-fiber core, according to one implementation.

FIG. 15B is a close-up front view of the core of FIG. 15A.

FIG. 15C is a wider angle view of the core of FIG. 15B.

FIG. 15D is a side view of the imaging system having the light guide of FIG. 15A in a perpendicular orientation.

In FIG. 19 is a plot of normalized intensity as a function of incident angle (degrees) using 633 nm light, according to several embodiments.

FIG. 20A is a fluorescence image of a human breast tissue sample mounted on a glass slide stained with anti-HER2 antibody and a quantum-dot (705 nm) secondary antibody, taken at 5 s integration.

FIG. 20B is the same image as FIG. 20A, taken with a 15 um aSi filter 114 attached.

FIG. 24A is a table showing the improvements in size in current implementations as opposed to previous iterations.

FIG. 24B depicts a top view of the angle-selective grating of a single pixel, consisting of a 20×20 octagonally-packed array of 2.4 μm wide by 6.8 μm tall tube-like structures.

FIG. 24C depicts further views of the angle-selective grating of FIG. 24B.

FIG. 24D depicts schematic of an in-pixel amplifier and in-pixel memory, according to one implementation.

FIG. 30A depicts raw and scaled images of cells in culture taken at a variety of imager distances and a microscope taken image.

FIG. 30B depicts raw and scaled images taken at a variety of dilutions of a relatively thick, highly scattering and nearly opaque 250 μm layer of blood.

FIG. 30C plots the SNR over imager-cell separation shown in FIG. 30A.

FIG. 30D plots the SNR over blood dilution shown in FIG. 30B.

DETAILED DESCRIPTION

Figure 1A:
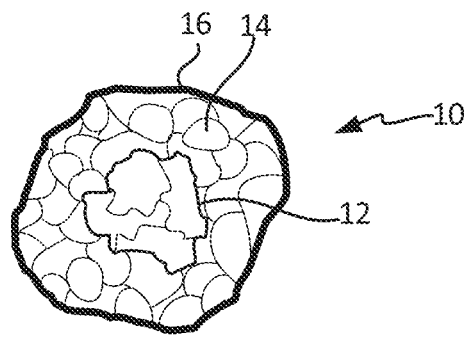
FIG. 1A depicts a cross-sectional overview of diseased tissue.

The various systems and devices disclosed herein relate to devices for use in medical procedures. More specifically, various embodiments relate to imaging devices, systems and methods for visualizing microscopic residual disease ("MRD") and microscopic lymph node involvement ("mLNI") in an intraoperative environment. Certain exemplary implementations relate to imaging systems, devices, and methods for visualizing microscopic breast and prostate cancer. It is understood that the various embodiments of the system and related methods disclosed herein can be incorporated into or used with any other known medical devices, systems and methods, including those disclosed in co-pending U.S. application Ser. No. 15/074,614, incorporated above, Efthymios P. Papageorgiou; Bernhard E. Boser; Mekhail Anwar, "An angle-selective CMOS imager with on-chip micro-collimators for blur reduction in near-field cell imaging," 2016 IEEE 29th International Conference on Micro Electro Mechanical Systems (MEMS), p. 337-340, Efthymios P. Papageorgiou; Bernhard E. Boser; Mekhail Anwar, "Chip-scale fluorescence imager for in vivo microscopic cancer detection," 2017 Symposium on VLSI Circuits, 2017, p. C106-C107, all of which are incorporated by reference in their entirety. While the system is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

The various embodiments disclosed or contemplated herein relate to an improved intra-operative imaging system for visualizing microscopic disease. In exemplary embodiments, the system has an imager device for imaging biological material in a patient. In various implementations, a fluorescently conjugated molecule, such as an organic molecule, inorganic fluorescent particle, or luminescent molecule) capable of binding to the biological material is administered to the patient. In various implementations, a visualization system in electrical communication with the imager is provided, such that emitted fluorescence is received by the imager for display by way of the visualization system.

The various implementations of the system present numerous advantages over the prior art. When performing a resection with current technologies, a surgeon is left with a difficult decision: first, to remove more healthy tissue, which can result in poor functional and cosmetic outcomes, such as has historically been done with mastectomy in the case of breast cancer or second, to excise only the suspected tumor (for example with lumpectomy in breast cancer), but risk a greater chance of cancer returning because the practitioner missed removing microscopic disease. As examples, in breast cancer 1 in 4 women has disease left behind, doubling the local recurrence rate in these women, and leading to a decrease in overall survival. Therefore another operation to re-excise the residual cancer cells is required. Similarly in prostate cancer, in up 10-50% of men, tissue can be left behind, but due to the morbidity of re-excision in the prostate bed, these patients must be treated with post-operative radiation, adding significant cost and toxicity to the treatment. As is shown in FIG. 2A, the tissue area 10 comprises a cancerous (gross disease) area 12 surrounded by healthy tissue 14, which may contain some microscopic traces of disease tissue, and an edge 16, wherein the tissue ceases to contain any traces of disease tissue. This makes identifying and resecting microscopic disease vital. There is significant difficulty in identifying cancerous cells during the removal of a tumor, because isolated foci of tumor cells cannot be seen with current intraoperative imaging tools or felt.

Figures 1B, 1C:
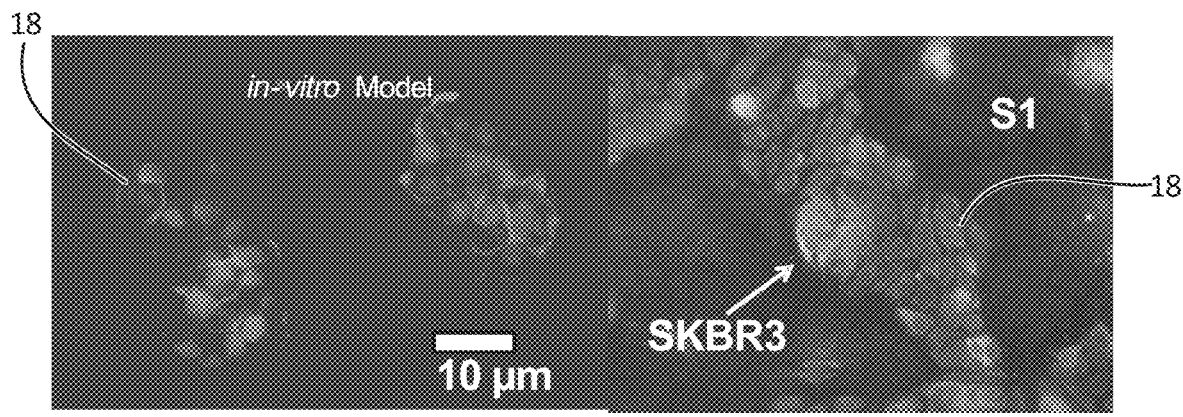
FIG. 1B depicts a field of cells fluoresced by way of a secondary label.
FIG. 1C depicts a field of cells fluoresced by way of a primary conjugated antibody.

The configuration of the system presented here offers numerous advantages over the prior art enabling visualization of microscopic disease. The approach presented here utilizes a fluorescently-tagged molecule that is pre-operatively injected and binds to the tumor within the patient's body. Other embodiments can include injection into the tumor bed or local injection into the tumor tissue area preoperatively. FIGS. 1B-C depict the comparative ease of in vitro identification when using labeling.

Figure 29:
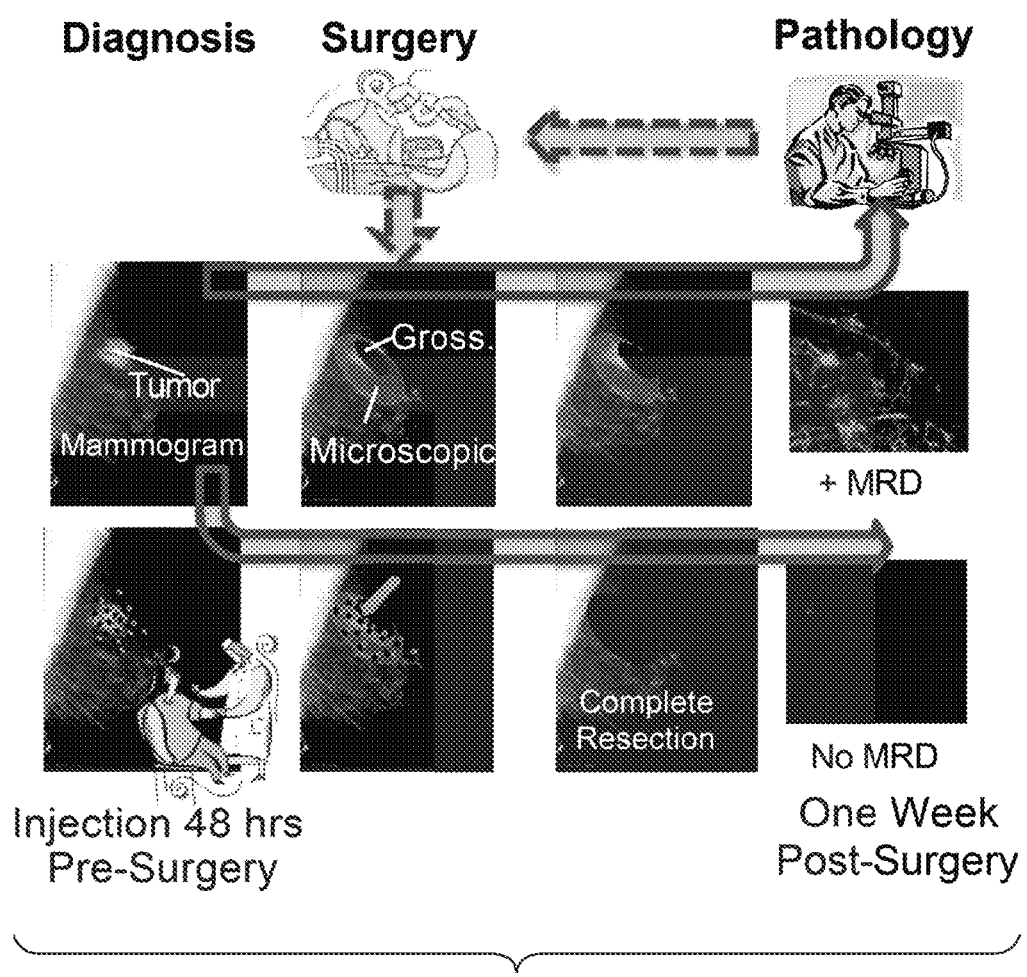
FIG. 29 is a schematic overview with images showing the progression of surgical detection and resection, according to one implementation.

It is understood that transforming the surgical resection tool itself into a microscopic fluorescent imager by coating or embedding the surface with a sub-millimeter thin, planar fluorescent imaging array offers numerous advantages. These various implementations can thin the imager 102 itself down to 10-50 um. It is understood that in certain of these implementations, the imager 102 can be flexible so it can be placed on a curved surface. Exemplary implementations of the system 1 improve in vivo molecular labels of microscopic residual disease in breast cancer. Similar to the methods previously described herein, labeling tumor cells in vivo using a targeted molecular agent is the first step in translating the procedures from the pathology laboratory into the real-time operating room environment. Systemically injecting labeled antibody to identify cancer in vivo is a well-established technique in both animal models and human clinical trials. Using a well-studied strategy of systemically injecting fluorescently-labeled Trastuzumab, a humanized antibody to the HER2 receptor, to label HER2-overexpressing breast cancer cells in vivo, it is possible to establish the optimal dose and timing of the fluorophore-Trastuzumab conjugate injection, quantifying both specific and non-specific binding for use in imager design. This fluorophore can be organic or inorganic, and include optical tags with long-fluorescent or luminescent lifetimes. The overall concept is illustrated in FIG. 29 with breast cancer as an example system. Various biologics, and pre-operative injection times are also contemplated.

Figure 2D:
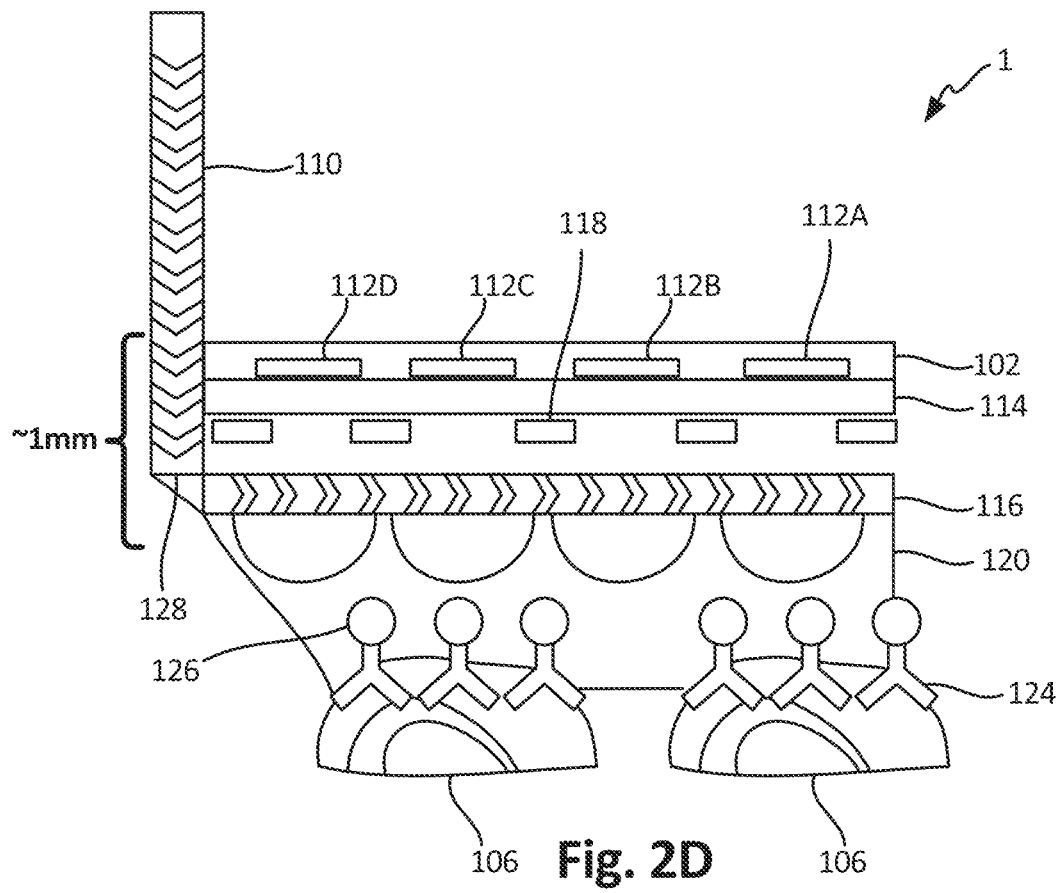
FIG. 2D depicts a detailed schematic overview of the imaging system, according to an exemplary embodiment.
Figure 4:
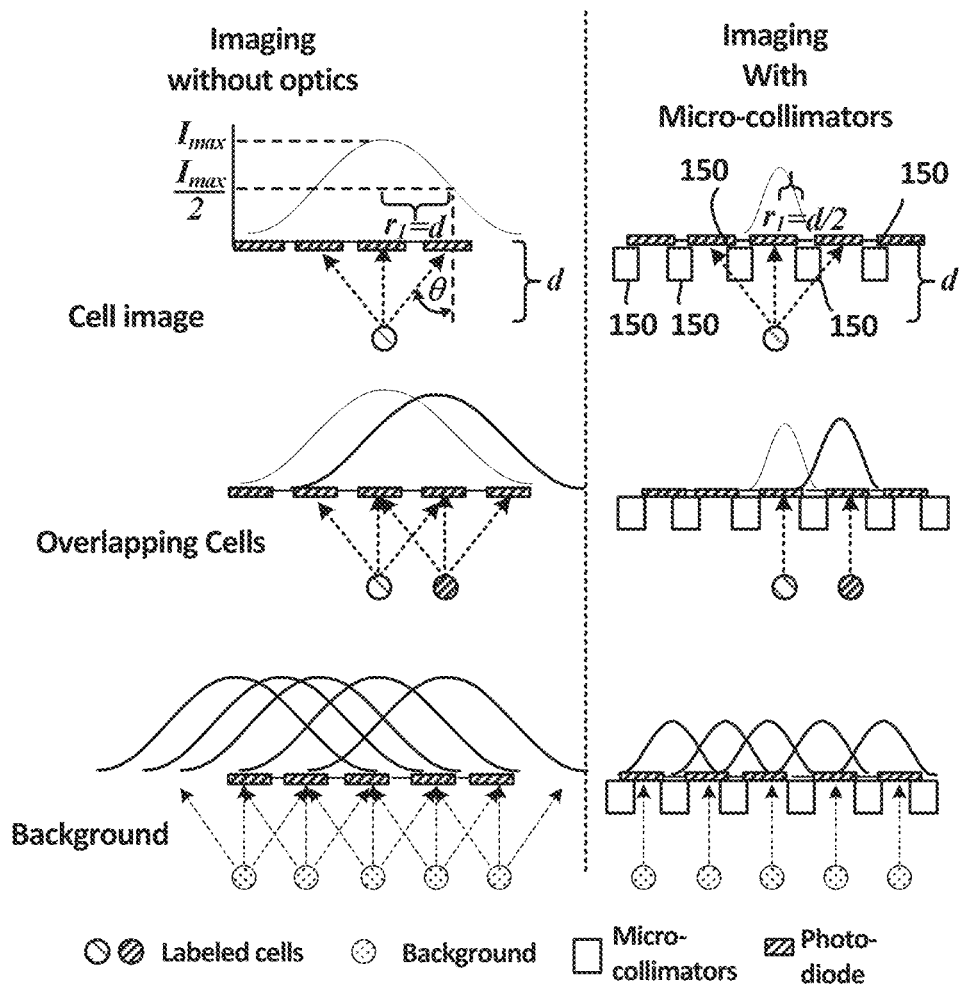
FIG. 4 depicts several angles of light traveling through the microlens array, according to certain embodiments.
Figure 5A:
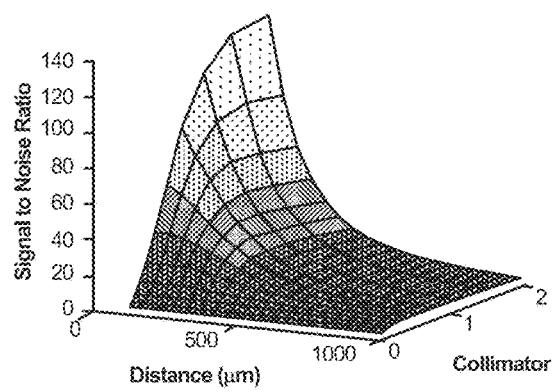
FIG. 5A depicts a 3D graphical rendering of the signal to noise ratio, according to certain implementations.
Figure 5B:
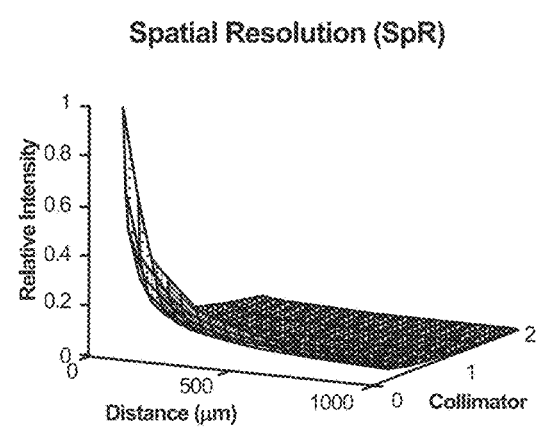
FIG. 5B depicts a 3D graphical rendering of the spatial resolution, according to certain implementations.
Figure 5C:
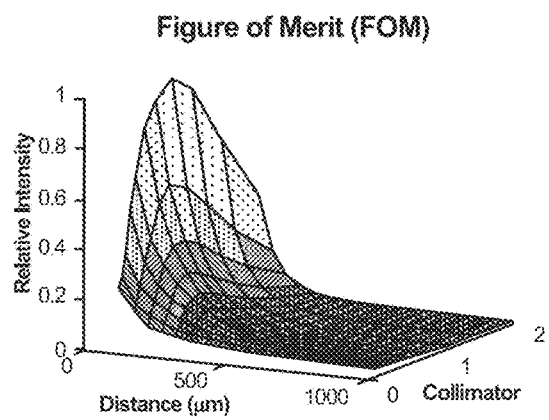
FIG. 5C depicts a 3D graphical rendering of the figure of merit, according to certain implementations.
Figure 5D:
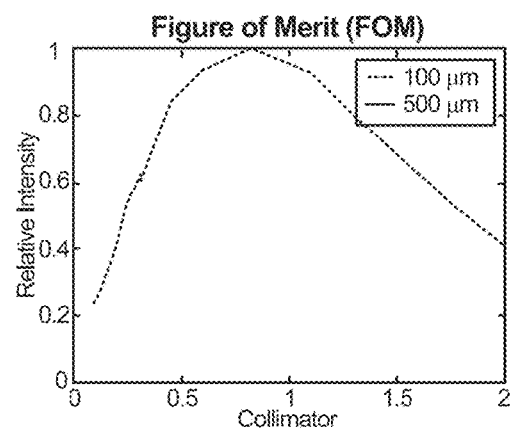
FIG. 5D depicts a graphical rendering of the figure of merit, according to certain implementations.
Figure 7:
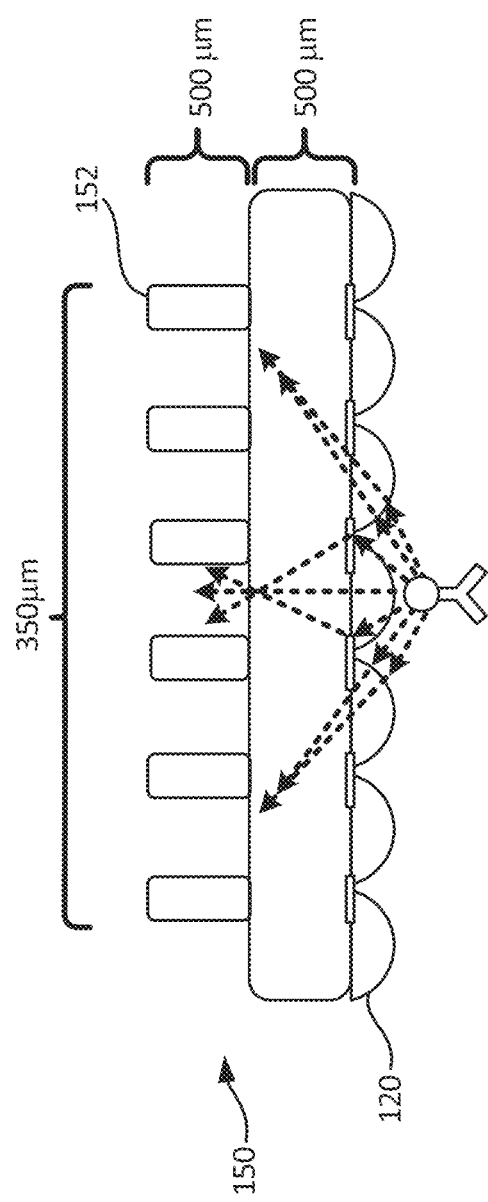
FIG. 7 depicts light angles relative to a microlens, according to one implementation.

In various embodiments of the system, compatable optical labels, such as primary and/or secondary fluorescent antibodies targeting any number of disease tissues may be used with quantum dots. In these implementations, quantum dots are fluorescent nano-particles that do not bleach, and can be illuminated at any wavelength less than 700 nm, and still emit at 700 nm, making them extremely robust fluorophores. Other inorganic fluorophores can also be used, including up-converting nanoparticles. As quantum dots are not yet FDA approved, and to avoid the need for secondary labeling in an in vivo/clinical setting, in the present Example Alexa 647 was conjugated directly to an anti-Her2 antibody, as would be apparent to one of skill in the art. The single anti-Her2 antibody labeling 22 is depicted in FIG. 2D and FIG. 4. While this example of the implementation of the system is illustrated in breast cancer, use of the system can be extended to any other cancer where complete surgical excision is necessary for a cure, such as prostate or pancreatic cancer.

In FIG. 1B, SKBR3 (HER2 overexpressing breast cancer cells) were grown on a bed of S1 (healthy) cells, and labeled with primary anti-Her2 and a secondary antibody (In FIGS. 2B-2C, labeled cells signified with reference number 18). In FIG. 1C, SKBR3 cells are identified using an anti-Her2 antibody conjugated to Alexa 647. Any fluorophore can be used, although those in the near-infrared range have better tissue penetration and are therefore preferable. By way of example, fluorescein, LICOR's IRDye 800CW dye and indocyan green, can be used. Further embodiments include conjugation of the molecularly targeted agent (such as anti-Her2 antibody) to fluorophores.

The systems and devices disclosed herein are configured to be used in combination with labeling of target diseased cells similar to that described in FIGS. 1B-C. Cancer cells are identified by targeted biomolecules—examples include antibodies, portions of an antibody such as an Fab fragment, small molecules, and the like—which then bind to molecules specifically associated with cancer cells. Examples include surface receptors, or molecules within a cell. Other examples include molecules secreted by cells or those in the neighboring tissue stroma. These molecules are labeled with an optical tag. Examples include is fluorescent, phosphorescent or luminescent, and encompass both organic and inorganic tags. Further, in exemplary embodiments, a wide array of fluorescent conjugates can be utilized. While fluorescein and Indocyanine green ("ICG") have FDA approval, a wide array of dyes may be utilized. In certain embodiments, any fluorescent conjugate with an excitation frequency of about 640-800 nm and an emission frequency of about 660-820 nm may be utilized, as would be apparent to one of skill in the art.

The use of in vivo targeted agents is made possible by the ability to molecularly characterize tissue during biopsy during the initial diagnosis. One example is breast cancer (but this is representative of any disease site that has a molecular marker that can be assayed); Initial diagnosis of breast cancer often begins with physical exam and/or mammogram. Currently, to confirm the diagnosis of breast cancer, a biopsy is then taken and molecular subtyping is done. For example, a biopsy may confirm the presence of ductal carcinoma in situ ("DCIS") or invasive cancer, and staining or genetic (such as mRNA) analysis can be done to determine Her2 overexpression. A molecular marker can then be chosen to bind to this tumor type.

Although not all cancers have a distinctive cell surface marker amenable to antibody labeling, many common cancers do, including prostate cancer (Taneja S S. *ProstaScint (R) Scan: Contemporary Use in Clinical Practice*. Rev Urol 2004; 6 Suppl 10:S19-28) head and neck squamous cell carcinoma (Cetuximab Blick SKA Scott L J. *Cetuximab: a review of its use in squamous cell carcinoma of the head and neck and metastatic colorectal cancer*. Drugs 2007; 67:2585-2607) and Her2 overexpressing breast cancer (Hortobagyi G N. *Trastuzumab in the Treatment of Breast Cancer*. New England Journal of Medicine 2005; 353:1734-1736). Various other examples are possible. In the presently presented embodiment, the system is demonstrated with a Her2 overexpressing breast tumor, which comprises approximately ⅕th to ⅓rd of all breast cancers and in which the effect of MRD on recurrence and survival is well studied. In the US alone, this cancer results in roughly 60,000 Her2+ lumpectomies annually. Other examples include prostate cancer.

In the various embodiments contemplated herein, if a patient's tumor expresses a tumor-specific marker, for example Her2+, the patient's cancerous cells can be labeled prior to surgery. That is if the patient is Her2+, under certain embodiments of the system the surgeon can then preoperatively inject the patient with fluorescently labeled Trastuzumab (an antibody that specifically targets Her2)

approximately 24-72 hours before the surgery. In such embodiments, the antibody specifically binds to (and thus labels) the Her2+ tumor cells within a patient's body, including both the gross and microscopic aspects of the disease. This strategy has been demonstrated in multiple animal studies, as well as a clinical trial in breast cancer. As apparent to those skilled in the art, any molecule that preferentially binds to tumor cells over the background tissues can be used.

In various embodiments, other common cancer subtypes can also be labeled. For example, many breast cancers are estrogen receptor (ER) and/or progesterone receptor (PR) positive, and a fluorescently labeled estrogen or progesterone molecule (or antibody against the receptor) can be used to label these cells in vivo. Another example is prostate cancer, where a variety of anti-prostate specific membrane antigen ("PSMA") molecules exist that can be used to label prostate cancer within patients. Furthermore, many cancers, including breast cancer, are "PET-Avid," meaning that they have high glucose uptake due to their elevated metabolic activity. In these embodiments, commercially available fluorescently labeled glucose molecules can be injected preoperatively in the same manner as a fluorescently-labeled antibody to specifically target and label the cancerous cells, as would be apparent to one of skill in the art. Furthermore, there are cancer specific targeted molecules, such as those developed by Blaze Biosciences ("Tumor Paint"), and Avelas Biosciences (AVB-620).

Certain improvements to the system extend applicability of this system 1 to other breast cancer subtypes and cancers by exploring additional targeted imaging agents Selection of the optimal fluorophore for intraoperative imaging includes: (1) Potential FDA approval for clinical translation; (2) Near-infrared emission wavelength within the "optical window" of tissue; (3) An excitation and emission wavelength outside the visible spectrum (>700 nm) enabling seamless integration in the operating room without adjusting lighting; (4) A narrow emission bandwidth such that a highly selective optical filter can block tissue autofluorescence; (5) A narrow absorption bandwidth to remove background using spectral un-mixing. Candidate fluorophores include fluorescein, indocyan green (ICG) and IR800CW fluorophore made by LICOR Biosciences (Lincoln, Nebr.), which has been used in several clinical trials for guiding tumor resection including head and neck, renal cell (NCT02497599), rectal (NCT01972373) and breast cancer (NCT01508572).

In order to quantify the sensitivity necessary for the optical detection, the specificity of Trastuzumab for HER2 overexpressing (SKBR3) and non-overexpressing (S1) cells lines have been quantified, both in vitro and in vivo. Using CellProfiler cellular fluorescence is quantified against a known standard to determine the concentration (antibodies/μm2) on the cell surface. At 10 μg/ml of Trastuzumab ~30,000 antibodies/μm2, are seen on SKBR3 cells, while only 1,700 antibodies/μm2 are seen as background (S1) binding, for a signal to background ratio (SBR) of 17. The areas of the SKBR3 and S1 cells are 120 and 50 μm2, respectively, for a total of 3.6×106 and 8.5×103 antibodies bound to SKBR3 and S1 cells, respectively. Higher concentrations of Trastuzumab saturate binding of SKBR3 cells at 45,000 antibodies/μm2, thereby reducing SBR. Similarly, binding of an anti-PSMA antibody (J591) to prostate cancer cells has been quantified.

Figure 8A:
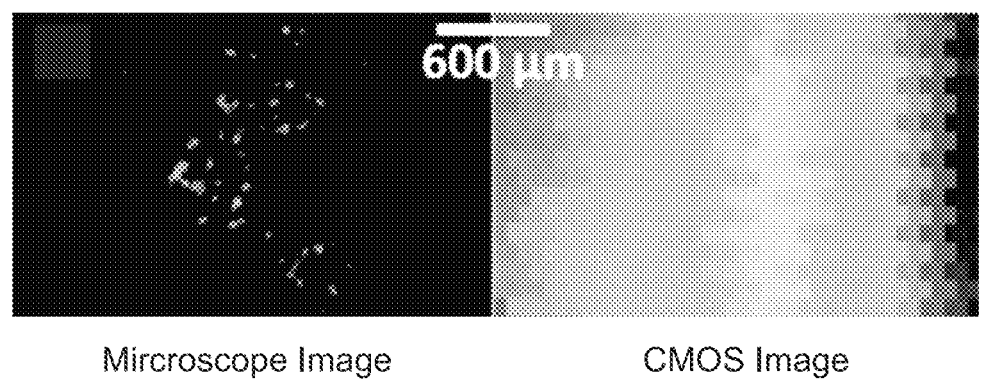
FIG. 8A depicts SKBR3 cells visualized with a CMOS imager, showing the microscope image (left) and CMOS image (right).
Figures 8B, 8C:
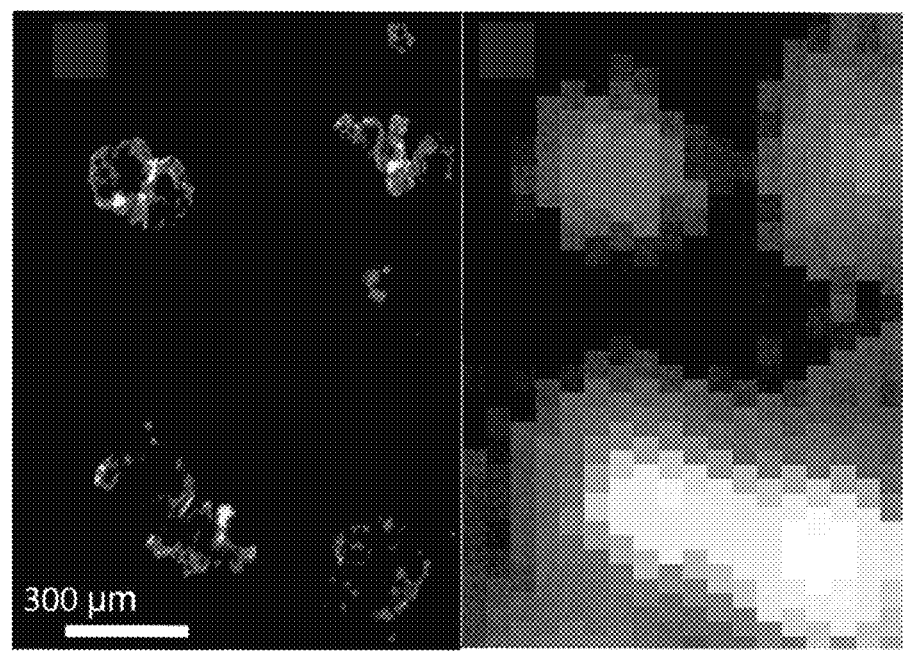
FIG. 8B depicts a microscope image of 4 distant foci of SKBR3 HER2+ cells stained with anti-HER2 and q-dot 705 secondary in Matrigel, simulating MRD.
FIG. 8C is an image taken with a planar array, according to one implementation, where light is inserted into the waveguide.

To demonstrate that an anti-HER2 antibody can be directly conjugated to a fluorophore and retain its binding specificity, anti-HER2 antibody (Cell Signaling, Danvers Mass.) conjugated to the AlexaFluor 647 accurately labeled SKBR3 cells cultured on top of S1 cells FAs, simulating a foci of microscopic residual disease within healthy breast tissue epithelia. Three dimensional (3-D) cell cultures were developed to more accurately represent cellular systems in vivo, and use these models to characterize the imager, as shown in FIGS. 8A-8C. IR800CW has been conjugated to Trastuzumab, and demonstrated specific labeling to HER2-overexpressing tumor cells both in vitro and in vivo. Another antibody, OS2966, an anti-beta-integrin antibody with binding specificity to triple negative breast cancer, can be used.

The quantification of Trastuzumab binding to SKBR3 (HER2+) cells has been done. To validate the in vivo distribution of Trastuzumab, we subcutaneously implanted HER2 over-expressing HCC1569 cells and MDA-MB-231 cells (basal subtype, HER2 non-expressing) as the negative control, and injected increasing amounts of Trastuzumab (10, 50, 100, 1000 μg) via intraperitoneal (IP) injection. Mice were sacrificed at 24, 48 and 96 hours and both tumor, kidney and liver were removed and stained for Trastuzumab binding. Selective binding of 1 mg Trastuzumab to HCC1569 cells in vivo, at a concentration of 40,000 antibodies/μm$^2$, established that 1 mg of Trastuzumab should be injected at 48-96 hours preoperatively in our mouse model. Tumor to healthy tissue binding ratio was ~10 (h,i), and concentrations of ≤100 μg did not show appreciable binding.

Other embodiments include near infrared and infrared fluorophores, both organic and inorganic, whereby the emission spectra can be optically distinguished from the excitation spectra. Exemplary embodiments of the system use specifically targeted and tagged FDA-approved antibodies to label targeted cells in vivo and visualize them with a novel-imaging device. Other embodiments include conjugation to small molecules and peptides targeting cancer cells, molecules secreted by cancer cells or molecules in the surrounding stroma. In certain embodiments, these antibodies may be conjugated to a fluorophore, though other antibody conjugates are possible, as would be apparent to one of skill in the art.

Standard fluorophores require optical filters to remove the excitation light, which is often many times (1,000-100,000×) the fluorescent signal. In certain implementations, any fluorophore or luminescent particle with a relatively long (>500 ns) luminescent or fluorescent lifetime and size under about <100 nm can be used for time gated imaging. As described below, time-gated (also called time resolved) imaging enable significant reduction in the optical performance for an optical filter and, in some cases, elimination, of the requirement for an optical filter. It is understood that these particles can be inorganic, can be coated with a biocompatible layer and can be functionalized to attach proteins and small molecules to its surface.

In certain implementations of the system 1 up-converting nanoparticles ("UCNP") are used as optical tags. As described herein, the use of UCNPs, absorbing in the near infrared range (800-1200 nm) enable time-gated imaging whereby the optical filter can be eliminated, reducing device cost, decreasing complexity of fabrication, and thinning the device.

In implementations using an inorganic or organic optical label capable of up-conversion or 2-photon excitation, the label absorbs in the near-infrared to infrared range, and up-converts emitted light, such that the tissue surface can be illuminated directly through the sensor itself while the emitted light is converted to a wavelength that is absorbed by the imager.

Figure 9A:
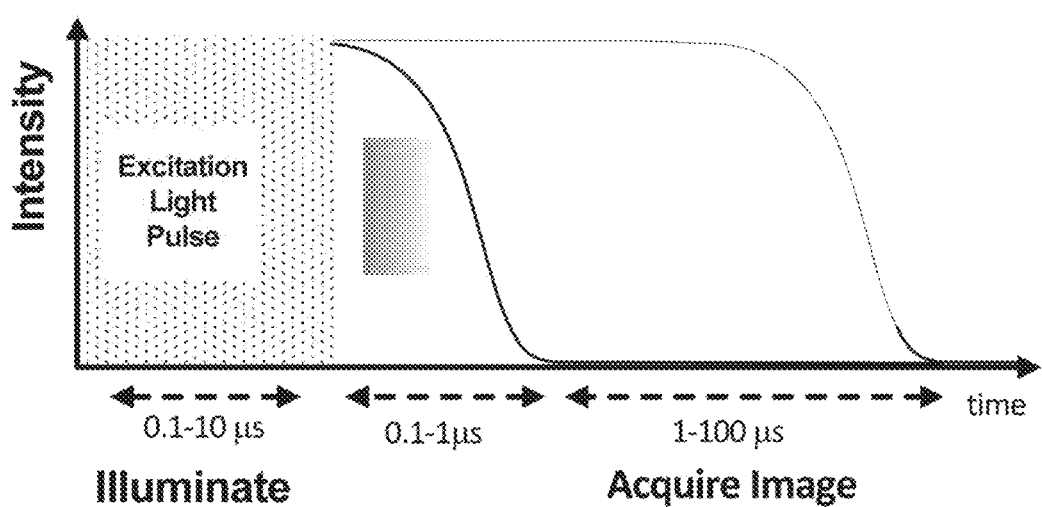
FIG. 9A depicts florescence intensity over time during time gating imaging where the excitation light is pulsed on and off, according to one implementation.
Figures 9B, 9C:
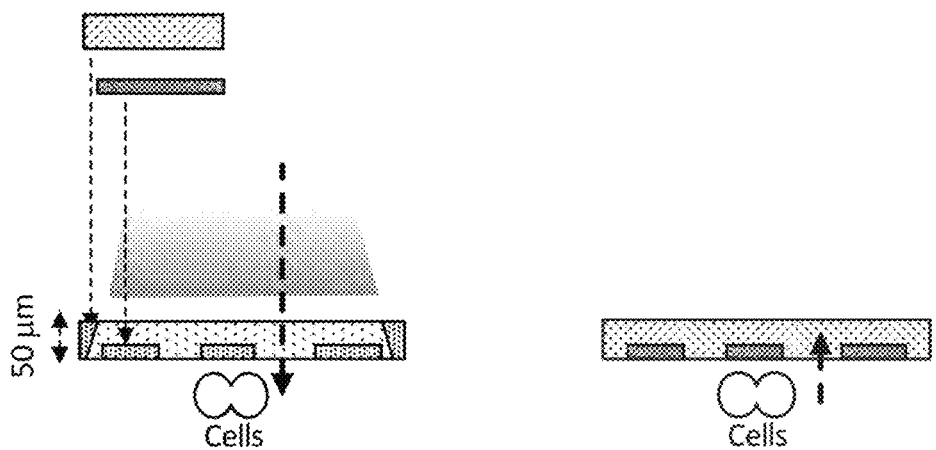
FIG. 9B depicts a schematic side view showing that a silicon imager according to one embodiment is effectively transparent at 1200 nm.
FIG. 9C depicts a schematic side view showing an implementation where upconversion ensures that the fluorescent signal from labeled cells is reduced to a wavelength visible to photodiodes.

UCNPs consist of Lanthanide-doped and absorb near-infrared ("NIR") light and emit at shorter wavelengths and higher energies in the visible or NIR band. Depending on size, UCNP scan have luminescent lifetimes of 1-100 microseconds depending on their size-orders of magnitude larger than traditional, organic, fluorophore, which range from femto to nanoseconds. An illustration of the imaging strategy referred to as time gated imaging is shown in FIGS. 9A-C, which depict time-gated imaging (FIG. 9A). In FIG. 9A, the excitation light is pulsed on and off. While the pulse is off, the auto-florescence of the unlabeled tissue is allowed to luminesce for an interval. Then, an image is acquired such that only the UCNP-labeled tissue is recorded. This process can be repeated for increased SNR. As shown in FIGS. 9B-C, the silicon imager is effectively transparent at 1200 nm, allowing illumination directly through the imager itself, while upconversion ensures that the fluorescent signal from labeled cells is reduced to a wavelength visible to photodiodes (for example 800 nm). In various implementations, UCNPs can be used to enable time gating imaging with NIR and IR wavelengths. Accordingly, in implementations using UCNPs, the imager 102 does not require an optical filter 114. In these implementations, by rapidly illuminating, and then waiting to image the tumor bed, background light and autofluorescent can be eliminated. The background light is turned off within nanoseconds (or less), so that no background light remains. The autofluorescent light, which results from the fluorescent decay of organic molecules, decays on the order of femto to nanoseconds, and thus is virtually absent when the image acquisition is delayed. Consequently, the only light remaining is the NIR or IR signal from the cells tagged with UCNPs. Therefore, with IR absorption and up conversion, certain exemplary embodiments can eliminate the need for an optical waveguide 116 and optical filter 114 (described variously elsewhere herein). It is understood that the elimination of these components more readily allows the application or integration of the imager 102 to a medical device, such as a scalpel. In these embodiments, the thinner imager 102 enables direct integration with surgical instrumentation—essentially resulting in a coating or "paint" that only marginally increases the physical dimension of a device, but allows real-time imaging of microscopic disease intraoperatively.

The use of such fluorescent antibodies and small molecules and other molecular labeling techniques allow the use of the various embodiments of the imaging device (or "probe" or "imaging probe") to detect the presence of these labeled tumor cells for visualization and resection. In certain embodiments, a modular approach is adopted, such that the provided imagers can be assembled in a variety of shapes, sizes, and configurations depending on the specific application. These facilitate customization to a specific patient's anatomy and tumor size, or customization based on tumor type. Accordingly, certain implementations feature a three-dimensional imaging configuration. In the implementations whereby an ultra-thin imaging platform is made, the sensor surface can be flexible. In further implementations, the imager may be directly integrated into another surgical instrument. Exemplary embodiments also feature a planar form factor, as is described herein.

The various embodiments and examples described herein relate to enabling the visualization of fluorescent or luminescent molecules within the body as well as on tissue excised from the body. The disclosed embodiments are applicable to any disease which presents a selective biological (or inorganic) agent capable of identifying the diseased cell. The description disclosed herein focuses on cancer as an exemplary application, but those of skill in the art will readily identify other possible applications. The various disclosed embodiments are thus capable of illuminating cells located within the body (or excised tissue sample), and gathering, focusing or de-blurring, and optically filtering the fluorescently emitted light to remove background light. Collectively, and for brevity, the disclosed apparatus, systems and methods will be referred to herein as "the imaging system," which comprises an "imaging probe" comprised of an probe 100 and an imager 102 in operational communication with an external monitor. However, the use of any of these terms is in no way intended to limit the scope of the described embodiments to a specific modality.

Thus, as shown in FIGS. 2A-2C, in exemplary embodiments, the imaging system comprises an imaging probe 100 configured to be inserted into the body cavity of a patient and capable of receiving a visual signal via an imager 102 and then transmitting the signal to an external monitor for viewing. In certain embodiments, the imaging probe 100 is configured to be integrated with another medical device, such as a scalpel or within another device, such as a DaVinci system. In alternate embodiments, it can also be a stand-alone probe 100.

In such embodiments, light is generated from an external source and guided to the imager which captures, converts, and transmits this signal to an image relayed to the user by way of an operational connection. In certain embodiments, various aspects of the probe and imager can be fabricated in a planar format, in any size, as will be apparent from the present disclosure. In certain embodiments, to be easily placed within the body, the diameter of the probe and sensor should be less than 2-3 cm. This planar structure can potentially be bent to create a 3D structure, or multiple planar devices can be put together to create a 3D structure, enabling simultaneous imaging in multiple directions to more efficiently image a complex surface or cavity. In various implementations, a flexible imaging surface is created by thinning a CCD or a CMOS imager to <50 um thick. Accordingly, by way of the probe 100, the imager 102 can be brought near to, or in contact with, tissue, and can be integrated within another surgical instrument as desired.

Previously, despite the ability to identify the tumor using in vivo molecular labels, no known imaging device existed capable of allowing the acute visualization of the MRD cells (that is, less than about 1,000,000 cells), thus leaving gross resection with empiric resection of surrounding at-risk tissue as the only option for clinicians. One aim of the present system is visualization on the order of a few hundred cells.

In use according to certain embodiments of the system, after the initial resection the surgeon is able to utilize the imager to scan and identify any residual tumor(s) in the tumor bed with the custom-imaging probe, ensuring complete resection in a single operation. In exemplary embodiments the surgeon is capable of visualizing cancerous cells in vivo, during the procedure, by utilizing a microfabricated imager directly within the tumor bed, thus imaging the resection bed microns from the surface and obtaining a thorough high resolution scan of the entire tumor bed.

Figure 1D:
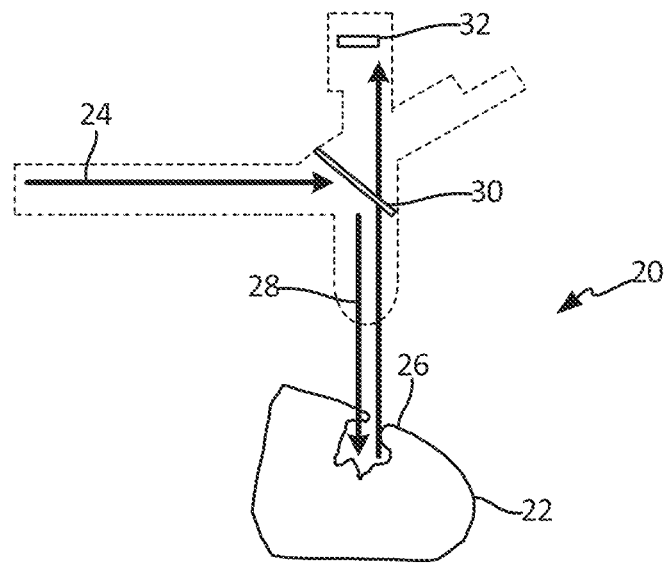
FIG. 1D depicts an overview of a prior art imager.

Returning to FIG. 1D, prior art imagers typically utilize a single large microscope 20 placed above a patient 22, wherein excitation light 24 is transmitted into the tumor bed 26 and sensed by an external lens 28, filter 30, and imager 32. This approach has two principle disadvantages. First, the rigid optics of a microscope limit the view to line of sight only. Because the tumor bed is a small, complex cavity, this approach misses the vast majority of the tumor bed surface, especially the side portions. Second, because of the size of the microscope and lens, cells must be imaged from outside the tumor bed. This substantial working distance decreases sensitivity, making it difficult, if not impossible to both identify a focus of 200 cells on the tumor bed surface and thoroughly and rapidly image the entire surface area of about 5 cm². In another embodiment, the probe is directly integrated with the resection tool (for example a scalpel or bovie), and cellular imaging information is processed in real time by way of the visualization system (described below).

It is understood that fluorescent imaging requires several optional conditions that can include (1) sample illumination, (2) gathering of fluorescent emitted light, (3) filtering of background light, and (4) converting an optical image into an electronic one. Other configurations are of course possible.

Returning to the presently-disclosed system 1, and as is shown in FIG. 2D, in certain implementations, a tumor bed 124 in which the cells are labeled with specific fluorescent-tagged antibodies 126 is observed. In various embodiments, the imager 102 may be a sensor, a photo-detector or other device capable of transducing a light signal into an electrical signal, as would be known in the art. As is apparent in FIG. 2D, the imager 102 is located within the cavity and adjacent the tumor bed. In certain implementations, a reflector 128 is employed to alter the direction of light transmitted by way of the light guide 110. Current imaging methods, as noted above, use a lens above the tumor bed to gather and focus light. This requires a minimum spacing between the sensor surface and tissue for focusing. Because light diverges over a distance, this results in a significant loss of signal. Therefore, the closer the imager is to the tumor bed surface as in the embodiments herein, the more fluorescent light (emitted by the labeled cells) can be gathered by the imaging probe and the strategy of the imager presented here is to place the imager as close to the tissue surface as possible, increasing sensitivity and spatial resolution by gathering light before it diverges. One of the challenges presented by placing the imager inside the cavity is the illumination of the cavity such that the fluorescence may be detected. In the exemplary embodiments of the system described herein, the proximity of the light source and imager to the tumor bed results in the necessary illumination. Because the system utilizes an imager placed within the tumor bed, rather than above it, and because the imager is opaque, exemplary embodiments of the system employ various apparatuses designed to guide the light around the imager surface, thus illuminating the tumor bed.

Fabricating a sub-millimeter thin, planar form-factor imager directly within surgical instrumentation necessitates a departure from the traditional optics associated with a fluorescent microscope. Various implementations of the presently disclosed imager place a small, planar imager (CMOS or CCD) and embed it directly into the surgical instrument, customizing it for near-field fluorescent imaging of tissue. An integrated circuit ("IC") or computer chip platform, based on complementary metal oxide semiconductor ("CMOS") technology, is preferable because it uses inherent components (photodiodes) to convert light to an electronic signal, with feature sizes down to 100 s of nanometers ensuring high spatial resolution, has integrated on-chip electronics for signal processing, and is fabricated in commercial foundries in an arbitrarily large (8-12 inches) planar array with thicknesses less than 100 μm.

In certain implementations, a microscopic fluorescent imager 102 can be applied he surface of a surgical device with a sub-millimeter thin, planar fluorescent imaging array by "coating" (or embedding within) the device. Manipulating the imager 102 within the tumor bed ensures that all resected tissue is imaged in real-time with microscopic precision, solving the problems of sampling error and co-registration, inherent in post-operative evaluation of tumor samples. It is understood that placing the photosensitive surface of the imager just microns from the tissue significantly increases sensitivity and spatial resolution while reducing device complexity. By mitigating the losses associated with light diverging as the distance from the fluorophore squared ($d^2$) the sensor (1) gathers significantly (quadratically) more fluorescent signal than imagers operating outside the tumor bed, and (2) eliminates the need for optics by capturing light before it diverges.

One embodiment of the imaging system comprises an imaging probe 100 with at least one microscopic fluorescent imager 102 at the tip, capable of being placed and manipulated within the tumor cavity while imaging foci of microscopic residual foci of cancer cells after initial surgical excision. The patient's pathologic cells are labeled prior to surgery by systemically injecting a biologic, conjugated to a fluorescent molecule specifically targeted against specific disease cells. By way of example, in certain embodiments Herceptin for HER2 over-expressing breast cancers may be used. Other examples include, but are not limited to, anti-PSMA antibodies for prostate cancer; Cetuximab for head and neck and colorectal cancer; or glucose conjugated to a fluorescent molecule for imaging hyper-metabolic (typically cancerous) cells. In certain implementations, molecules labeling more general markers of cancer can also be used.

The labeled cancer cells will fluoresce when illuminated. In one implementation the system gathers and focuses light by using an array of microlenses. In an implementation, no lenses are used, and spatial resolution is obtained by placing the device close to the tissue surface and incorporating angle sensitive imaging (discussed subsequently). In certain implementations, a microfabricated optical interference filter 114 removes background light, and an imager then resolves the image translating it to a signal alerting the surgeon to an area of cancer cells. The image can be either be formed by a microlens covering the imager surface, or directly from the tissue surface, for example without being focused by a microlens. The imager can be an angle selective imager, such that the photodiode array has the collimators integrated on it, as described below. One embodiment includes recording the angles of incoming light. Another embodiment, described more in detail subsequently, preferentially images specific angles of incoming light, thereby recording light coming from a specific angle only. This helps to eliminate cross-talk between the adjacent pixels, deburring the image and blocking light from adjacent areas on the tissue or sample surface which reduces background.

In these embodiments, the imaging system consists of an array—or arrays—of imagers each simultaneously fluorescently imaging a small area of the tumor bed. Since the optical signal is diminished by the square of the distance covered, placing the imager near or against the tumor bed allows the user to obtain a significantly greater signal. In certain exemplary embodiments, and in order to illuminate the tumor bed lying underneath the opaque imager, the imagining system utilizes a novel approach wherein the light around and along the sensor surface, using an optical waveguide to illuminate the tumor bed.

Figure 2E:
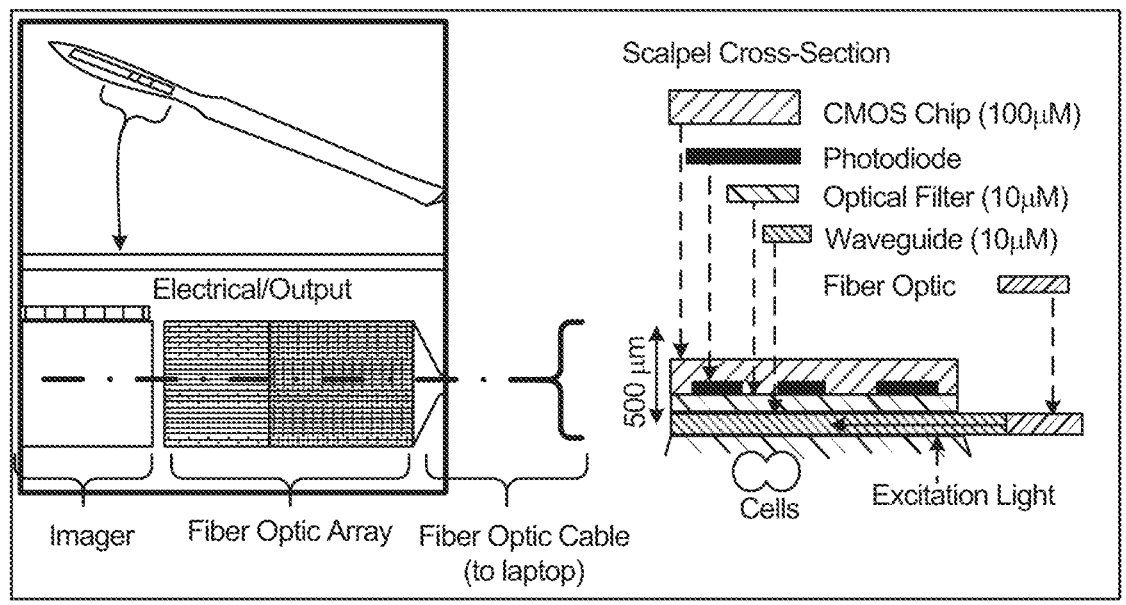
FIG. 2E depicts a detailed schematic overview of the imaging system, according to another exemplary embodiment.
Figure 2F:
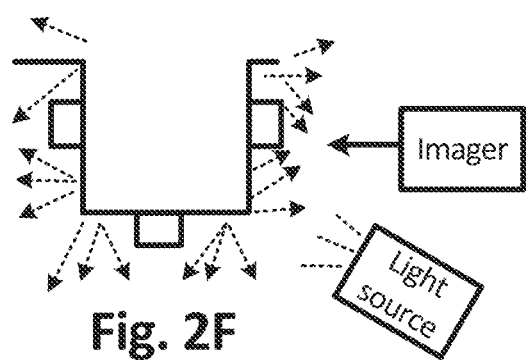
FIG. 2F depicts a cross-sectional view of the imagining system showing the reflection of light against the sides of the probe, according to another exemplary embodiment.
Figure 2G:
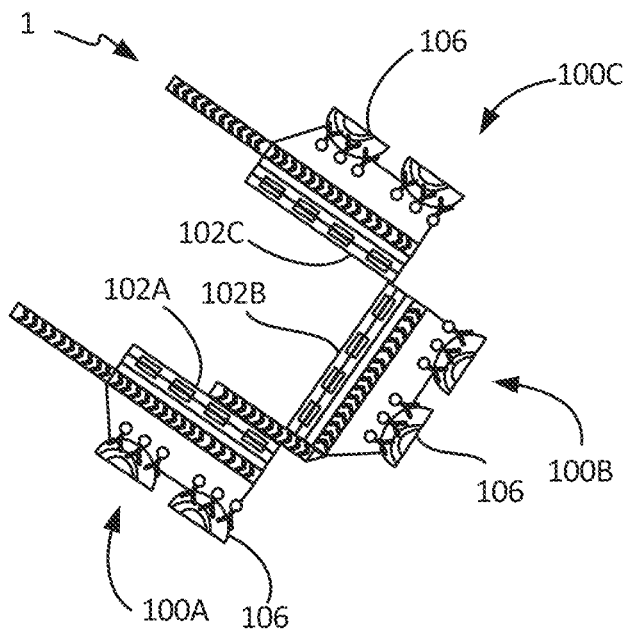
FIG. 2G depicts a detailed cross-sectional view of the imagining system showing imagers disposed on several sides of the probe, according to another exemplary embodiment.
Figure 2H:
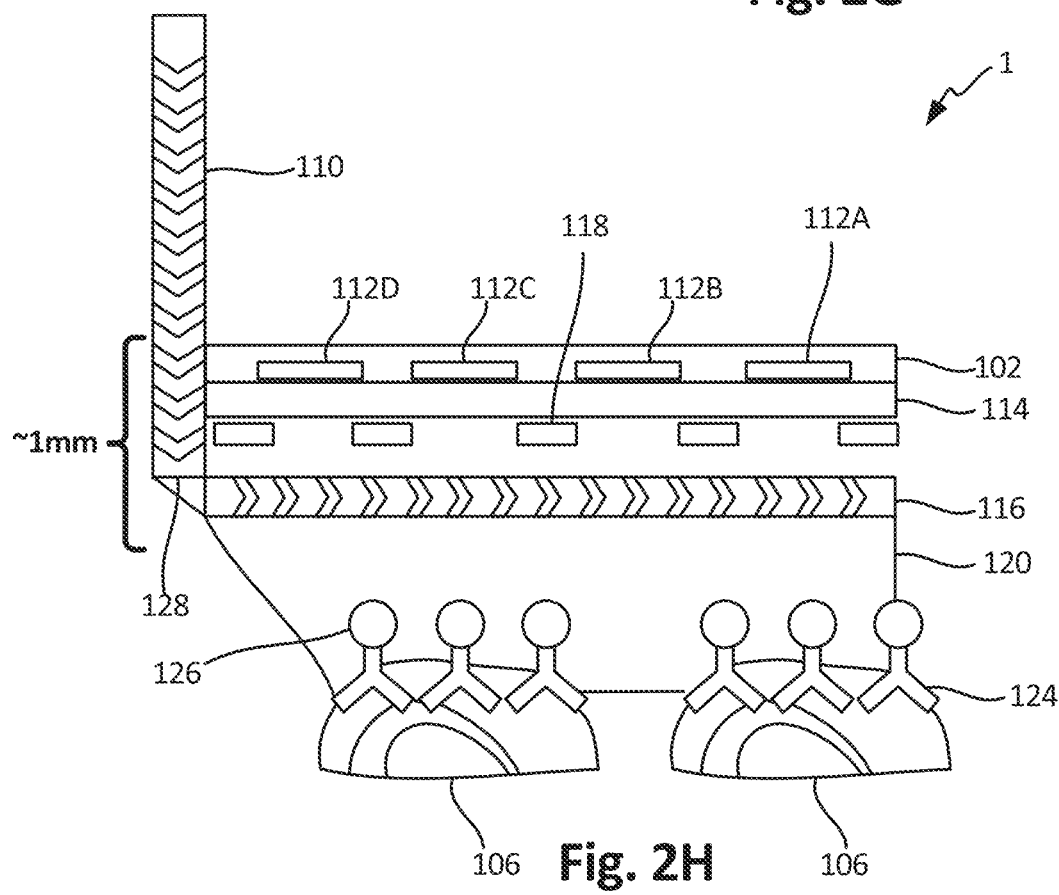
FIG. 2H depicts a detailed schematic overview of the imaging system, according to another exemplary embodiment.

In another implementation, the micro-lenses can be completely removed, and by virtue of the sensor platform being close to the tissue surface, light is captured before it diverges, mitigating the need for a lens array, as best shown in FIG. 2E.

In exemplary implementations, an angle insensitive optical filter 114 is provided. In these implementations, the filter 114 consists of a material that absorbs light at the excitation (illumination) frequency and allows the fluorescently emitted light to pass through to the imager.

As shown in the implementations of FIGS. 2A-2E, certain implementations of the imaging system 1 have a microscopic fluorescent imager 102 disposed on or otherwise integrated into a device 100. In these implementations, the imager 102 is capable of being placed and manipulated within the tumor cavity so as to access the tumor bed (as shown in FIG. 18A-D while imaging foci of microscopic residual foci of cancer cells after initial surgical excision). The patient's pathologic cells are labeled prior to surgery by systemically injecting a biologic, conjugated to a fluorescent molecule or inorganic luminescent/fluorescent particle, specifically targeted against specific disease cells. By way of example, in certain embodiments Trastuzumab for HER2 over-expressing breast cancers may be used. Other examples include, but are not limited to, anti-PSMA for prostate cancer; Cetuximab for head and neck and colorectal cancer; or glucose conjugated to a fluorescent molecule for imaging hyper-metabolic (typically cancerous) cells. Imaging agents (such as fluorescently-tagged antibodies and small molecules) that specifically target neighboring tumor stroma or molecules secreted by tumor cells can also be used for in vivo labeling and imaging with the imager described here.

FIGS. 2A-2E depict a schematic overview of certain exemplary embodiments of the system 1. In these embodiments, an imaging probe 100 comprises an imager 102 which is configured to be placed inside a cavity 104 left by a resected tumor to identify labeled disease cells 106. In these and other embodiments, the imaging probe 100 can be attached at the distal end of a handle or other operational tool 108. In certain embodiments, the imaging probe 100 transmits the detected results out of the body of the patient, as described in detail below. As depicted in FIG. 2C, in certain embodiments, the imaging probe 100 has a plurality of sides 100A, 100B, 100C, each comprising an imager 102A, 102B, 102C, thus allowing the collection of imaging data from numerous aspects. Thus, by way of example, in certain embodiments a surgeon is able to scan the tumor bed and be visually alerted to individual diseased regions.

Recognition and image processing of tumor cells can be accomplished by either the operator visualizing the image directly from the sensor, or an image that has been processed using computation techniques to highlight the area of cancer cells. The resulting image can, for example, also be viewed as a reconstruction on a laptop or other monitor (as illustrated in FIG. 8, FIG. 25A-25B, FIG. 26, FIG. 20). Still further, in certain embodiments the imaging system can be configured to alert the surgeon when a threshold level of signal is detected, as would be apparent to one of skill in the art. Still further, local variations in cell labeling, background due to non-specific binding, blood, and tissue, can be determined by examining pixels surrounding those imaging the tumor. Automated cell identification algorithms can identify cells as shown in the cell cluster algorithm in FIG. 27A-C. Sensitivity and specificity of cell recognition can be tuned by changing threshold parameters for image recognition.

As an example we have imaged through blood and through increasing imager-cell separation, which replicates imaging through increasing thickness of tissue. Intraoperative cellular imaging necessitates imaging through thin layers of overlying blood and tissue, which degrades image quality (both spatial resolution and intensity (SNR)) by (1) scattering, (2) absorption, and (3) divergence over increasing imager-cell separation. In FIGS. 30A-30B, dilutions of a relatively thick, highly scattering and nearly opaque 250 µm layer of blood reduce intensity (SNR) by a maximum of 10 dB, but do not significantly degrade spatial resolution, as scattering, which dominates over absorption isotropically scatters light, essentially trading signal for background. However, increasing imager-cell separation decreases both spatial resolution and intensity, but due to ASG, SNR is reduced less rapidly than quadratically (at only 6 dB/mm, FIG. 30CB). Clusters smaller than a pixel (<50-200 cells) appear as a point-source, and SNR scales more rapidly (30 dB/mm) with imager-cell separation. Given an SNR of 15 dB at 650 um for 100-cells, with a 32 dB improvement a goal of single cell detection is achievable.

Figure 31A:
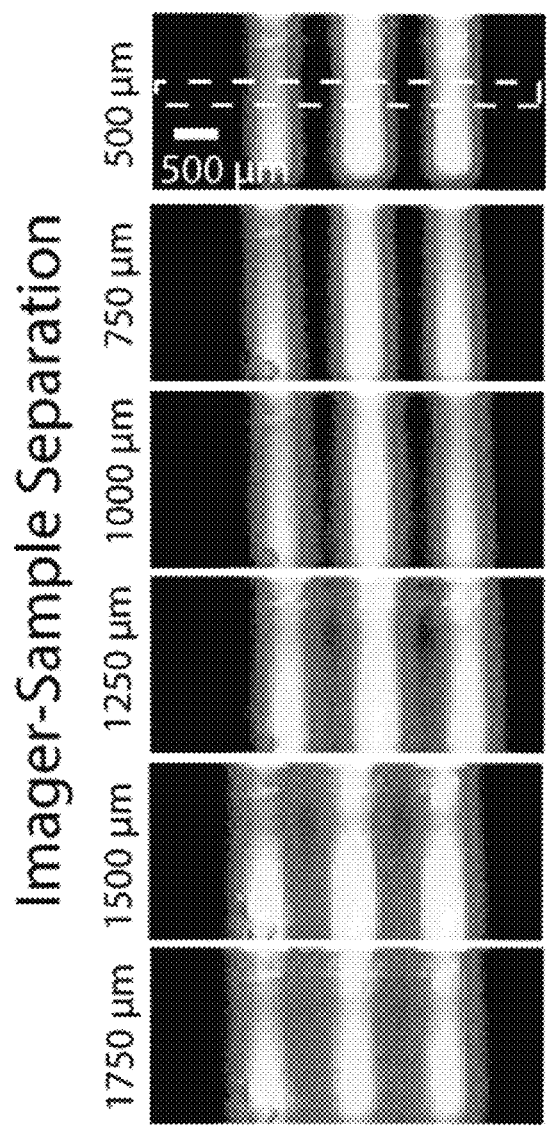
FIG. 31A is a series of images showing the fluorescence at various imager-sample separation distances.
Figure 31B:
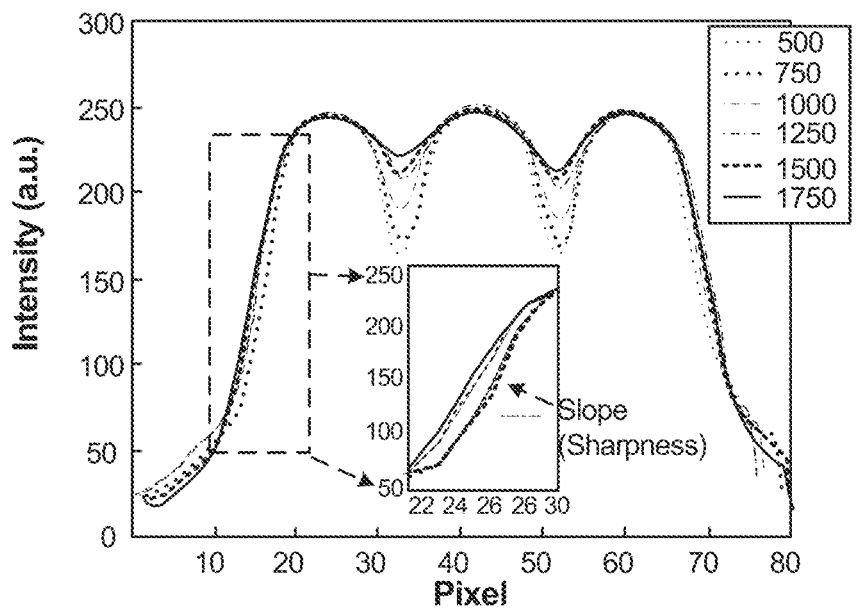
FIG. 31B plots the profile vs. imager-sample separation of the separation implementations of FIG. 31A.
Figure 31C:
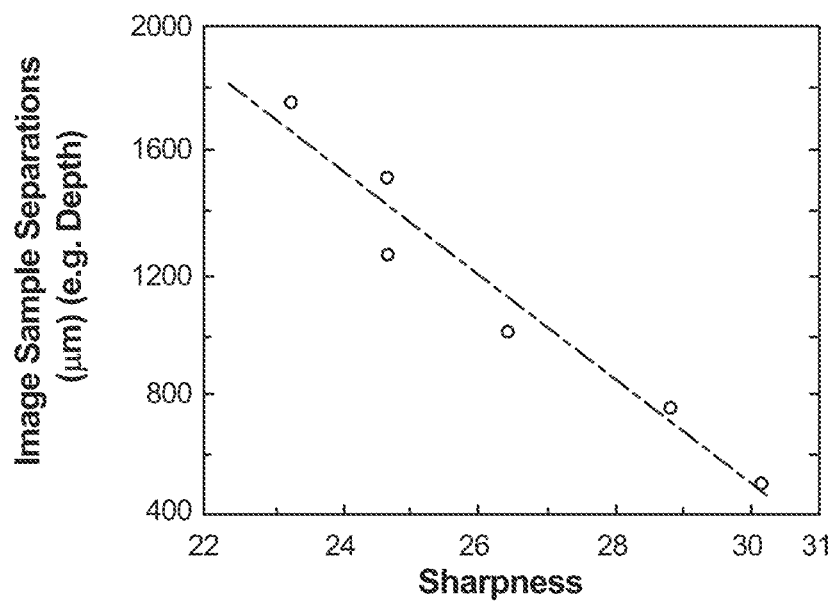
FIG. 31C plots the depth vs. feature sharpness of the separation implementations of FIG. 31A.

Additionally, the imager disclosed here can be applied to imaging MRD and mLNI (microscopic disease) below the tissue surface (depths 1-10 mm). Blood accumulation is limited by irrigation, aspiration, and physical pressure of the imager on the tissue. Light intensity is increased by 100× for depth imaging, requiring a thicker filter 114 for rejection. Longer wavelength fluorophores (IR800CW, ICG) for deeper penetration can be used. SNR calculations represent a worst-case scenario, relying on a single pixel: summation of neighboring pixels further increases SNR. The depth of the cell cluster can be determined from the profile of the image as shown in FIG. 31A.

Image processing may include local background subtraction, whereby values from neighboring pixels are used to measure the background. As discussed previously, images taken with different wavelengths of light in rapid succession can be used to (1) calibrate out non-uniformities in illumination, and (2) auto-fluorescence background and (3) dark current, offsets and low frequency noise processes, such as flicker noise.

Exemplary embodiments of the imaging system utilize a microlens array. These microlens arrays minimize the distance between the probe 100, imager 102 and the tumor bed surface 124. FIG. 2D depicts a detailed overview of an exemplary arrangement of the system showing the operational structure of the imager 102. In these exemplary embodiments, the probe has a remote light source (not shown) that provides illumination light via a light guide 110, the imager 102 further comprising a plurality of individual pixels 112A, 112B, 112C, 112D, an optical filter 114, a waveguide 116, a waveguide stencil 118 and a microlens array 120. In exemplary embodiments, these components are understood to be disposed in a generally planar fashion to the extent that is possible, and layered adjacent to one another as provided, so as to create a generally planar imaging surface 122. Transmission and processing of the resulting images is discussed herein. In certain experimental embodiments, the system features "macro-scale" components, such as a glass slide wave guide, or an off the shelf filter), without lenses. The total thickness of the imager 102 in this exemplary implementation is 1.5 mm. As would be apparent to one of skill in the art, other sizes are of course possible.

It is understood that as the imager 102 gets thinner (where "thickness" describes the distance between the imager surface and the tissue surface), various components can be eliminated. At larger imager thicknesses—such as those greater than 500 µm—microlenses 120 (as described for example below in relation to FIG. 3A) can be used. However, the imager surface to cell or tissue surface separations of less than 800 um, and more so at less than 500 µm, the microlenses can be eliminated, thereby simplifying the imager 102 and allowing it to be thinner and leading to overall improved performance. At even smaller imager— cell separations (<100 μm) the angle selective grids or waveguides (as described for example in relation to FIGS. 6-17) can be eliminated. However, when the goal is viewing deeper into the tissue, angle selective grids can be utilized. This is possible when using the UCNP nanoparticle, described below.

As shown in FIG. 2E, in exemplary implementations a fluorescent imaging array 102 is provided that is less than 500 μm thick which "coats," or is otherwise embedded within the surface of a surgical resection tool or probe, thereby transforming the tool itself into an imager. Imagers of varying thicknesses can be used, with thinner imagers having the advantage of minimizing changing the form factor of the underlying probe or surgical instrument. This enables the imager to be seamlessly inserted and maneuvered throughout the cavity via a minimal incision (1) instantly alerting the physician to any areas of MRD, ensuring complete resection of all disease in a single operation and (2) eliminating challenges of co-registration while ensuring (3) thorough microscopic imaging of cut surface solving the problem of sampling error.

In exemplary implementations, the system utilizes an imager 102 whose total physical thickness less than 500 μm, in certain embodiments less than 100 μm, and in certain embodiments less than 50 μm with the use of novel optical nanoparticles. There are 2 relevant thickness measurements: (1) the distance between the labeled cells and photodiodes (cell-photodiode distance) which is inversely proportional to spatial resolution (i.e. the closer the cells are to the photodiodes the sharper the image), and (2) the imager thickness which is the physical form-factor, and in which the thinner it is the easier it will integrate into surgical devices.

In these embodiments, the imaging system consists of an array (or arrays) of photosensitive elements (also called pixels, and included pixel-level circuitry) each simultaneously fluorescently imaging a small area of the tumor bed, operating in parallel to achieve high-speed imaging over the surface.

Since the optical signal is diminished by the square of the distance covered, placing the imager near or against the tumor bed allows the user to obtain an exponentially greater signal. In certain exemplary embodiments, and in order to illuminate the tumor bed lying underneath the opaque imager, the imagining system utilizes a novel approach wherein the light around and along the sensor surface, using an optical waveguide to illuminate the tumor bed. The labeled cancer cells will fluoresce, and we gather and spatially localize the light.

As shown in FIGS. 2A-E, in various implementations, the imager 102 can have a light source a fiber optic light guide; an elongate probe (or existing surgical instrument with the imager integrated on it) sized for placement inside the cavity 104 of the patient. Certain implementations further comprise at least one substantially planar detection surface, the detection surface further comprising an imager and a waveguide in luminary communication with the light source and an optical filter 114.

Figure 32:
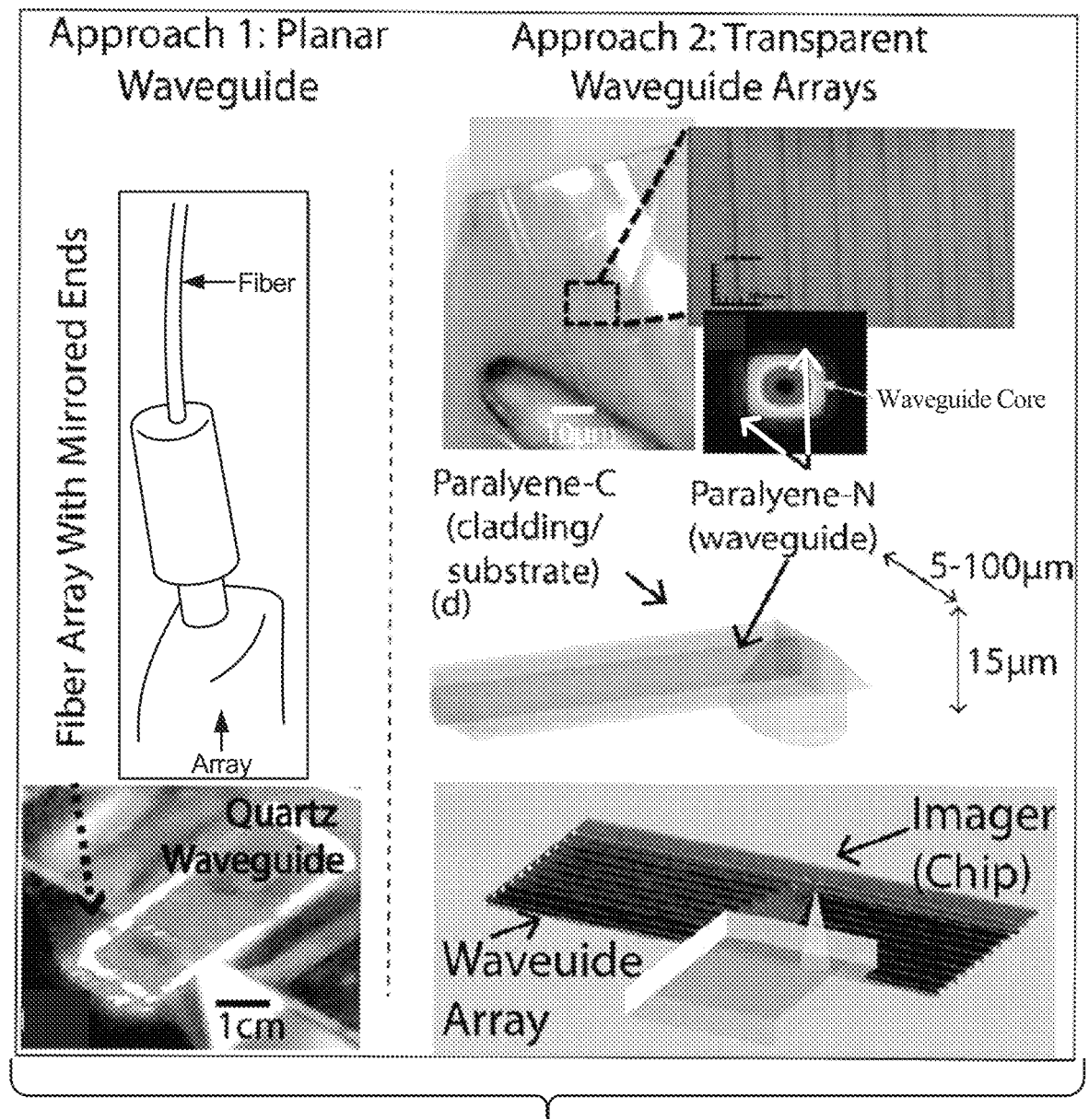
FIG. 32 depicts schematic representations of a planar waveguide and a transparent waveguide approach, according to various implementations.

One solution is to inject light along the sensor-tissue interface using a fiber optic array, terminating into a linear array of fibers microfabricated mirrored ends, bending light 90 degrees, to couple to a planar waveguide 500 μm quartz planar waveguide (FIG. 40A-40B). The close index of refraction of tissue and glass allows light to escape from the waveguide into the tissue. Other waveguide thickness are possible, including reducing the wave to a 100 μm thick quartz waveguide while reducing our custom fiber optics to 100 μm fibers for efficient coupling. Parylene-embedded ultra-thin waveguides provide spatial control over illumination (FIG. 32). Additional thinning of the wave guide and increased spatial control for illumination uniformity is achieved using a transparent optical waveguide array with vertical output ports. This enables efficient delivery of pump light with high spatial resolution without interfering with the fluorescent emission collection path. The vertical output ports direct light away from the imager, reducing optical bleed through. Taking advantage of the large refractive index contrast of n=0.022 between two types of Parylene (types N and C) compact photonic waveguides are realized. The output ports of these waveguides designed to be 45° (using an optimized etching process), coupling out light normal to the surface of the waveguide at specified locations. In the proposed scheme for illumination, light is first coupled to the waveguides outside the chip and then routed to the bottom of the imager chip. Optimizing the output port pattern, we reduce illumination variation.

Another approach to tissue illumination consists of directly affixing LEDs to the waveguide edge. Non-uniform illumination is calibrated by imaging an autofluorescent surface prior to use. Another approach to tissue illumination consist of LEDs mounted bordering the imager, with light directed away from the imager into the tissue.

Various implementations of the system utilize different strategies for spatial localization, such as nano-collimators or angle-selective gratings. Light diverges (as well as scatters and is absorbed) as it travels through tissue, blood, and the optical waveguide and filter 114 to strike the optical sensor array. In one implementation, we focus the light by using an array of microlenses. A microfabricated optical interference filter 114 removes background light, and an imager 102 then resolves the image produced by each microlens, translating it to a signal alerting the surgeon to an area of cancer cells. The imager can be an angle selective imager, which in addition to recording the spatial intensity of light, preferentially images specific angles of incoming light, helping to eliminate cross-talk between the adjacent microlenses. In other implementations, we do not use microlenses, but instead rely solely on the angle selective imaging to reduce image blur.

A principle aim of the presently disclosed embodiments is the reduction of the overall distance from the imaging surface to the cells in order to eliminate the need for microlens arrays completely. The incorporation of microlenses involved precision alignment and fabrication, adding complexity to the manufacturing process, and necessitates an reproducible imager to tissue distance to ensure proper focus. Therefore eliminating micro lenses significantly reduces device complexity and cost, and increases robustness. It is also understood that as the distance between the imaging surface (i.e. photodiode surface) and the cells is decreased below 500 μm, the amount of divergence of light is limited, which is allows for the elimination of the microlenses 120 (as described for example above in relation to FIG. 7A). In these implementations, the spatial resolution depends on minimizing the distance between the imager 102 and tumor bed. In these implementations, further spatial resolution can be achieved by deblurring using angle-selective gratings on pixels (as described below in relation to FIGS. 6-16.

In very close or optics-less implementations where the cell to photodiode distance is extremely small (such as <10 μm), components such as the angle selective gratings (as described below in relation to FIG. 7) can also be eliminated, as the divergence from the light is minimal. The elimination of the angle selective gratings can further improve optical sensitivity, as it grating physically blocks about 50% of the pixel surface. At these separations, single cell imaging is possible.

Implementations of angle selective gratings (also called nano-collimators and micro-collimators) are shown in FIGS. 24A-D and 6A-G. We have shown an increase in partial resolution 4× (FIG. 23) by reducing each pixel's viewing angle, defined by the full width half-maximum (FWHM), from 120° without ASG to 36° measured in air, and to 28° in fluid. This is achieved using only the inherent metal interconnect layers 1-5 to fabricate micro-collimators, measuring 2.4 µm wide by 6.8 µm tall, directly on the photodiode array (FIG. 24C). A key advantage is that no additional post-processing or microfabrication is necessary. Despite covering 50% of the photodiode, the strong rejection at large angles of incidence blocks 91% of background light, increasing SNR by 19 dB. The implementation shown here is only one possibility and any arrangement of metal interconnect layers within a CMOS or CCD manufacturing process could be used to create physical barriers that block light at selected angles.

Filtering of the background excitation light source—which can approach 1,000 to 100,000 times greater than the fluorescent signal is essential, yet adds space between the sample and the imager (photosensitive component). After being directed to the tumor bed 124 via the waveguide 116, the light induces fluorescence or other visual signals from the labels that are attached to the diseased cells, which is then passed back through the waveguide 116 to the imager 102. In certain exemplary embodiments, the system comprises an optical filter 114, as shown in FIG. 2D. In some of these embodiments, the optical filter 114 is an optical interference filter 114, which allows only a desired signal (such as a particular fluorescent wavelength of light) to pass through to the imager 102. In these embodiments, the optical filter 114 prevents background light, for example from the environment and the excitation light, so as to only allow the imager 102 to be reached by visual signals from the diseased cells 12. In certain embodiments, the ratio of the transmitted light to the blocked light can be around 104:1. In certain early implementations of the filter 114 were manufactured on a glass substrate and is about 500 µm thick. However, the filter layer 114 itself is only about 10 um—the glass substrate is required for physical stability. In various implementations, the glass substrate can be used as the waveguide 116. In certain implementations, the glass substrate can be thinned after fabrication to 100-200 um, reducing imager 102 thickness. In yet further implementations, the filter 114 can be directly patterned on the imager itself, reducing the total added thickness of the filter 114 to 10 um. Further, in certain embodiments, the waveguide 116 can be reduced to 100 um to decrease the cell to imager 102 distance, thereby both decreasing cell-photodiodes distance and improving spatial resolution and the imager thickness.

With the use of traditional optical fluorophores, the imager 102 can be physically thinned by fabricating the filter 114 directly onto the integrated circuit-based imager, thinning the optical waveguide, and physically thinning the integrated circuit-based imager. These improvements enabling reduction of the spacing between the photosensitive surface of the device and the cell or tissue sample to 100-300 um total thickness—less than 500 um, and can enable the elimination of the micro-lenses.

In certain alternate implementations, and as with time gating (resolved) imaging, the use of the filter 114 can be eliminated entirely.

Various implementations address the practical challenges of recognizing microscopic cell clusters within a complex physiologic three-dimensional tissue environment which includes (1) light penetration into tissue, (2) scattering and absorption through blood and tissue, and (3) imaging MRD within a large and heterogeneous background. Thinning of our fluorescence imager achieves an ultra-thin form-factor with micron proximity to the tissue surface, significantly increasing sensitivity and spatial resolution by capturing fluorescent light before it diverges. This eliminates the need for bulky and rigid focusing optics, reducing device complexity and size. Incorporation of on-chip microfabricated angle selective gratings further increases spatial resolution, improving signal to noise ratio (SNR), background subtraction and cell-cluster (MRD) recognition. Increases in pixel sensitivity (through strategies such as photodiode improvement and incorporation of PIN photodiodes) and illumination (excitation) light can increase MRD signal, enabling imaging through overlying blood and tissue, while improvements in optical filter 114 design reduce background.

Physical pressure of the contact imager against the tissue limits buildup of overlying blood and reduces variation in tissue-surface profile. SNR defines the detection limit of the imager, and system level performance, incorporating illumination, spatial resolution and image recognition, can be quantified by sensitivity and specificity. While the signal from a labeled cancer cell cluster increases with the number of tumor cells, $n_{cells}$, antibodies per cell $a_{bound}$, and illumination intensity $L_{Ill}$, the dominant factor is the optical loss of radially divergent light over the imager-cell separation, d. We minimize imager-cell separation, d by reducing the optical waveguide and filter 114 thickness, increasing the optical signal from a small tumor foci.

Background can be reduced by incorporating a low dark current CMOS process or CCD process for the imager. Improvements in optical filter 114 performance (and rejection of excitation light) reduce optical bleed-through. Fabrication in a CMOS process optimized for near-IR imaging further increases optical sensitivity (photodiode efficiency or responsivity). The increased optical signal decreases integration time, improving SNR through averaging multiple images. Circuit design techniques are incorporated to reduce noise.

To reduce background variation and improve background subtraction for accurate tumor detection we require "local" background measurements, near the tumor cluster, for accurate subtraction and edge detection (aiding cluster recognition), driving the need for spatial resolution below the millimeter-scale excision achievable by surgery.

FIG. 3A shows an overview of another exemplary embodiment of the system 1 relating to the use of the microlens array 120 and imager to collect and process the visual signal produced on the tumor bed. In this embodiment, the microlens array 120 redirects the light A, B, C cast on the imager at the individual lenses. Exemplary embodiments of the system utilize a three dimensional array of microfabricated fluorescent sensors to enable 180 degree imaging (best shown above in FIG. 3C) from the close proximity of the imaging probe. As is shown in FIGS. 3B-3C, in exemplary embodiments, these microfabricated lenses 120 and stencils 118 can be fabricated in large sheets or on a substrate such as a quartz and assembled in "wafers" 150. In order to focus light at a very small distance from the sensor surface (for example 100-300 µm), extremely small lenses are utilized. Each "microlens" 120A will focus the light below it directly onto a pixel above, creating an array of thousands of fluorescent microscopes that can simultaneously image the tumor bed below. In one embodiment, a plano-convex lens is used. In order to focus an object that is extremely close to a lens 120A, the Lensmaker's equation requires that the radius of the lens is:

$$R \cong f \times \left(\frac{n_1}{n_2} - 1\right) \quad (1)$$

where f is the focal length (in this case, distance to the tumor cell), and $$\frac{n_1}{n_2}$$

is the ratio of indices of refraction of the lens ($n_1$=1.5) to the sample (e.g. tissue $n_2$=1.37), thus making R≅f×0.11 for this example. Therefore, to have a focal length "f" of a few hundred microns (to account for any fluid and tissue between the tumor cells and the sensor surface, the radius of the lens must be roughly 1/10th f. The radius is depicted as R1 in the figures. The radius of curvature of the planar side (R2) is set to infinite to approximate a flat surface. "d" is the thickness of the lens. To image the entire surface, these lenses are fabricated in a periodic array. In the example shown, they are arranged in a hexagonally packed array, with a diameter of roughly 70 microns. Therefore, instead of one large lens, the system utilizes an array of microlenses. In this exemplary embodiment, the microlens arrays have a radius of about 35 um, although microlens arrays of various other sizes can also be utilized in other embodiments.

In various implementations, periodic arrays of microlenses like that shown in FIG. 3A result in an array of image recordings by the imager from individual foci. The microlens array creates a unique image: instead of a single image, a periodic array is generated (with each point in the array of light hitting the sensor at a different angle). However, in certain circumstances, the use of individual microlenses can create noise and/or blurring issues, as discussed further below.

As shown in FIG. 4, in certain embodiments, the imager 102 is fabricated to have one pixel under each microlens. To increase spatial resolution as well as reduce cross-talk and background, a novel method preferentially imaging light incident perpendicularly, while rejecting divergent light, by directly integrating an array of microfabricated angle-selective collimators, or micro-collimators, over the surface of a photodiode, is shown in FIG. 4. It is understood that these implementations are optically coupling each photodiode to the cells directly opposite it. This angle selectivity differentiates the cell signal from the surrounding background, blocking light indecent at angles from adjacent areas of tissue, reducing cross-talk that contributes to image blur and background, as shown in FIG. 4. Consequently, pixels can be sized to match the size of a focus of MRD, but smaller pixels can be used, allowing each pixel to integrate all the signal, while rejecting neighboring background, maximizing the signal to background ratio and increasing SNR. In the limit that collimators are selective for only light that is incident perpendicular to the array, nearly perfect spatial resolution can be obtained, but at the cost of blocking significant signal light. At intermediate collimator values, the majority of the signal can be imaged, while blocking a portion of the background from neighboring tissue. Therefore nano-grids are designed we seek an optimal tradeoff between spatial resolution and signal power received. We optimize the design using a figure of merit (FOM) defined as the product of spatial resolution (SpR), defined as the ability to distinguish to adjacent foci of cells and equal to $1/r_1$, as shown in FIG. 4 and signal-to-noise ratio (SNR).

FIGS. 5A-5D show the SpR, SNR, and FOM as a function of imager distance from the cells and angle-selectivity of the collimators. The FOM, SpR and SNR increase dramatically with a smaller separation between the imager and the tissue surface, reflecting our goal to minimize this separation. The maximal FOM occurs at a collimator value of 0.8, close to our current implementation of nano-grids 2.4 μm wide and 6.8 μm tall. At the optimum collimator selectivity, decreasing the photosensitive surface to cell separation from 500-600 μm (current prototype) to 110 μm (anticipated) will increase the SNR and SpR by a factor of 14 and 7, respectively. Further enhancement of signal (and signal to noise), spatial resolution, and consequently the FOM, can be obtained by: decreasing cell to imager distance d; increasing excitation light intensity; incorporating micro-collimators block background light from non-specific binding and removing autofluorescence with an optical filter 114 using a new CMOS process with low dark current, high responsivity and low noise circuit design.

Reduction of the imager to tissue separation of <50 μm will achieve single-cell sensitivity.

FIGS. 6A-6G and 7 depict an alternative approach to system angle selectivity: an angle selective imager with nano-gratings. By utilizing wiring available on an integrated circuit imager 102, the system can further comprise a grating 150 further comprising small "cylinders" 152 disposed adjacent to the array. In embodiments utilizing this approach, the grating 150 is microfabricated directly on the imager 102 itself. FIGS. 6A-6G and 7 depict one embodiment of an angle selective imager using a complementary metal oxide semiconductor process ("CMOS"). In further embodiments, smaller scale geometric arrangements can be constructed. In embodiments utilizing this technique, the thickness of the "micro"-grating was reduced or eliminated, allowing the sensor to be placed closer to the surface of the tumor bed, thereby improving the signal. The aperture of the nano-grids should be greater than the wavelength of light used to avoid diffraction. The spacing of the grids is also determined by the fabrication process. In the embodiment shown, a CMOS process is used, and the metal interconnects are used to fabricate the gratings. In still further embodiments, other processes, such as a low-dark current photodiode, charge-coupled device ("CCD"), or PIN diodes can be used. Nano-gratings can therefore utilize the metal interconnect layers inherent in the CMOS or CCD fabrication processes.

Greater pixel densities are possible and the greater the pixel density the higher the resolution. For purposes of illustration, cylinders 2.4 microns wide and 6.8 microns tall have been used in certain embodiments, though other sizes and shapes are possible. In these embodiments of the system, the cylinders only allow light that is substantially perpendicular to the surface to pass through. In the experiment, a custom microfabricated 2.5 mm×2.5 mm angle selective imager having 180 nm features and 1024 pixels was utilized. In this embodiment, each pixel corresponded to the size of a microlens. Other configurations are of course possible, as would be apparent to one of skill in the art. Using this approach, the image was taken from a variety of angles (ranging from +/−45 degrees) and the results were recorded (FIG. 12B). As would be apparent to one of skill in the art, various sizes and arrangements can be utilized. As is apparent from this study, the grating successfully prevents incident light from passing to the pixels.

In other embodiments, microlenses are not used and angle selective imaging alone is responsible for spatial resolution. FIGS. 6D-6G show the angle selectivity as implemented on a 32×32 pixel array, with collimators 2.4 um×6.8 um high, arrayed over the photodiode. This approach has also been implemented on a larger array (discussed in relation to FIG. 24A-D, above).

Wavelengths of light different form the fluorescent or luminescent emission wavelength of the molecular label are eliminated by an optical filter 114. In certain embodiments, the filter 114 is a multi-layer interference filter 114 pattered on a 500 um glass wafer substrate. In certain embodiments, the filter 114 is epoxied onto the imager 102. The filter 114 may also consist of material that blocks light at wavelengths different from the emission wavelength of the molecular label. In other embodiments the optical filter 114 is patterned directly on the image sensor.

A comparison of size, sensitivity and spatial resolution of four model systems—a fluorescent microscope, a miniaturized (single-lens) microscope, a CCD imager without nanogrids, and a custom CMOS prototype using a stencil pattern of the 1951 USAF resolution target over a layer of fluorescent particles (quantum dots) illuminated with a waveguide, demonstrates the tradeoffs between the imager size and resolution. The single lens imager represents a minimum sized imager using traditional optics with a sample to imager distance of 6 mm and resolution <25 µm. The optics-free approach proposed here is demonstrated placing a custom microfabricated optical filter 114 (Chroma) directly on a CCD imager (no micro-collimators) and on our custom CMOS imager with nano-collimators). A 125 µm×600 µm line of fluorescent particles is easily resolved (blue outline) in all approaches, but requires 10× less fluorescent particles using the CCD and CMOS imagers over the optical counterpart due to decreased distance to the fluorescent sample. In our current implementation, we achieve a minimum detectable signal of 0.15 pW per pixel or 250 photons/pmt/sec capable of imaging a fluorescent spot with 10,000 antibodies/pmt (measuring 125 µm×600 µm, equivalent to 750 cells with 125 µm resolution.

Certain examples demonstrate one potential implementation of the circuit design for the photodetector, but others are possible, as would be apparent to one skilled in the art. In one embodiment the imaging device, comprising a 55 µm pitch, 80×36 pixel array, image sensor. The chip was fabricated in a standard 0.18 µm 1.8V/5V technology. A 500 µm-thick quartz wafer with a 10 µm wavelength selective coating is epoxied to the chip. Light at 450 nm wavelength is introduced from the side to illuminate the tissue. The filter 114 rejects direct illumination from the light source, preventing the photodiodes from saturating. The image is read out row-wise and digitized with an off-chip ADC (analog to digital converter) for further processing. ADCs can be integrated directly on chip.

FIGS. 24B-C depicts the angle-selective grating of a single pixel 160, consisting of a 20×20 octagonally-packed array of 2.4 µm wide by 6.8 µm tall tube-like structures 151. Its purpose is to block light incident at large angles relative to the chip surface normal, as illustrated in the perspective view. The majority of the blocked light is background and carries no information. In this implementation, the grid covers the entire 44 µm by 44 µm photodiode. FIG. 24D further depicts an in-pixel amplifier 161 and in-pixel memory 163, which can be integrated into the pixel for use in the processing and storage of images.

Figure 23:
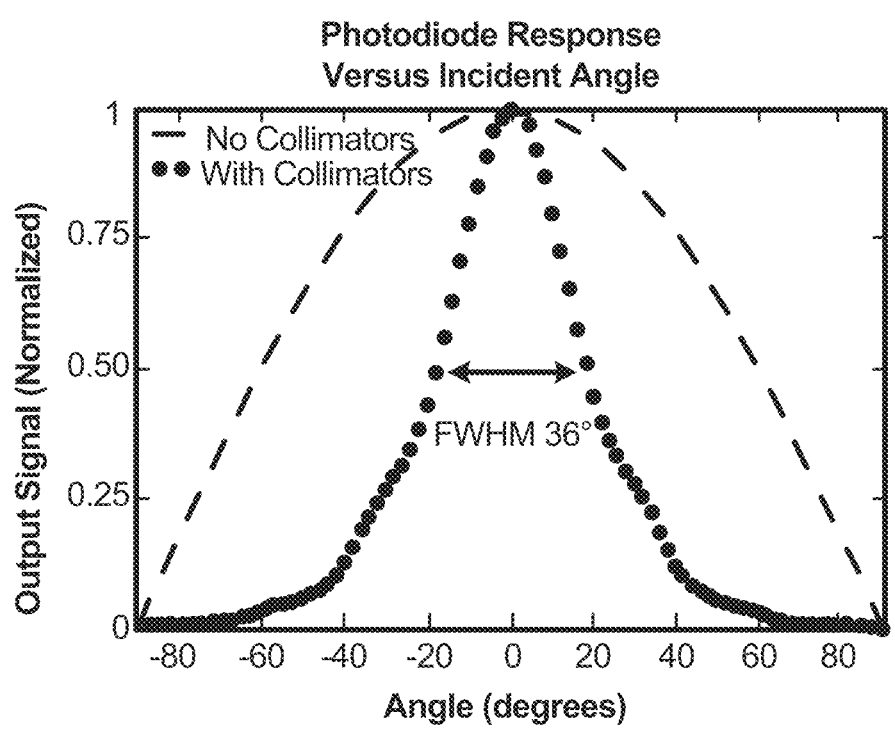
FIG. 23 depicts a graph of the photodiode response versus incident angle in implementations with and without collimators.

FIG. 23 shows the measured pixel response versus angle. The grating reduces the full width at half maximum (FWHM) from ±60° to ±18°, with only a 3.5 dB optical power insertion loss. This translates into a 14 dB boost in signal-to-background ratio when imaging a 3D cluster of 200 cancer cells in the AOV of a pixel, 500 µm away from the chip surface. Overlap in the AOV of adjacent pixels ensures that cell clusters at pixel boundaries are not missed. Readout circuits are placed in 11 µm wide channels surrounding each photodiode, resulting in a 28% fill-factor.

FIGS. 28A-L show implementations of the pixel circuit diagram consisting of a capacitive transimpedance amplifier (CTIA) 200 formed by M1-M4 with 50 nA bias current. An 11 fF metal-oxide-metal lateral flux capacitor, $C_{int}$, is used for integration. The pixel sensitivity is 8.2V/s per pW of incident light. The noise is shot noise dominated with a maximum RMS value of 6.3 mV. Reset takes 200 µs and after integration, the entire array can be read out in 1.3 ms, allowing real-time operation.

Figure 28A:
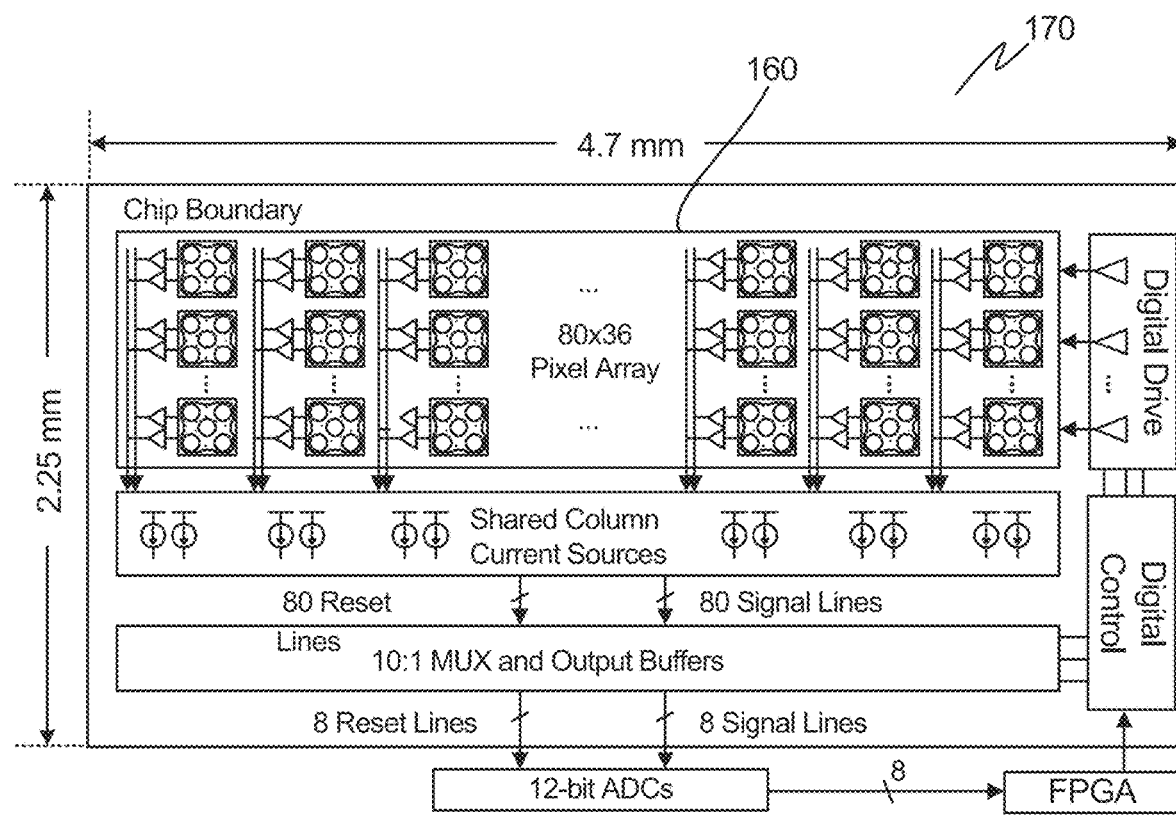
FIG. 28A is a block diagram of a chip, according to one implementation.
Figure 28B:
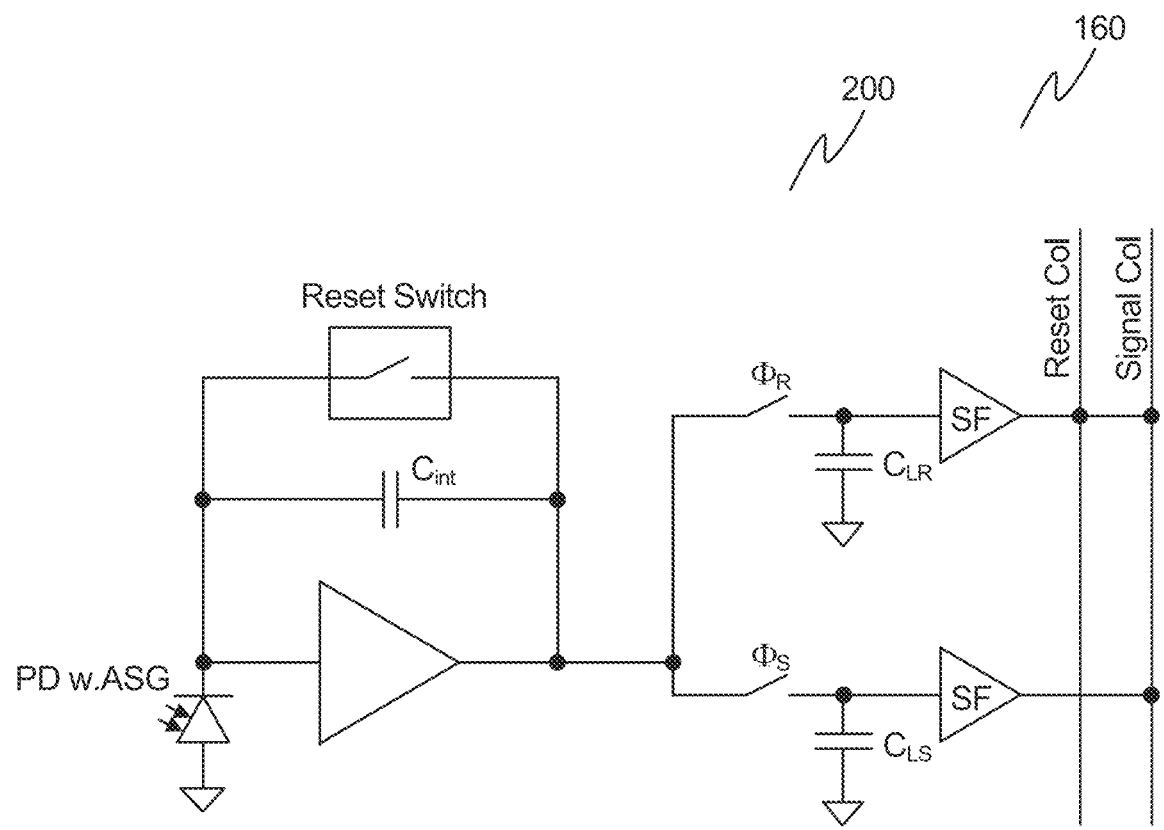
FIG. 28B depicts a block diagram example of pixel architecture, according to one implementation.
Figure 28C:
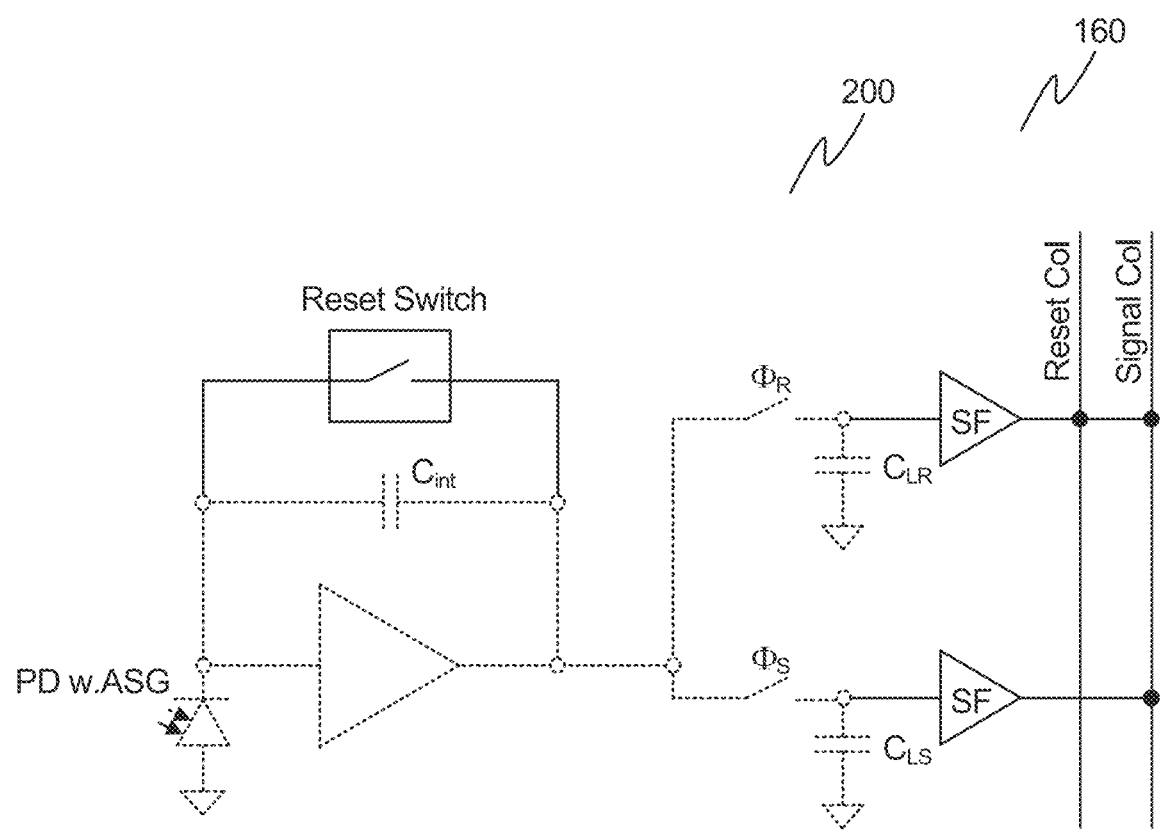
FIG. 28C depicts a block diagram example of pixel architecture, according to another implementation.
Figure 28D:
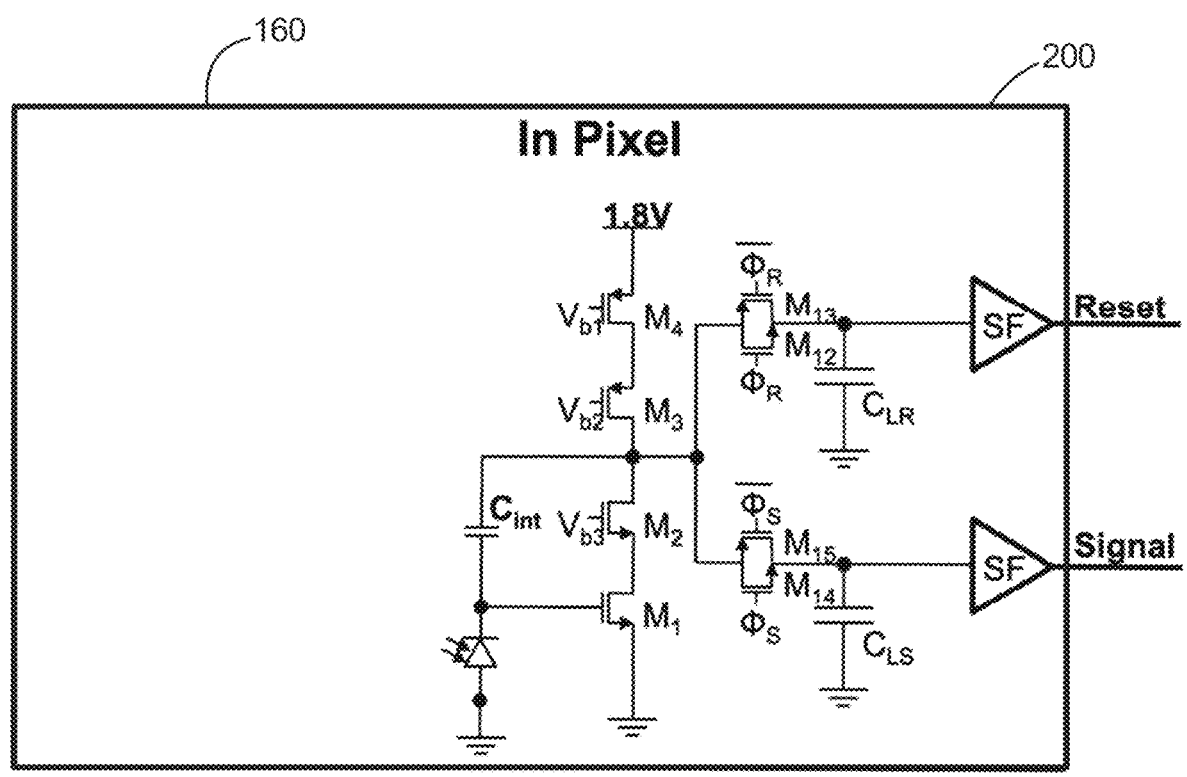
FIG. 28D depicts a block diagram example of a cascade amplifier, according to one implementation.
Figure 28E:
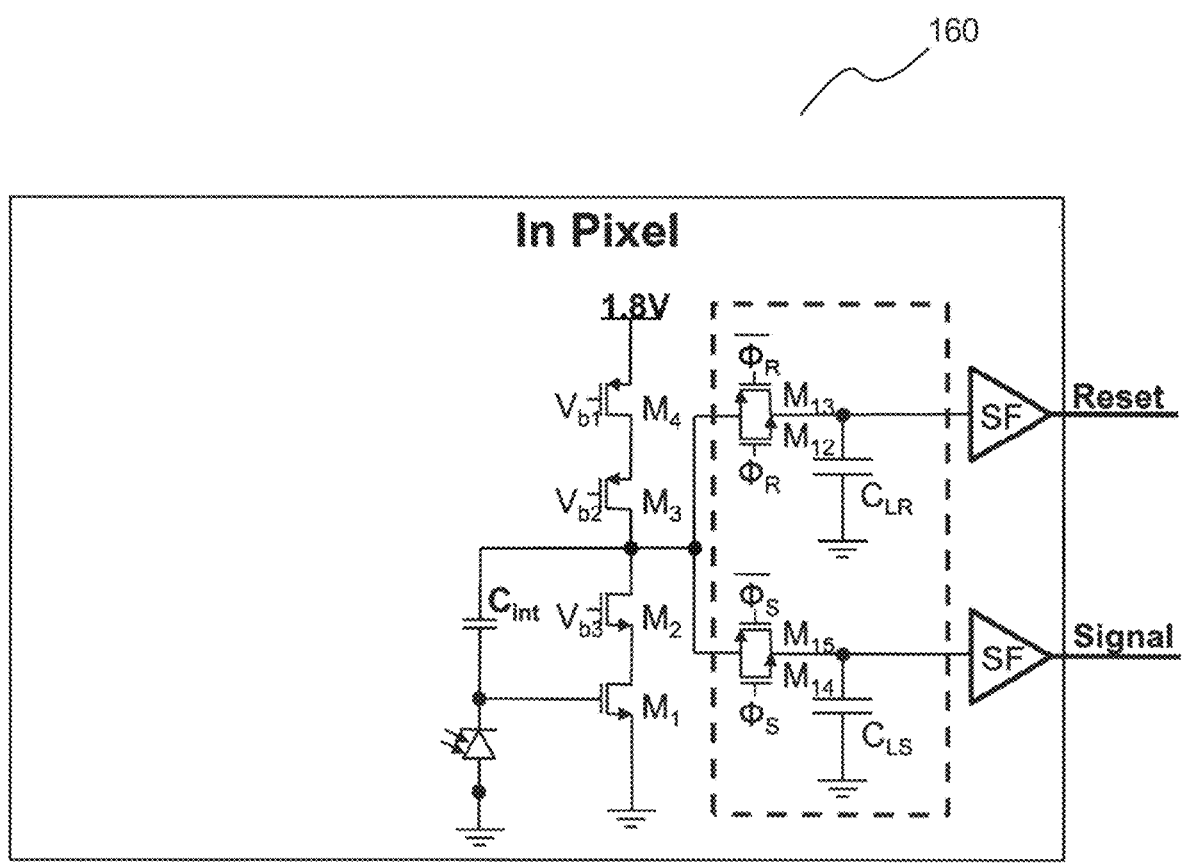
FIG. 28E depicts a block diagram example utilizing correlated double sampling, according to one implementation.
Figure 28F:
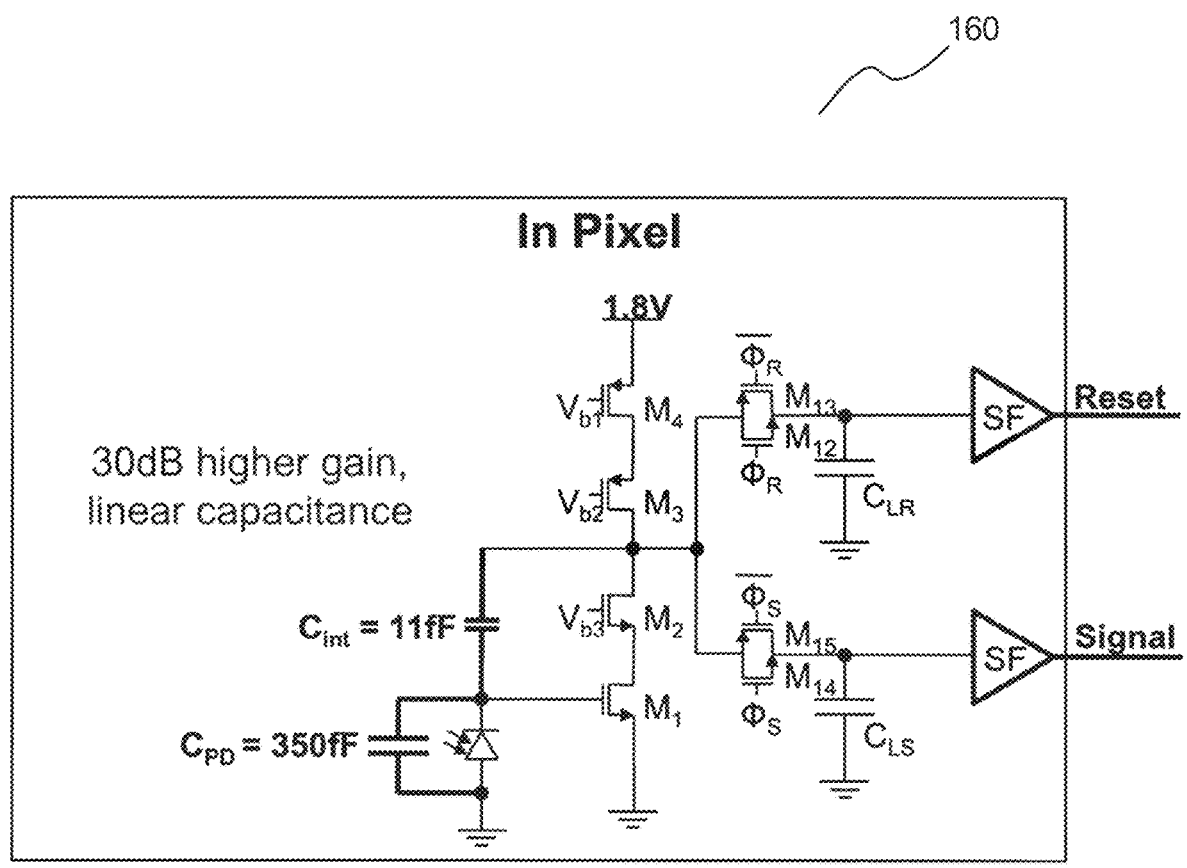
FIG. 28F depicts a block diagram example showing an integration capacitor, according to one implementation.
Figure 28G:
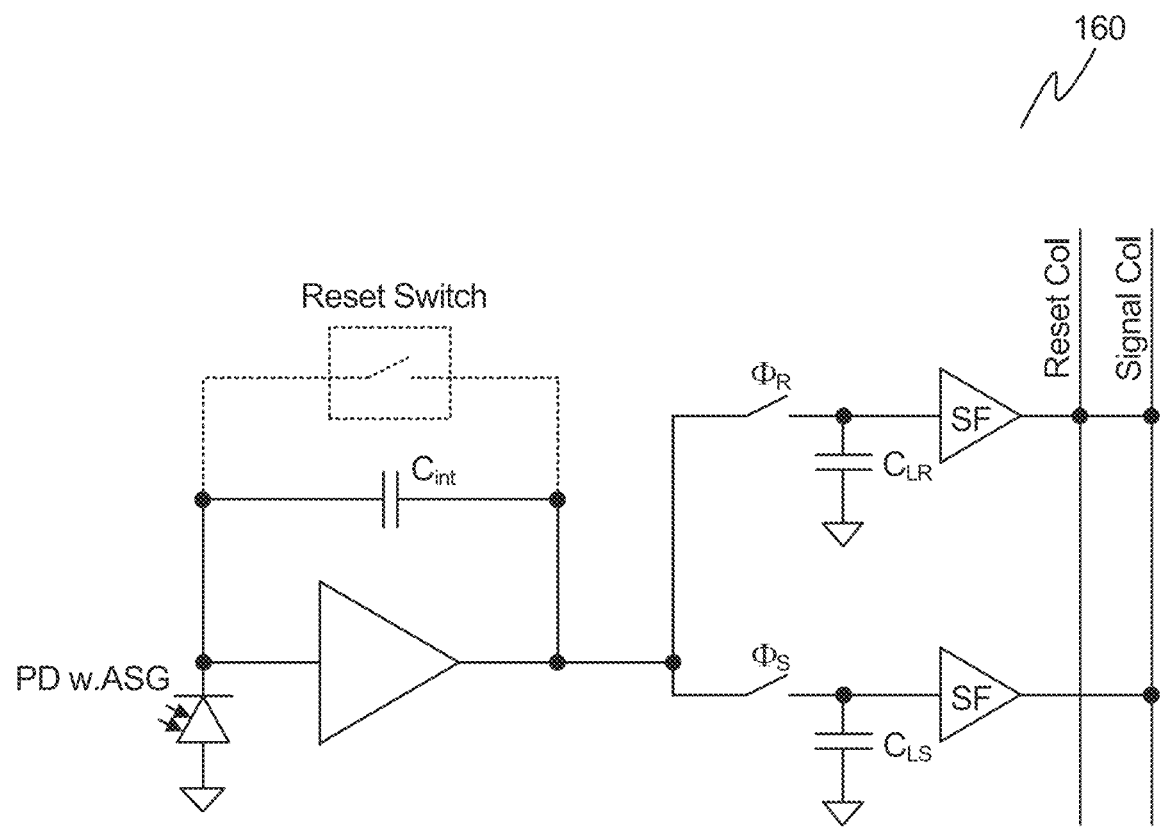
FIG. 28G depicts a block diagram example of pixel architecture, according to yet another implementation.
Figure 28H:
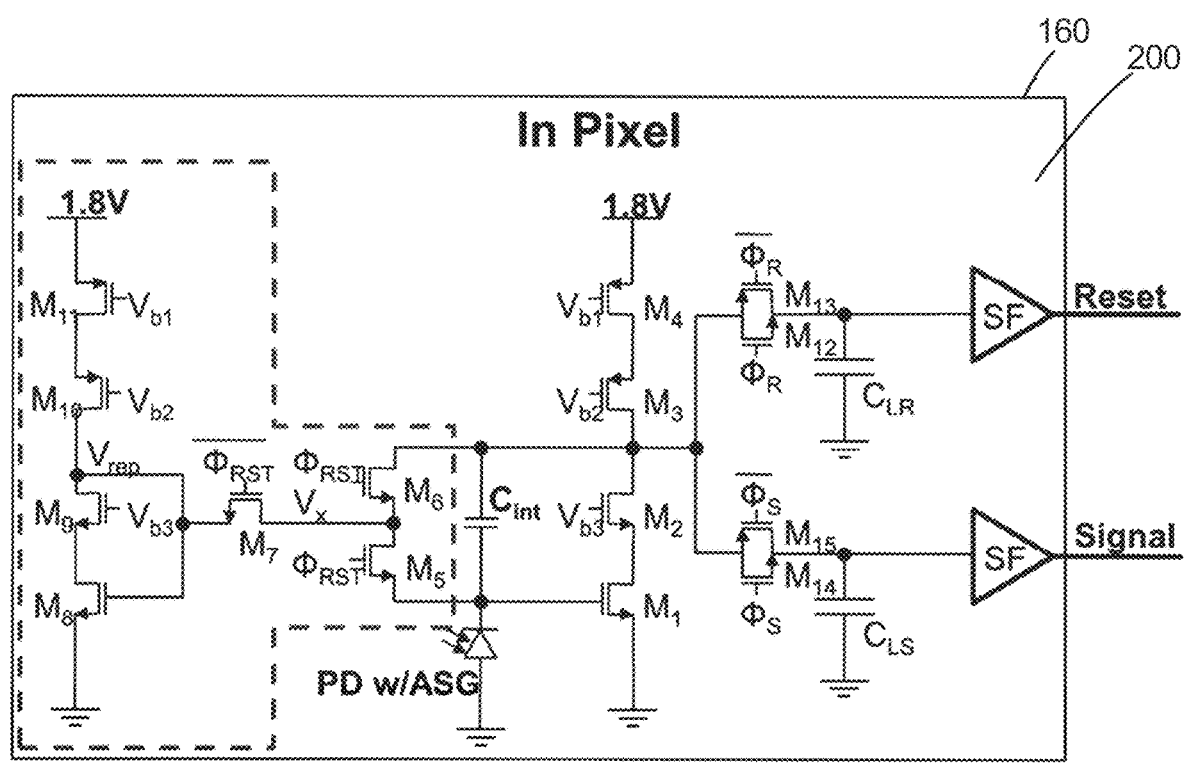
FIG. 28H depicts a block diagram example showing a replica reset amplifier, according to one implementation.
Figure 28I:
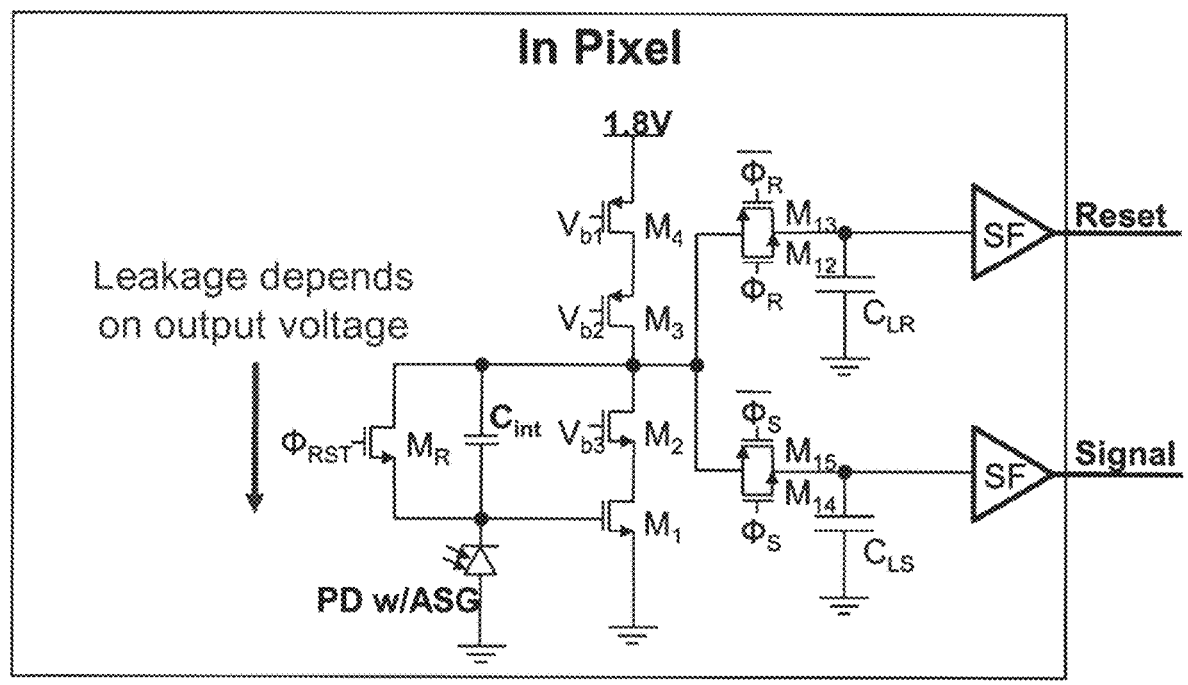
FIG. 28I depicts a block diagram example having a single reset switch, according to one implementation.
Figure 28J:
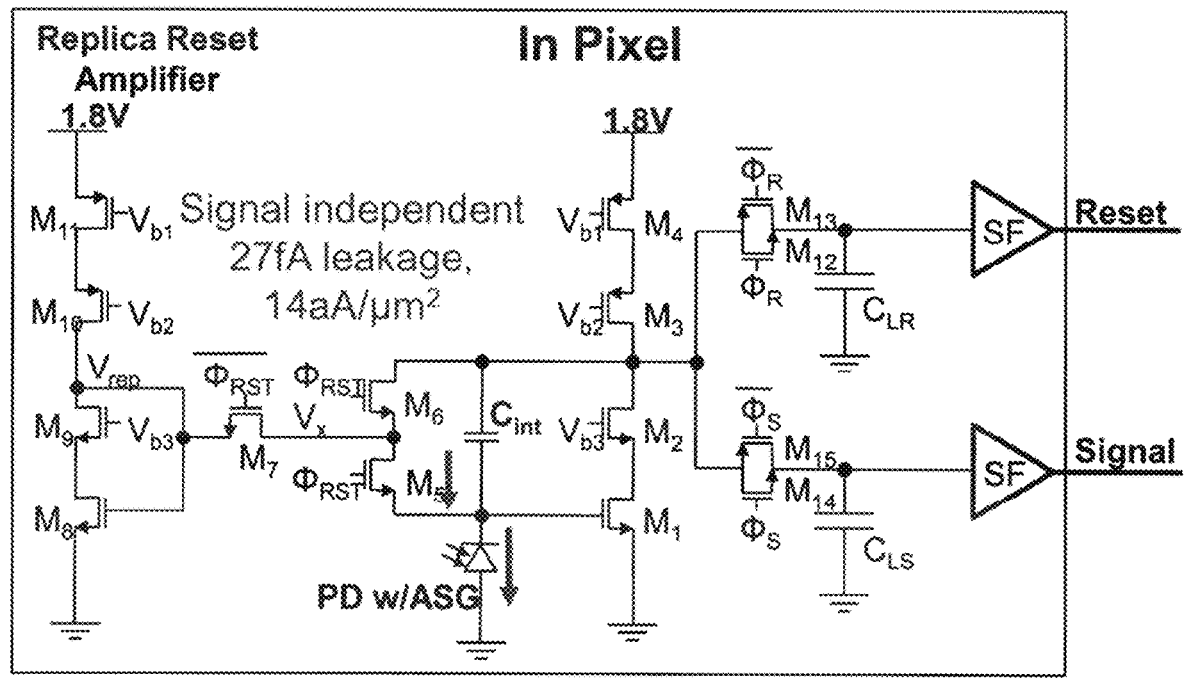
FIG. 28J depicts a block diagram example having a three transistor reset switch, according to one implementation.
Figure 28K:
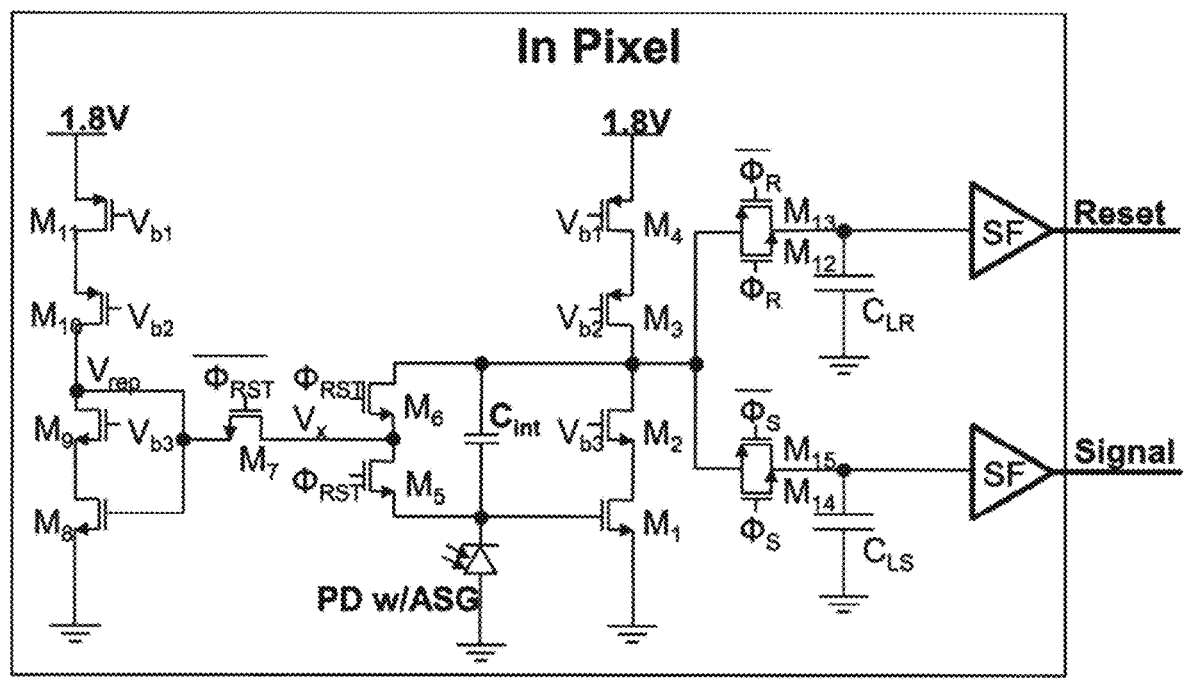
FIG. 28K depicts a block diagram example of a complete pixel, according to one implementation.
Figure 28L:
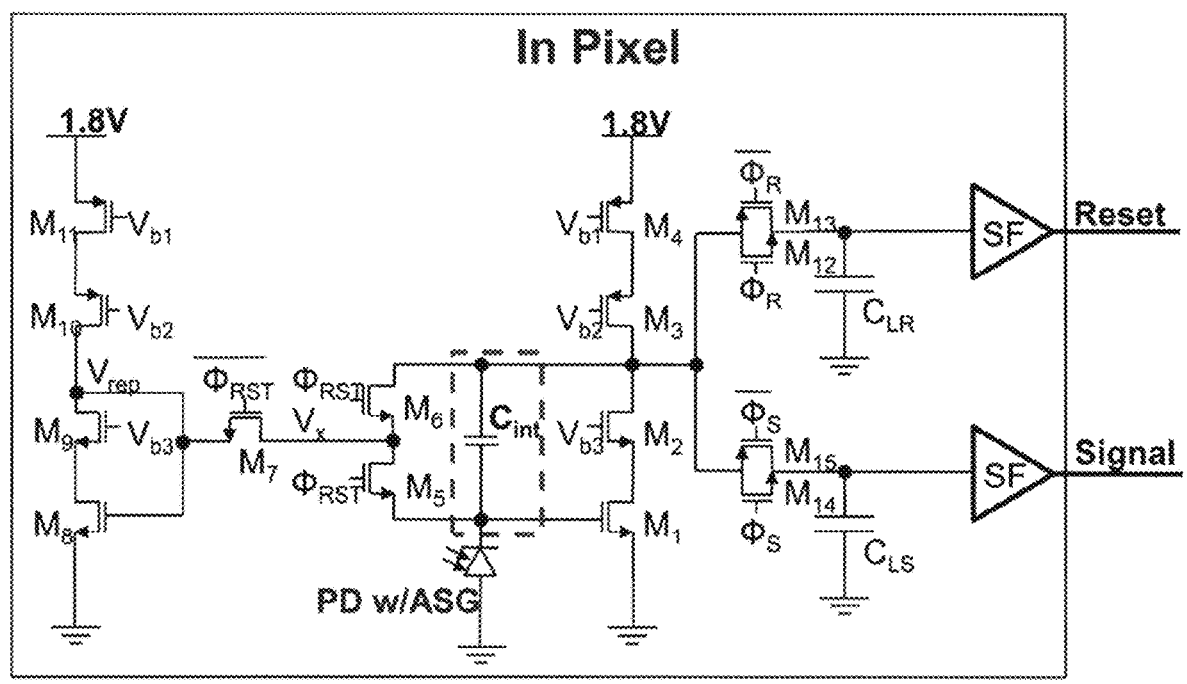
FIG. 28L depicts a block diagram example of a complete pixel, according to another implementation.

The imaging chip 170 shown in FIG. 28A is an 80×36 angle-selective pixel array that is read out row wise, buffered off chip and digitized. We use an FPGA to control the chip and also facilitate data transfer in real-time to a PC. The whole chip is 4.7 mm×2.25 mm. This is a global shutter readout, to allow more easy synchronization with an external light source. This allows some extra imaging methods to be used, such as exposing with multiple wavelengths of light, called spectral unmixing, which allows you to obtain some extra information.

FIG. 28B-F are block diagrams of a pixel 160, and integration capacitor, according to various embodiments. These embodiments feature a capacitive transimpedance amplifier architecture, where the light from the photodiode is integrated on an a separate integration capacitor, not its own capacitance. Two samples are taken, one directly after reset ends and stored on CLR, and a second after integration is completed, and stored on CLS. The main amplifier runs on a 1.8V supply, but these two samples are readout onto simple 5V source-follower column buffers, which allowed us to increase the dynamic range to about 1V (from 0.6V) without extra circuit overhead. The main amplifier only consumes about 50 nA of current in each pixel. In these implementations, the photodiode is covered in an angle-selective grating as described previously. However, this implementation includes a replica reset amplifier inside every pixel along with a 3T reset switch for leakage current minimization. If a single switch is used for reset across Cint, then once is is opened during integration, there will be a leakage current across it. Additionally, this leakage current will depend on the output signal level, causing a signal-dependent leakage that cannot be easily calibrated out. With a 3T reset and a replica bias amplifier, the voltage across M5 is minimized, and additionally will not change during integration, so there will be no signal-dependent effect.

Figure 25A:
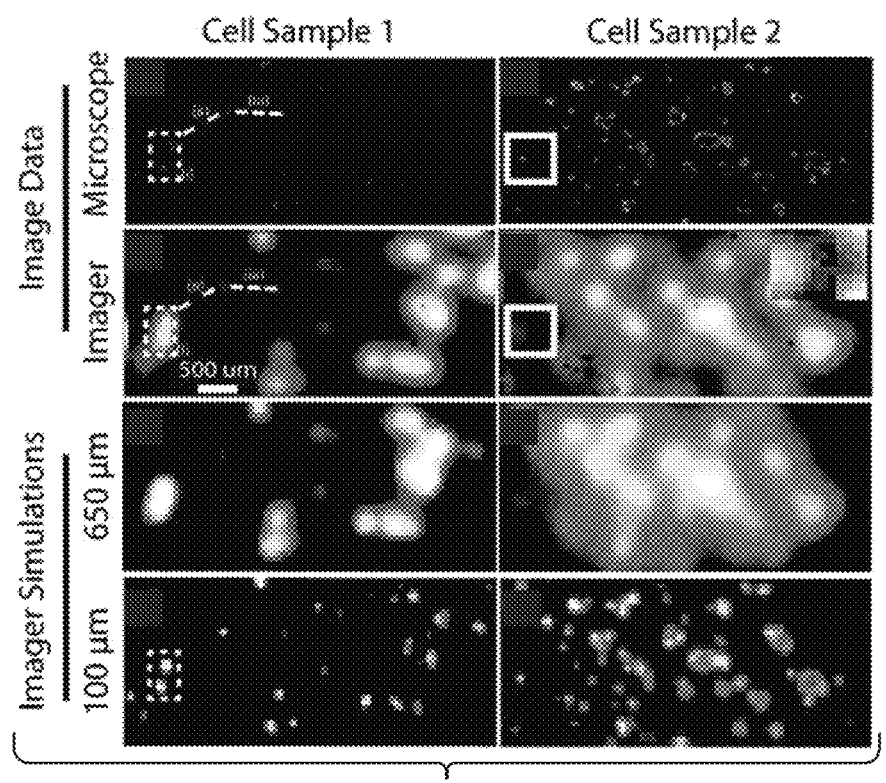
FIG. 25A two example cell cultures of observed with image data (microscope and imager), and via imager simulations at 100 μm and 650 μm.
Figure 25B:
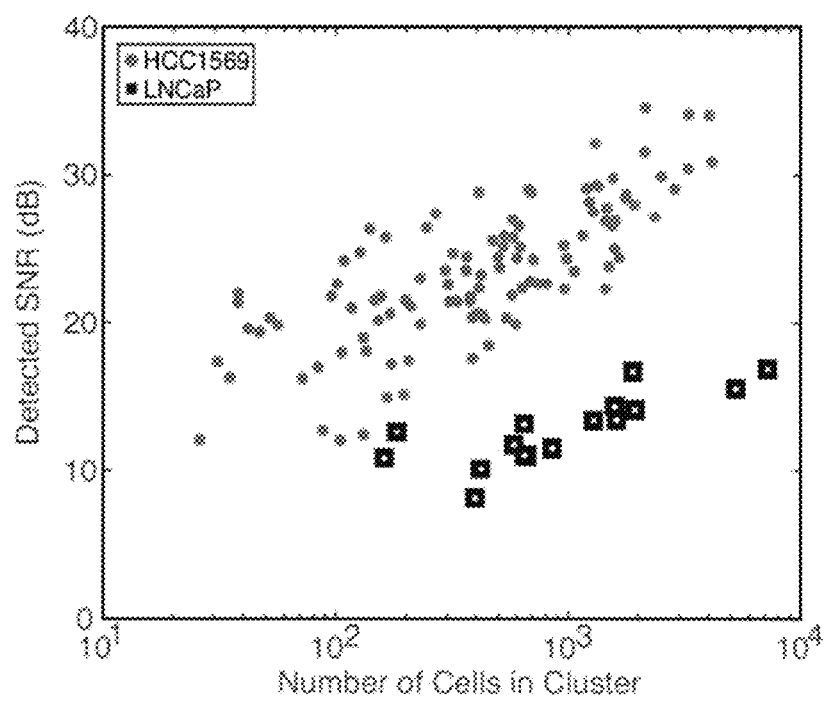
FIG. 25B plots the detected SNR for HCC1569 and LNCAP cells.
Figure 26:
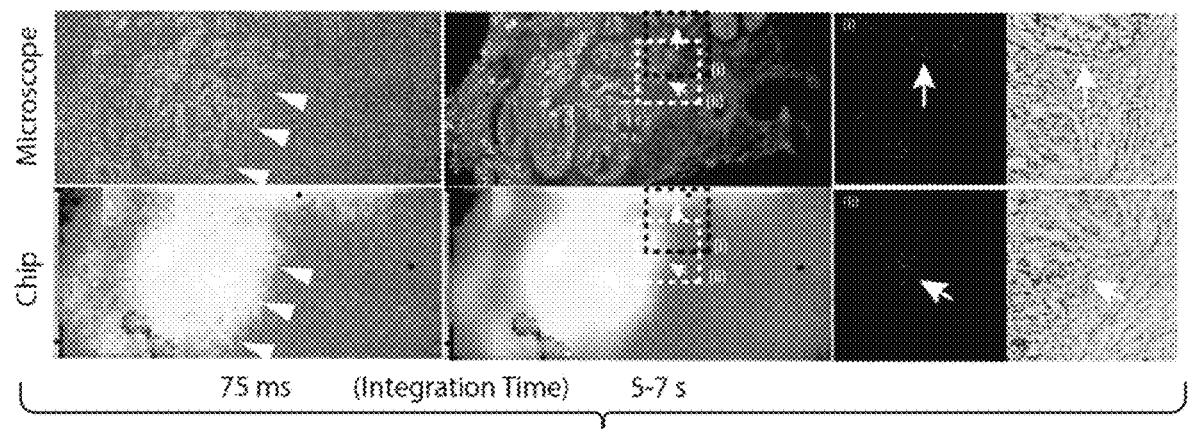
FIG. 26 depicts additional images of the tissue via microscope and chip showing integration time.
Figure 27A:
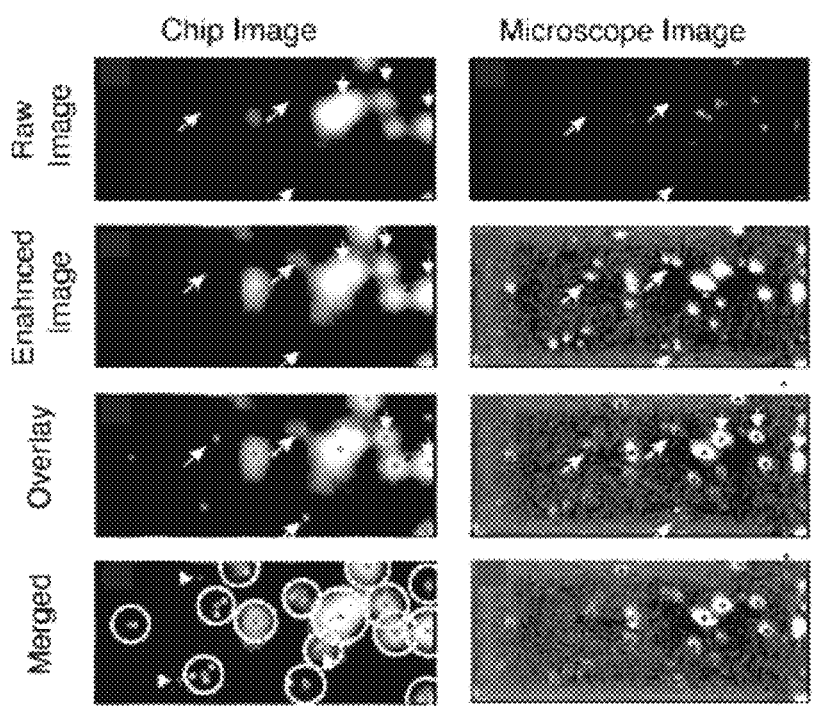
FIG. 27A shows imager and microscope images of cells depicting the raw image, the enhanced image, the overlay and the merged versions.
Figure 27B:
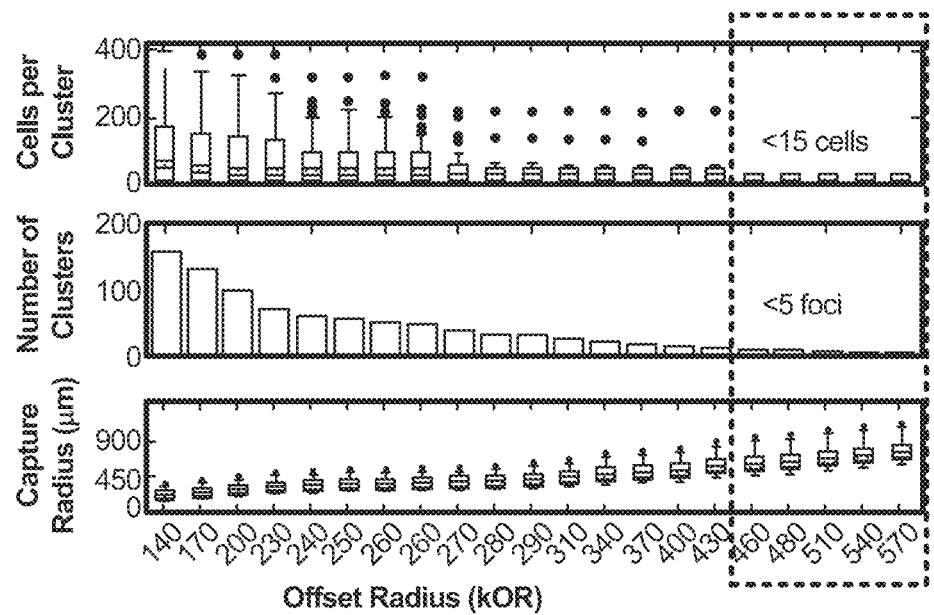
FIG. 27B depicts the characteristics of missed (false negative) foci, plotting cells per cluster, number of clusters and capture radius over offset radius, according to the implementation of FIG. 27A.
Figure 27C:
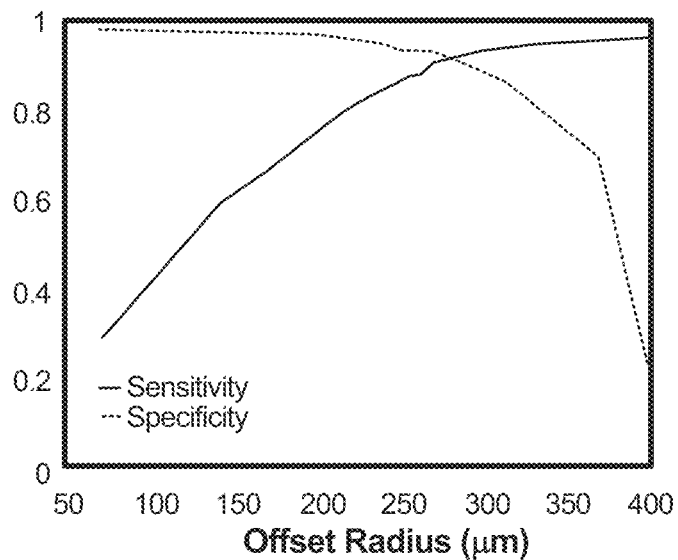
FIG. 27C depicts the sensitivity and specificity at various offset radii, according to the implementation of FIG. 27A-27B.

In certain examples, successful imaging of in vitro models of MRD has been achieved by imaging a 3D cell culture of SKBR3 grown in matrigel, labeled with Trastuzumab and secondarily labeled with anti-human quantum-dots (705 nm), visualizing 4 groups of MRD, each number between 200 and 1000 cells (as shown in FIG. 14). Larger scale images are seen in FIG. 25A and Images of Tissue are seen in FIG. 26. FIG. 25B shows sensitivity results for two example cell types, breast cancer cells (HCC1569) and prostate cells (LNCAP). SNR above 10 dB demonstrates a reliably detectable signal, indicating breast cancer cells detectable above 30 cells and prostate cells detectable above 100 cells. Further improvements in device performance (consisting of, but not limited to, increased illumination, increases pixel sensitivity, improved optical filter 114 and reduction of imager to cell spacing can reduce this to a single cell detection).

In implementations using luminescent or fluorescent particles, such as UCNPs, capable of absorbing light at wavelengths >1000 nm, in which the silicon imaging array is transparent to light, and illumination of the tumor bed 124 can be done directly through the imager 102. The fluorophore (for example, UCNPs) will up-convert the light re-emitting at the lower wavelength (i.e. ~800 nm or less) that can be detected by the photodiodes. Again, in these implementations, time gating imaging (as described above) can be used to eliminate background excitation light and autofluorescence. These implementations enable the elimination of the optical waveguide and optical filter 114, thereby substantially decreasing the cell to photodiode (shown at 102, 112) distance (all that would remain is the blood/fluid that overlies the tissue cavity), as well as decrease the physical imager thickness.

One such embodiment of the imager 102 in use employing time-gating imaging is shown above in reference to FIGS. 9A-C.

In certain implementations where UCNPs (which can absorb at 1100 nm or above) are used, and no optical waveguide or filter 114 is needed, the imager itself can be thinned to tens of microns and would represent the entire thickness of the device (no angle selective grids are needed). The use of UCNPs (absorbing in near infrared 800-1100 nm) enables time-gated imaging whereby the optical filter 114 can be eliminated, reducing device cost, decreasing complexity of fabrication, and thinning the imager 102. Certain implementations of the system 1 are able to enhance the signal to background ratio. Autofluorescence, both from the overlying thin layer of blood and the tissue itself, poses a major challenge to in vivo fluorescent imaging by significantly increasing the background potentially masking the small fluorescent signal from the labeled MRD. Further complicating imaging, the tissue surface profile and blood can vary significantly, resulting in heterogeneity in autofluorescence and precluding a single background or calibration measurement for global subtraction.

Therefore, a method is needed to determine both the background and the signal at each point in the tumor bed. Accordingly, certain implementations, like that shown in FIG. 10A, utilize spectral un-mixing imaging wherein both the fluorescent signal and autofluorescence at each point by rapidly alternating the excitation light, leveraging the fact that the fluorophore has a sharp absorption peak (dashed-bold), whereas the autofluorescence spectra (dash-dot) is slowly varying, and does not appreciably change with small variations in excitation light wavelength ($\Delta\lambda$). Illuminating at $\lambda 0$. excites both fluorescently labeled cell light (shaded) and the autofluorescence (dash-dot), imaged through the excitation filter 114. The excitation light is changed to a $\lambda 0$-$\Delta\lambda$ outside of the fluorophore absorption spectra but where the auto-fluorescent emission is largely unchanged, imaging only the background ($\Delta\lambda \ll \lambda 0$). To further reduce the small variation in the autofluorescent spectra, we can also excite by $\lambda 0 + \Delta\lambda$, averaging the output with $\lambda 0 - \Delta\lambda$, for more accurate background subtraction. Calibration sequences can also be performed using neighboring pixels with lower or absent tumor to establish the local background signal. By utilizing rapidly switching ($10^\wedge$-6-$10^\wedge$-2 seconds) LEDs or laser diodes, several images are taken at different wavelengths while over the same area of tissue. For a scalpel or probe moving at 1 mm/sec, only a 10 μm shift occurs during an image acquisition time of 10 ms; this imaging speed is possible with a CMOS imaging platform, as described below in relation to FIGS. 13-18.

Figure 10A:
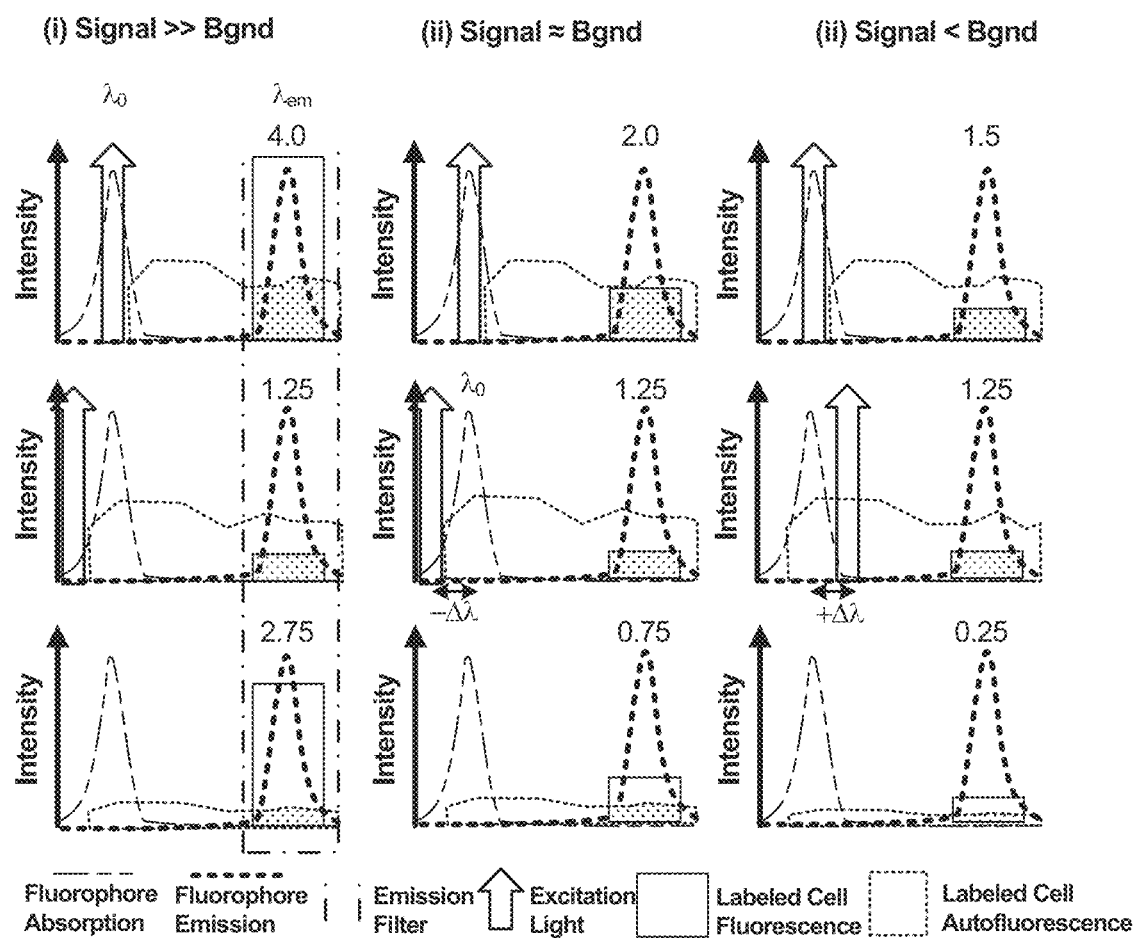
FIG. 10A depicts an illustration of various implementations of the imaging system utilizing spectral un-mixing imaging.
Figure 10B:
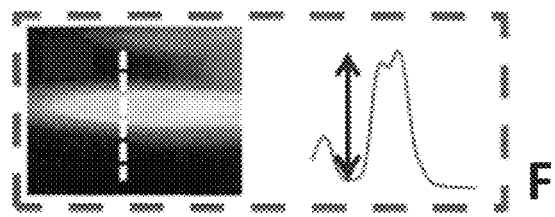
FIG. 10B shows an image of a cell in 3D culture, and a plot of the corresponding fluorescent FITC signal intensity along the dashed line.
Figure 10C:
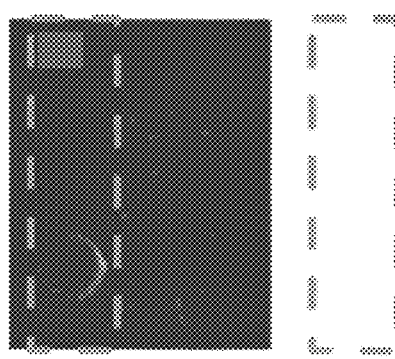
FIG. 10O depicts the cell isolated for depiction in FIG. 10B.
FIG. 10D shows the image with overlaid with an artificial, heterogeneous, autofluorescent layer, according to one implementation.
FIG. 10E depicts the background imaged by exciting with 400 nm (DAPI), but imaging through 515 nm (FITC).
FIG. 10F shows the increase in SBR with background subtraction, according to one implementation.
Figure 10D:
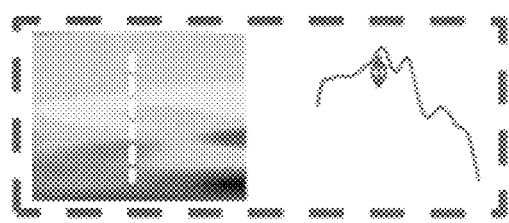
Figure 10E:
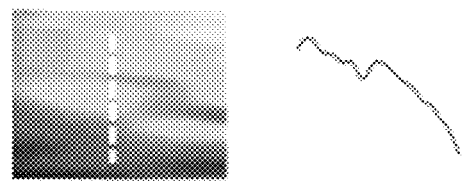
Figure 10F:
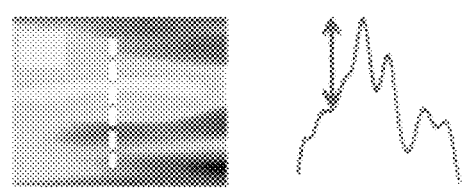

To demonstrate this technique, we image SKBR3 cells labeled with Trastuzumab and anti-Human FITC using FITC and DAPI filter 114s, FIG. 10B shows the cell highlighted in 10C, along with a plot of fluorescent intensity along the white dashed line. FIG. 10D shows the image with overlaid with an artificial, heterogeneous, autofluorescent layer (yellow tape). The background (FIG. 10E) is obtained by exciting with 400 nm (DAPI), but imaging through 515 nm (FITC), and subtracting the two images increases the SBR by a factor of 2 (FIG. 10F). FIG. 10B is the intensity of a cell in 3D culture (FIG. 10C), with the corresponding FITC fluorescent magnitude along the dashed line plotted; (FIG. 10D) shows the effect of adding auto-fluorescent background, washing out the signal; (FIG. 10E) is the background from excitation with 400 nm light, representing the autofluorescence, and (FIG. 10F) shows increase in SBR with background subtraction.

Exemplary embodiments use Tra-IR800CW (×0 778 nm), and significantly improve background subtraction by using multiple wavelengths of excitation light, averaging out variations in the autofluorescent spectra. To generate ideal wavelengths a broad-emission LED can be used with an optical filter 114 or lasers at specified wavelengths. Residual Tra-IR800CW fluorescence at $\lambda 0 +/- \Delta\lambda$ is calibrated out using ex vivo spectra measurement.

It is understood that certain implementations of the system apply to other cancers. For example, humanized anti β1-integrin antibody (OS2966 of the Park Lab and OncoSynergy), was injected at 20 mg/kg into nude mice implanted with HCC1569 and MDA-MB-231, specifically binding to ER-/PR-/HER2-breast tumors over HER2-overexpressing tumors, extending applicability of other breast cancer subtypes. It is understood that various alternative antibodies can be utilized in further assays and implementations of the system 1, as would be apparent to one of skill in the art.

Returning to the operation of various implementations of the imager 102 and the illumination strategies that can be utilized, in FIG. 11A-B, a fiber-optic bundle (gray arrow) has been fabricated that terminates into a linear array of 12 400-μm fibers (white arrow). These fibers guide light into a thin quartz planar waveguide, 500 μm thick. This 500 μm waveguide represents a significant contribution in the imager 102 to tissue separation. In this implementation, a 100 μm thick waveguide was fabricated by dicing quartz wafers thinned to 100 μm. In various implementations, errors associated with non-uniform illumination of the tumor bed—such as from light entering via discrete fibers and losses along the waveguide—will be calibrated out by also illuminating with light at the emission wavelength, thereby passing through the optical filter 114 prior to each image. These implementations are therefore allow visualizing the input light field. In alternate embodiments, illumination is achieved by directly affix LEDs to the waveguide edge. In alternate embodiments, when optical tags (such as UCNPs) that can absorb in the infrared range are used, light can be directly passed through the imager itself. Other implementations for illumination include attaching LEDs to the waveguide directly.

Identifying the fluorescent signal of the labeled cells requires distinguishing the fluorescent emitted light from the excitation light and autofluorescence, necessitating an optical filter 114 that has out-of-band rejection of $10^5$ or greater. These filter 114s are commercially available through Chroma, and manufactured using microfabricated thin films. The filter 114 is composed of multiple thin-film layers combining to a total of ~10 μm fabricated on a 500 μm fused silica substrate for handling (discussed above in relation to FIGS. 6A-G).

Figure 21A:
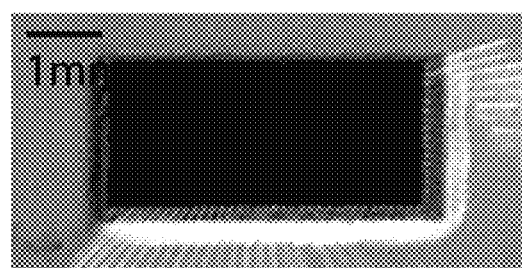
FIG. 21A is a top view of a CMOS contact imager, according to one embodiment.
Figure 21B:
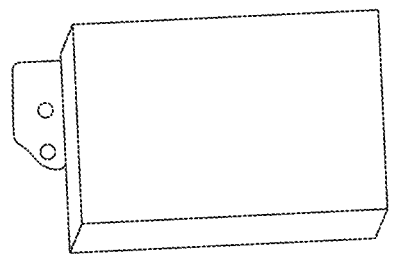
FIG. 21B is the CMOS imager of FIG. 21A with a filter affixed thereto.
Figure 22:
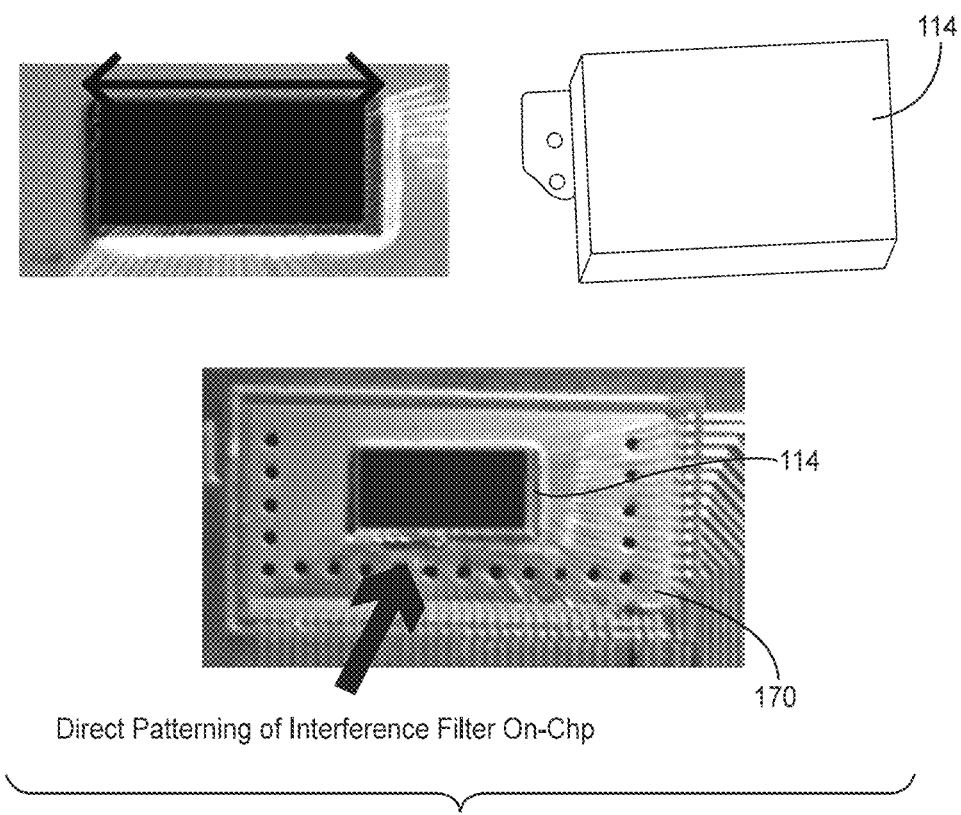
FIG. 22 depicts several top views of the direct patterning of the filter onto the chip, according to several embodiments.

Examples of the imager and filter are shown in FIG. 22. Fabricated filter 114s are diced into dilets and epoxied onto the chip (FIGS. 21A-B). FIG. 22 (bottom) demonstrates direct fabrication of a filter 114 onto the imager chip 170.

As shown in FIG. 12A-B and discussed above in relation to FIG. 6G, fluorescence detection of 10,000 fluorescent antibodies/μm2 with a spatial resolution of at least 125 μm can be demonstrated with interference filters 114 on a 500 μm fused silica substrate epoxied to a CMOS imager. Various implementations can also image a group of ~200-1000 cells in a 3D model of breast cancer. We further improve the sensitivity and form-factor of our prototype by improving the circuit design to reduce noise, fabricating the imager in a optimized photosensitive CMOS process (such as that via the XFab Foundry, Tex., USA) with a highly photosensitive (high responsivity) pinned photodiode with minimal dark current, increasing signal and decreasing background and noise, and reducing the total thickness of our imager 102 by thinning the CMOS chip 170 to <100 μm. These and similar photosensitive CMOS processes make use of a larger depletion region (which can be achieved with a PIN photodiode).

In an implementation using a 32×32 pixel array fabricated in a standard 0.18 um CMOS process (FIGS. 6A-6B) where each pixel element consists of a 40×40 μm n-well/p-substrate photodiode with a single on-chip buffer to minimize power consumption. In our current implementation, we achieve a minimum detectable signal of 0.15 pW per pixel or 250 photons/μm2/sec (FIG. 6E), capable of imaging a fluorescent spot with 10,000 antibodies/μm2 (the threshold established in Aim 1 HER2+ breast cancer cell detection) measuring 125 μm×600 μm, equivalent to 750 cells with 125 μm resolution. To further validate the imager, a 3D cell culture of SKBR3 grown in matrigel, labeled with Trastuzumab and secondarily labeled with anti-human quantum-dots (705 nm), demonstrating visualization of ~200 cells, was successfully imaged as shown in FIGS. 8A-C.

In one embodiment, the pixel 160 showing the photodiode 162 with surrounding circuitry 164; further embodiments can have a greater fill factor with more photodiode and smaller circuitry/transistors; or multiple smaller pixels. In various implementations the pixels 160 are arranged to spatially correspond with the microlens array, as would be apparent to one of skill in the art.

In certain implementations, the imager 102 can have pixels 160 with in-pixel memory to store a value or intensity from which to subtract from the next image. In-pixel memory allows rapid on-chip background subtraction to remove noise, offset, and autofluorescence, such as by modified spectral un-mixing.

In further implementations, each pixel 160 has an in-pixel comparator, comparing the "new" value with the previous one, and outputting a digital signal. In certain implementations of the in-pixel comparator, these angle-selective structures fabricated in the metal layers of the CMOS process can also serve an electrical purpose. In certain implementations, the in-pixel comparator can be used as a storage capacitor for pre-computed threshold voltages. The integrated input signal can be compared to this threshold value using an in-pixel comparator that outputs a single digital bit indicating whether cancer is present over that pixel or not. These implementations allow the readout of all the pixels in the array to take place in a very short amount of time, as only a single digital bit must be read out as opposed to an analog signal.

In further implementations, a "global shutter" technique can be employed, wherein all pixels 160 are integrated during the same time period, which further enhances the ability to perform time-gated imagining. It is understood that a global electronic shutter starts and stops the integration of input light in every pixel 160 at the exact same instant. In this way, the information stored in each pixel (for example in-pixel memory) corresponds to the same time interval. A global shutter is able to capture time-dependent signals that are only present for a short period of time (such as the fluorescence emission from up-converting nano-particles ("UCNPs"), that have a time-constant on the order of 10 s or 100 s of microseconds, as is described above). A rolling shutter is insufficient to capture the signal due to the limited speed of the readout circuitry.

Further improvements in circuit design will enable greater optical sensitivity and therefore a lower concentration of biological ligand to be used in vivo mitigating potential toxicity or cost associated with the biologic injection, and increase robustness against reduced SBR from background binding and fluorescent signal losses through overlying blood and fluid. Various implementations increase sensitivity by:

Increasing light sensitivity. Using a commercially available CMOS process optimized for optical sensing (such as the XFab 0.18 μm XS018) it is possible to use a pinned diode which, by virtue of its thicker light collecting region increases sensitivity to the emitted fluorescent light (in some instances by a factor of 5).

Decreasing background. Background signal both masks the faint tumor signal and contributes noise to the sensor. We proposed to significantly reduce this by using a pinned photodiodes coupled with a four-transistor (4T) architecture available commercial CMOS processes, such as the X-Fab XS018 process. This represents a significant improvement over our current CMOS process which has a dark current of roughly 0.1 fA/μm2, or 5000 photons/μm2/s (which is currently subtracted out during calibration).

Noise subtraction. Currently, pixels are read serial using a "rolling shutter", resulting in each pixel integrating during a slightly shifted time window. For noise cancelling techniques such as correlated double sampling, as well as the autofluorescent subtraction and illumination calibration techniques discussed above, it is possible to subtract images taken rapidly in sequence, removing noise and background. This requires all pixels to have exactly the same integration window ("global shutter"), enabled with the four-transistor architecture.

A faster imager: The increased sensitivity and lower noise will allow a reduction in integration time, allowing us to take 2-3 images during the 20 ms time window, alternating between autofluorescence/background signal and the tumor fluorescent signal. To further thin the physical form-factor of the device, the CMOS wafer itself can be thinned to less than 10 μm using standard microfabricated techniques; we will thin the CMOS silicon substrate to 100 μm to maintain structural and handling integrity.

Improved pixel-level circuit design techniques can also be introduced. In one implementation, a capacitive transimpedance amplifier (CTIA) frontend consisting of a gain stage with a capacitor in feedback can be used. This capacitor acts as the integration capacitor for the current that is generated in the photodiode. Since this capacitor can be chosen independently of the size of the photodiode in this architecture, it can be made significantly smaller than the photodiode capacitance. The input current generated in the photodiode will be the same if the same photodiode size is used, but due to the reduced capacitance, the voltage generated in the pixel will rise significantly faster, meaning that less time needs to be waited before the pixel capacitor has reached its full-scale value. Accordingly, for the same integration time, the noise introduced by the pixel source-follower amplifiers and the following circuitry appears smaller for a CTIA architecture in comparison to a convention 3T readout when input-referred and the same integration time is used. An additional benefit of the reduced integration capacitance is a reduction of the reset noise added when the reset switch is opened. This noise has power $v_{n,rst}^2 = kTC_{int}$, where k is the Boltzmann constant, T is temperature, and $C_{int}$ is the integration capacitance. Reducing the integration capacitance directly reduces the noise power. For example, a $C_{int}$ of 10 fF with a CTIA architecture will allow us to detect 175 cells cancer cells at with a target SNR with an integration time of only 2 ms when an input light intensity of 100 mW/cm$^2$ is applied on the surface of the tumor cavity and the imager is 400 µm away.

Furthermore, the CTIA architecture fixes the voltage across the photodiode, linearizing the response of the amplifier to different light intensities, removing the need to perform any gain calibration in post-processing. A further architectural improvement is two in-pixel storage capacitors that will allow both correlated double sampling that reduces flicker noise and cancels amplifier offsets, as well as enabling a global shutter. A global shutter ensures that the pixels are integrating for the exact same period of time. This enables the described multiple wavelength imaging technique, in which a second wavelength is used to excite to image the autofluorescence of the healthy tissue to calibrate for input light intensity and background variations. A global shutter allows the integration and readout times to be independently controlled, allowing a more efficient light-switching method to be used, where no pixels are not sitting idle as frequently.

When the integrated circuit imager is combined with a 100 µm waveguide, and 10 µm optical filter 114, the total thickness of the device will be about 210 µm.

Figure 13:
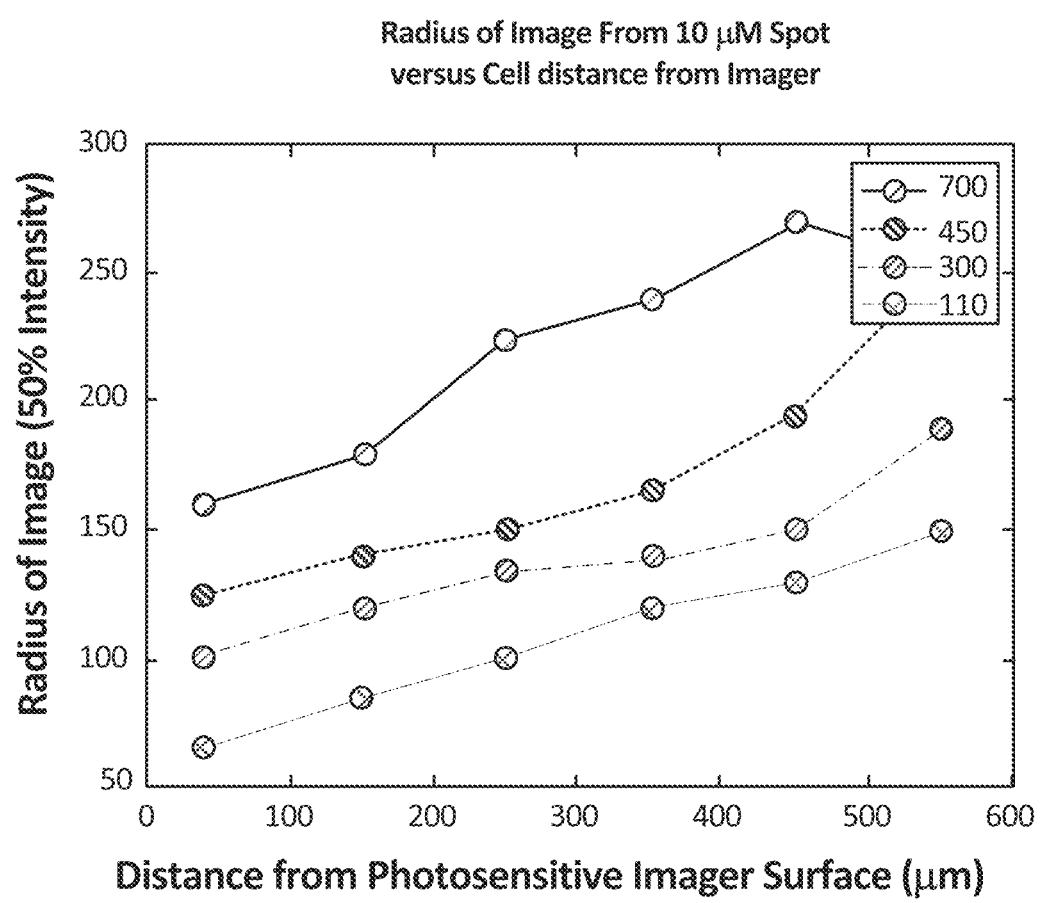
FIG. 13 is a graphical representation of the robustness, wherein the radius of the image increases as the distance from a photosensitive imager surface is increased, according to various implementations.

In FIG. 13, the effect of increasing thickness of fluid (x-axis) on the cell surface with imagers of varying thicknesses. The 700 µm trace closely represents an earlier model implementation (500 µm filter/waveguide+170 µm coverslip) when imaging cells in vitro, while the 100 µm trace represents an improved model implementation showing that the degradation in spatial resolution will be limited to a factor of 2 over 300 µm of variation in tissue surface profile.

It is understood that any of the embodiments discussed herein can be used in conjunction with, or in place of the various aspects of the remaining examples and embodiments.

In certain exemplary embodiments, and as a means of visualizing in a wider field of view, at least one imager may be mounted parallel to the fiber optic light guide such that the fiber optic light guide and waveguide are substantially in axis, rather than at an angle. For example, in FIGS. 14A-14D, the plane of the light source and waveform are in substantially the same orientation (as opposed to incorporating the reflection shown in FIGS. 15A-15D).

As is shown in FIGS. 15A-D, certain exemplary embodiments of the system are capable of guiding light along the imaging surface 122 by way of a light guide 110 in order to illuminate the tumor bed while the imaging surface 122 is placed directly on the tumor bed surface 124. To accomplish this and introduce versatility, exemplary embodiments use a remote light source which emits light through the light guide 110, through the waveguide 116, such that the light source can be positioned far from the operative field (not shown). These implementations allow the use of any wavelength or power, and do not place any size or shape restraints on the source, thus allowing for flexibility and cost savings.

Numerous light sources can be used. In various embodiments, the light source can consist of a laser, laser diode, light emitting diode ("LED"), or halogen or mercury arc lamp. Other sources are possible, as would be apparent to one of skill in the art. In one exemplary embodiment, the system utilizes a remote LED light source, which presents the advantages of being quickly turned on and off and having relatively high power. Other sources have various advantages that can be utilized to suit individual needs. Another advantage of having the LED remote or separate from the patient is that significant heat can be generated by the LED and LED power supply.

In these embodiments, an optical filter 114 can be placed in front of the remote LED light source to ensure that the wavelength of light is emitted in a narrow optical range (not shown). The LED directly couples to a fiber optic cable which is attached to the imaging probe (not shown). In certain embodiments, a commercially available LED that directly couples to a fiber optic cable is used (available, for example, from Thor Labs). The light is then guided into the tumor bed 124 by the waveguide 116.

FIGS. 15A-15D depict an exemplary implementation of the probe 100 comprising a light guide 110. FIG. 15A depicts an overview of the imaging probe 100 and light guide 110. FIGS. 15B-15C show front and side views, respectively, with FIG. 15D depicting a zoom schematic of one implementation of the light guide to diseased tissue 124. The waveguide 116 can consist of a planar structure as shown. Furthermore, an optical grating can be fabricated on the surface of the waveguide facing the tumor bed 124 to facilitate the escape of light towards the tumor bed. This grating may consist of microfabricated ridges or a roughing of the surface. The grating density may be increased at the distal end of the waveguide to compensate for the decreased intensity of light at the distal end by allowing more light to escape, maintaining a uniform illumination along the surface.

As is shown, in certain embodiments a light guide 110 is provided which is generally elongate and comprises a light transmitting core 132. In exemplary implementations, this can be a fiber optic core, though other materials may be used. Certain embodiments further comprise a reflector 128 which is configured to alter the course of light transmitted by way of the light guide so as to illuminate the desired disease tissue. In order to simultaneously capture information from several angles, or in certain embodiments to capture a 180 degree view of diseased tissue 124, certain implementations of the probe 100 further comprise a 3 dimensional arrangement of sensors (like that shown above in FIG. 2C). In these embodiments, in order to illuminate the side-facing imagers 102a similar fiber optic arrangement of a bundled fiber that terminates in a linear array of fibers can be used, without the 90 degree reflection (as is shown, for example, in FIG. 14D). In certain embodiments, the light can then be reflected 90 degrees as shown in FIG. 2D, though in other embodiments various other degrees of reflection can be utilized. That is, the angle of the light as it is directed into the waveguide can range from 0 to 180 degrees. In certain embodiments, the reflector 128 can be a prism or a mirrored reflective surface. In certain embodiments, the fiber optic bundle guides light into the tumor bed and then terminates in a linear array of smaller fibers, each about 500 μm in diameter, with a microfabricated mirror to bend the light 90 degrees along the surface of the sensor. Other configurations of size and angle are of course possible. For example, in certain embodiments, best shown in FIG. 14D, a linear array (not bending 90 degrees) is used. This approach is useful for the "sides" of an imaging probe.

In exemplary embodiments, such as those of FIGS. 14A-14D, the system comprises a multi-fiber core. In these embodiments, the multi-fiber core comprises 12 fibers packed together, and coupled to an LED (not shown). Other numbers of fibers and remote light sources are of course possible. In these embodiments, the light from the remote light source is guided down each of the individual fibers of the fiber optic core to the terminal end, wherein the individual fibers are aligned to form a linear array. To bend the light at the terminal end (90 degrees, for example) the ends of the fibers are cut to a specified bevel (which is 45 degrees in the depicted example) and in certain embodiments can be coated with a mirrored surface, such as a microfabricated mirror. In certain embodiments, the optical fiber can be custom manufactured for this application by, for example, Doric Lenses. As shown in FIGS. 14A and 15A, exemplary embodiments of the system also comprise a transmission cable 136 designed to convey the image signal received by the imager out of the probe and to a remote visualization or processing device (not shown).

In these embodiments, after the light has reached the terminal end of the light guide 110, the light is then transmitted down a waveguide 116, such as the waveguide implementations depicted in FIG. 2D. In certain embodiments, the waveguide 116 may comprise a transparent material that has a higher index of refraction than air, and similar to the material in the fiber optic cable. By way of example, the higher refraction material can be similar to glass. Certain characteristic materials have minimal autofluorescence and minimal absorption in the optical region. Quartz is one such material, though others are possible. As will be described in further detail with respect to FIG. 16, the waveguide allows the light being directed into the waveguide from the light guide to pass through the bottom portion of the waveguide (the portion closest to the tumor bed) toward the tumor bed, while helping to prevent light from being directed upward toward the imager.

In certain embodiments, the light transmitting core 132 and the optical waveguide 116 are coupled together with an optical epoxy. This optical epoxy can be utilized to bond the terminal end of the fiber optic cable(s) to the edge of the waveguide. In these embodiments, the optical epoxy should have an index of refraction similar to the waveguide and fiber optic cable(s). In certain embodiments, the waveguide further comprises at least one insulated wrapping 110A.

Figure 16A:
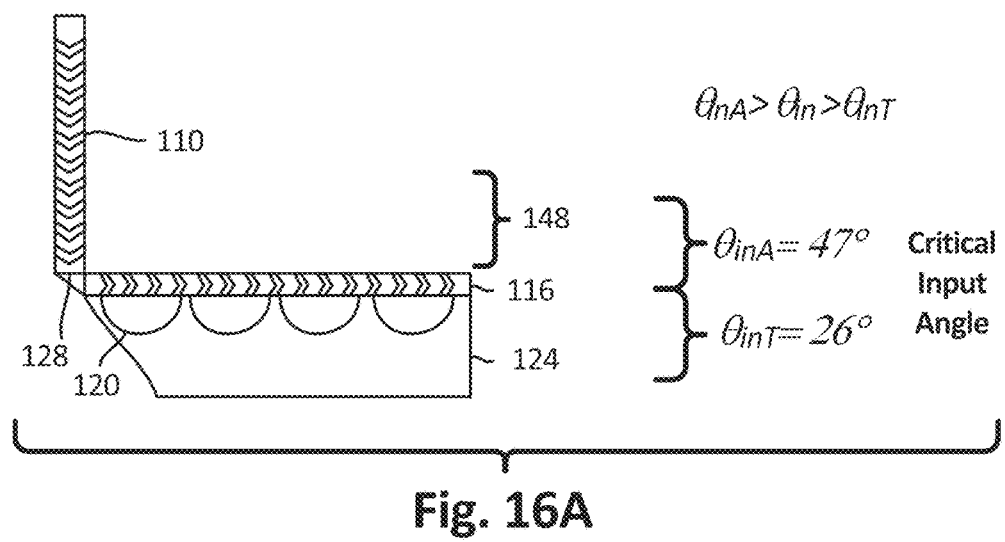
FIG. 16A depicts a side view of the travel of the light down the waveguide, according to one implementation.
Figure 16B:
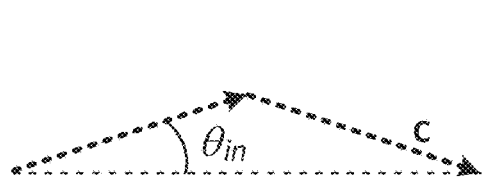
FIG. 16B depicts refraction angles of light at the tumor bed, according to certain implementations.
Figure 16C:
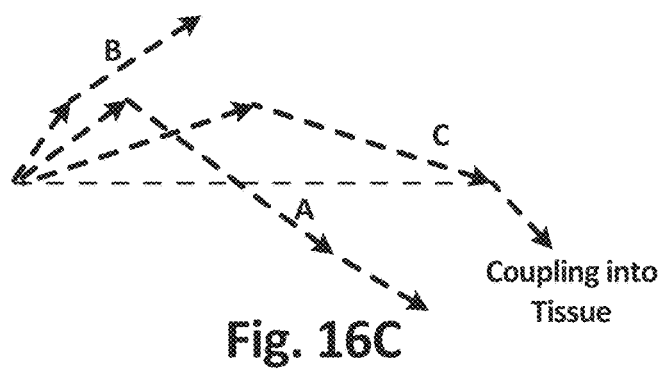
FIG. 16C depicts further refraction angles of light at the tumor bed, according to certain implementations.

FIGS. 16A-16C depict another principle aspect of the system, which is efficiently directing the filtered light from the waveguide 116 to the tumor bed surface 124 and concentrating it there by preventing it from escaping by way of an "air trap" created by differing indices of refraction. By way of example, FIG. 16A depicts the travel of the light down the waveguide 116 and illumination of the tumor bed 124. In these embodiments, the system utilizes the tissue of the body to direct, or "leak" light from the waveguide to the tumor bed and prevent, or "trap" it from directing upward toward the imager.

In practice, light will travel down the waveguide and be "trapped" inside the waveguide by the total internal reflection, as described further herein. Opposite the tumor bed from the waveguide (defined as the space between the imager and the waveguide) the system utilizes material with the lowest possible index of refraction, such that it is transparent, for example air 148. This is frequently known as an "air gap," though other materials, such as low-refraction polymers are possible. For example, if the index of the air gap is n=1, the waveguide is comprised of quartz (n=1.48), and the tissue/fluid of the tumor bed has an index of n=1.33, the light is preferentially trapped in the tissue/fluid and waveguide by this differential in index.

This air (or other lower-refraction material) "gap" serves to "trap" the light in the waveguide and prevents the light from "escaping" upward toward the imager 102. On the opposite (tumor bed-facing) side, the index of refraction of the tissue, saline, and/or blood will more closely match the index of refraction of the waveguide, allowing light to escape. FIG. 3C illustrates this phenomenon. Light is directed into the waveguide at $\Theta_{in}$, where $\Theta_{in}$ is sufficiently large to couple into tissue (line A in FIG. 16C), sufficiently small enough not to pass directly to the imager (line B in FIG. 16C). If $\Theta_{in}$ is too small, then it will not couple into the tissue (line C in FIG. 16B). By way of example, an exemplary calculation is shown for an air gap, quartz waveguide, and saline/tissue interface. In still another embodiment, a microfabricated grating or roughing of the surface is provided to allow light to escape the waveguide on that side. In exemplary implementations, a higher barrier created by the interface between the differing indices of refraction is preferable, though not required. In alternate embodiments, the optical waveguide can comprise high index material as another means of increasing the differentiation in index of refraction, although the optimum is an index of refraction closest to that of tissue and/or blood. In other embodiments the air-gap is eliminated and waveguide abuts the optical filter 114. The optical filter 114 must then reject the excitation light adequately, allowing on the fluorescently emitted light to pass through. In one implementation this rejection of excitation light is 10^5 stronger than blocking of the fluorescently emitted light, and is achieved with an interference filter 114.

To achieve angles depicted in FIG. 16B multiple approaches are possible. In certain embodiments, fibers are angled with respect to the waveguide, for example fibers may be perpendicular or angled at 30 degrees with respect to the waveguide. The angle can be adjusted by having a mirror that is a different angle than 45 degrees.

One embodiment of the system comprises a hexagonally packed pixel array, comprising a plurality of individual photodiodes and pixel circuitry.

One embodiment of the system comprises an alternative hexagonally packed pixel array for μLens array accordingly to further embodiments and the corresponding microlens array 120. One skilled in the art will appreciate that other pixel configurations are possible.

There is an alternative chip layout according to certain embodiments. In these embodiments, the chip comprises a pixel array, and further comprises a clock divider and bond pads.

In exemplary embodiments, the resulting images can be displayed to the user by way of a commercially-available monitor. In exemplary implementations, an analog-to-digital converter with data processed into an image by MATLAB software on a desktop computer.

In another implementation, the conventional optical filters, whose performance is highly dependent on the incident angle of light—which in turn requires optics to ensure precise optical alignment of the filter 114 with incoming light—is eliminated by using a filter 114 that operates by absorbing certain wavelengths of light while letter other wavelengths pass through. Here, the filter 114 absorbs the incident light, but allows the fluorescently emitted light to pass through. Absorption-based filters eliminate the need for precision, multi-layer depositions while being angle insensitive. The choice of material, and thickness, depends on the intrinsic bandgap, as well as the steepness of the fall-off. Many organic fluorophores are optimally excited at 30-50 nanometers below their maximal emission, however they often have broad absorption spectra, albeit at lower fluorescence efficiency. Given this, it is reasonable to assume that with a 100 nm difference between excitation and emission, only a 50% reduction in emitted photons. Indocyanine green is a commonly used, FDA-approved, fluorophore with such properties. Other clinically utilized fluorophores included IR700DX (XX) and IR800CW[24,25]. Given that the absorption cross section of fluorophores is roughly ~$10^{-16}$ $cm^2$, and the average protein (with a single fluorophore attached) has a diameter of 3-7 nm (7-50×$10^{-14}$ $cm^2$) requiring a rejection of roughly 3-4 orders of magnitude. We select amorphous silicon with a bandgap of ~1.4 eV (880 nm), and can range from 1.4-2 eV (610 nm) depending on deposition parameters. Since amorphous silicon (a-Si) is transparent above the bandgap, this creates a long-pass filter ideally suited to standard optical fluorophores with emission wavelengths from 500-900 nm. The intrinsic photoresponsivity of silicon-based photodiodes, with poor responsivity above 900 nm, effectively acts as a short-pass filter, and the combination results in a band-pass filter.

Figure 17A:
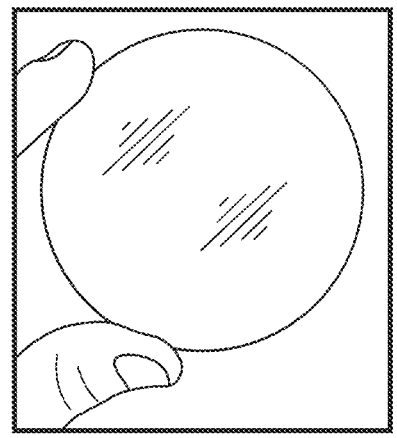
FIG. 17A is a top view of a filter, according to one implementation.
Figure 17B:
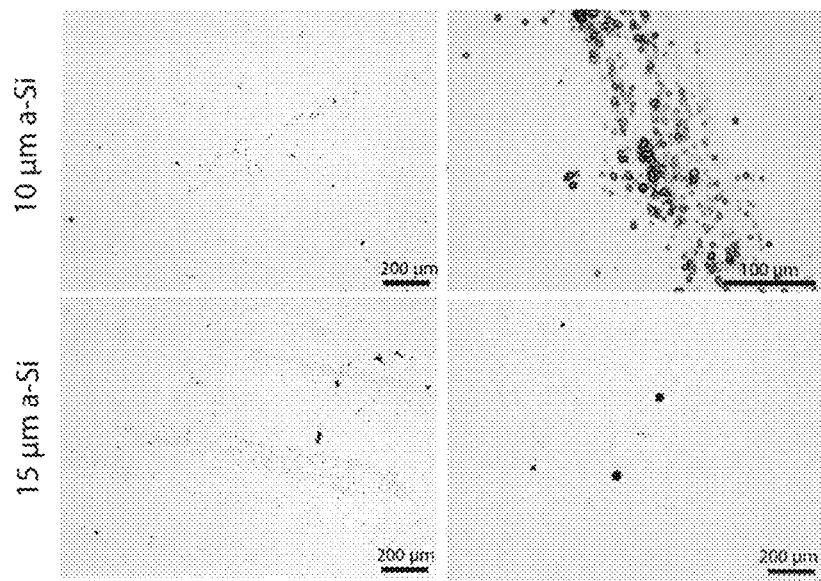
FIG. 17B is an image of fluorescent cells with amorphous silicon filters of varying thickness.

To demonstrate this concept, amorphous silicon filters 114 were fabricated at the University of Washington, Nanofabrication Facility. 525 um fused silica wafers, acting as host substrates, and placed into a SPTS APM PECVD, deposited a-Si at 1 Torr and 350 degrees C., resulting in 5, 10 and 15 um thicknesses. Material stress measurements (supplementary materials) were obtained after each deposition. Wafers were diced into 3×5 mm dilets, and epoxied onto a CMOS imager with ASG using EpoTek clearly epoxy. Hillock density increased with increasing film thickness, but remained sparse enough to obtain a flat, uninterrupted dilet for imaging, as is shown in FIGS. 17A-17B. which demonstrates that hillock density increases as a-Si film thickness increases. However, areas of relatively uninterrupted amorphous silicon area available between regions of hillocks, and these areas are selected to be cut for filters 114.

Figure 18A:
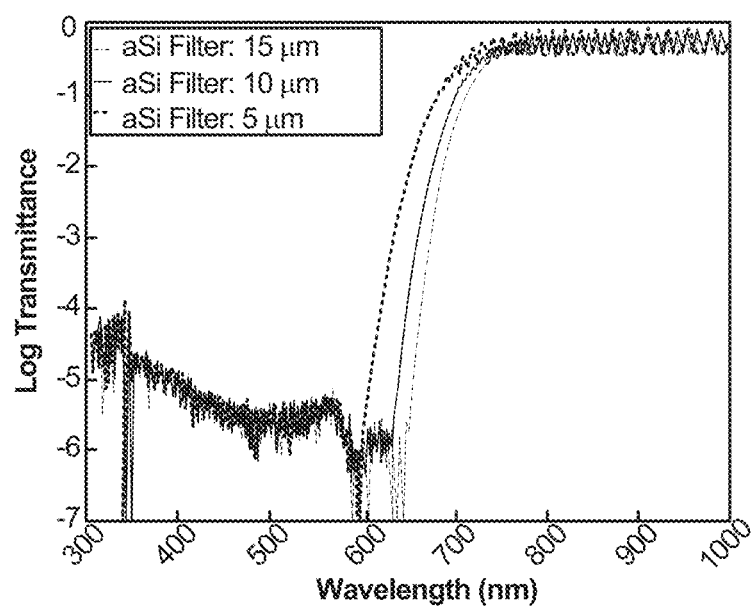
FIG. 18A is a graph showing the Log transmission spectra vs. wavelength with spectrophotometer for films of thicknesses of 5 μm, 10 μm, 15 μm.
Figure 18B:
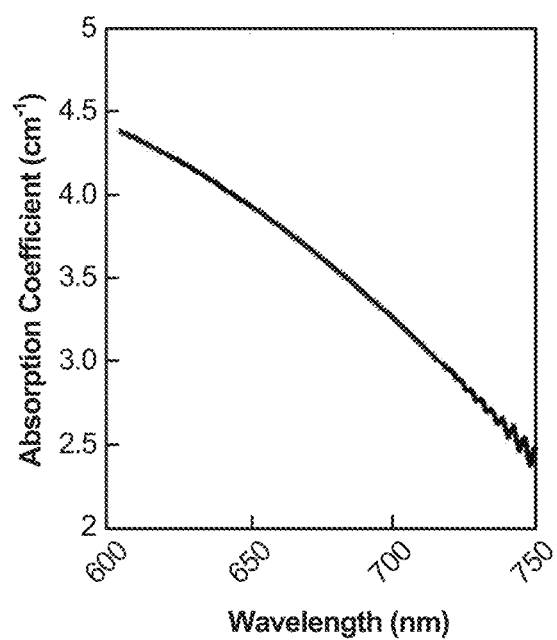
FIG. 18B is a graph showing the absorption coefficient vs. wavelength combined transmission curve between 5 and 15 μm.
Figure 18C:
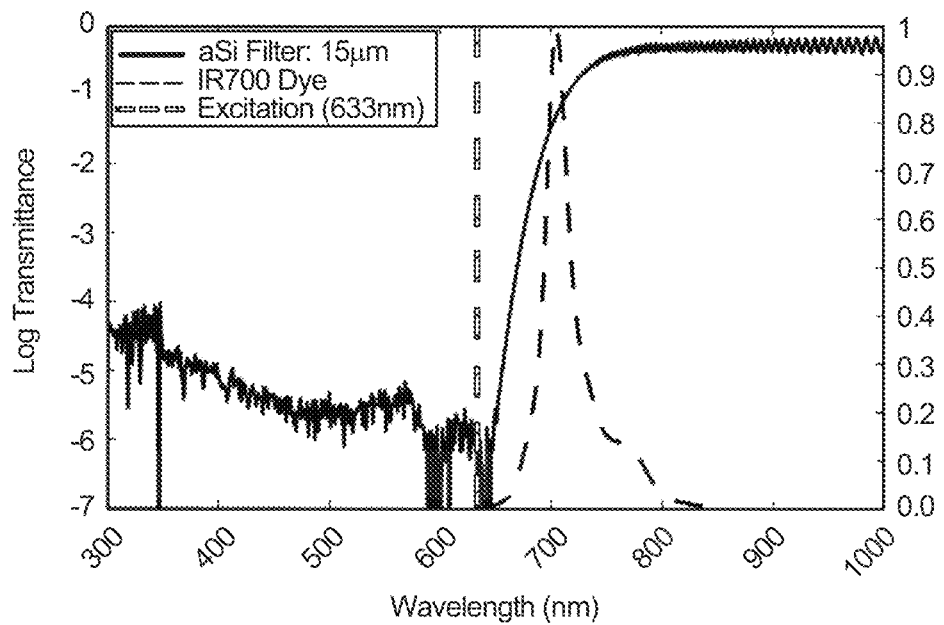
FIG. 18C is a graph showing the Log transmission spectra vs. wavelength for a 15 μm filter with IR700 dye and an excitation of 633 nm.
Figure 18D:
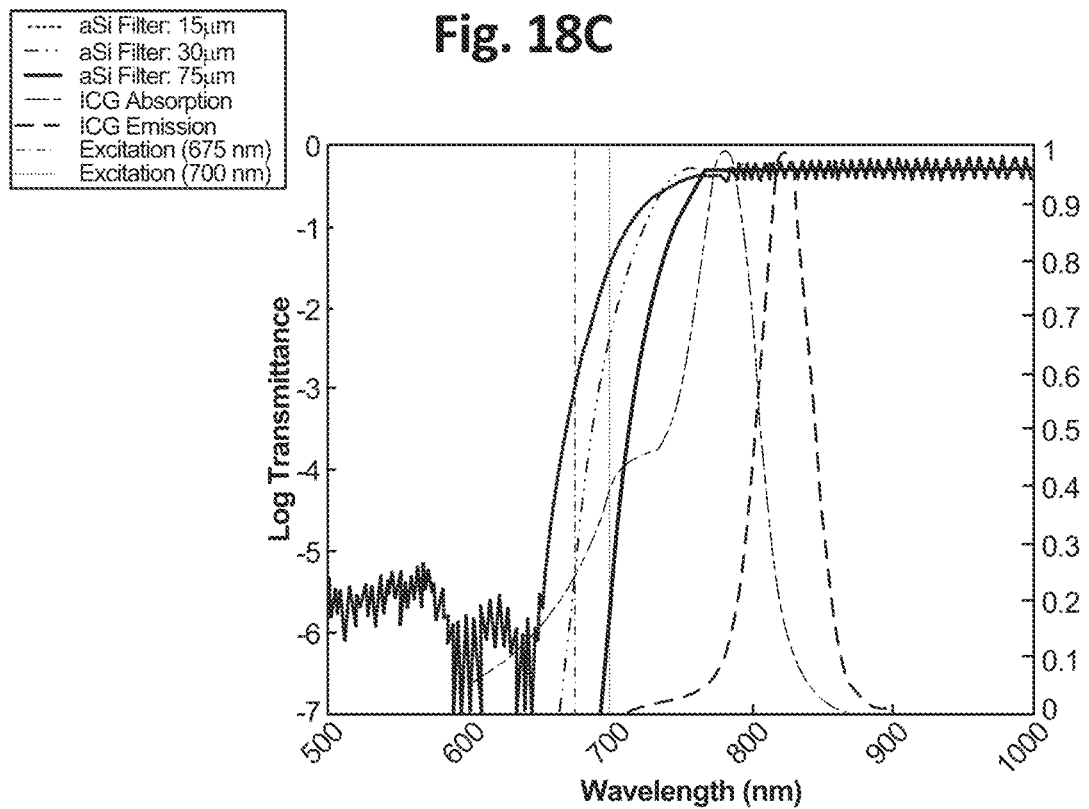
FIG. 18D is a graph showing the Log transmission spectra vs. wavelength for 15 μm, 30 μm and 75 μm film thickness overlays with various absorption and emission curves for commonly used clinical fluorophores, demonstrating applicability.

Transmission spectra are shown in FIGS. 18A-B. FIG. 18A-B show transmission spectra for films of thickness 5, 10, 15 μm, taken on a Perkins elmer lambda 850 UV-Vis Spectrometer. In FIG. 18A Transmission spectra are taken with spectrophotometer. Thicker films push the long-pass transmission wavelength towards 800 nm, with a sharper cutoff. At 15 um thickness, over five orders of magnitude of optical rejection is achieved when illuminating at 650 and imaging at 750 nm. In FIG. 18B combining the transmission curves between 5 and 15 um allows determination of the absorption coefficient as a function of wavelength.

FIG. 18B displays the extracted absorption coefficient of the deposited amorphous silicon or all three filter 114s. (FIG. 17A images of the filter 114, illustration transparency to red light and hillock formation). FIG. 26C-D overlays 15 um, 30 and 75 um film thickness with various absorption and emission curves for commonly used clinical fluorophores, demonstrating applicability. The transmission is 60% as predicted from the boundary condition of a change in index of refraction from amorphous silicon ($n_{aSi}$=4.3) to air ($n_{air}$=1). The ripple on the pass-band of the transmission spectra is due to interference fringes within the amorphous silicon layer[40]. The absorption spectra is fit to the expression: $T(\lambda)=\exp(-x*\alpha(\lambda))$, where T is the transmission, x is the amorphous silicon layer thickness, and a is the wavelength dependent absorption coefficient.

To demonstrate angle insensitivity, the aSi-CMOS Imager, as well as the imager 102 covered in two thin-film interference filters 114 (Chroma) was illuminated with 633 nm light at incident angles ranging 0 to 90 degrees to the perpendicular of the chip, as shown in FIG. 27. In FIG. 27, a plot of normalized intensity as a function of incident angle using 633 nm light. A small fraction of light penetrates the filter 114 providing the imager 102 signal. Two different commercially produced interference filters 114, fabricated on a 500 um quartz substrate for structural support are affixed to the imager surface, and illuminated at increasing angles from the perpendicular. The conventional interference filter 114 performance degrades linearly with increasing incident angle, until 30 degrees when exponentially more light penetrates the filter 114 with increasing angle. The amorphous silicon filter 114, however is angle insensitive, and the decreasing intensity with increasing angle is a function of the angle selective gratings on chip.

We have previously shown that angle-selective gratings (ASG) light incident at oblique angles. The amorphous silicon filter 114 displays the expected angle-response, with decreasing intensity with increasing incident angle from the perpendicular. This is primarily due to the angle selective gratings, and indicate no significantly increased optical bleed through from the amorphous silicon filter 114, even for highly oblique incident angles of light. However, both conventional interference filters 114 show a near exponential response past ~30 degrees, saturating the photodetector 102.

To demonstrate applicability to cell imaging, breast cancer patient tumor tissue samples were imaged ex vivo. As shown in FIGS. 20A-20B, a clear border was imaged in only 60 ms; averaging further improves image quality. To demonstrate applicability to the tissue architecture associated with invasive tumors in vivo, HER2+ human breast tumor tissue is imaged. Corresponding images from the microscope and chip are shown with only a 75 ms integration time, clearly visualizing the HER2+ tumor margin as identified by immunofluorescence and H&E-staining. In FIG. 20A, fluorescence image of a human breast tissue sample mounted on a glass slide stained with anti-HER2 antibody and a quantum-dot (705 nm) secondary antibody, taken at 5 s integration. Tumor infiltrating the normal breast tissue is seen as the brighter areas on the background from nonspecific binding. The area labeled Slide is the background from the glass slide, corresponding to filter 114 bleed through and nonspecific binding to the slide. In FIG. 20B, the same image taken with an image sensor was taken with a 15 um aSi filter 114 attached. The areas of tumor can be clearly seen over the normal tissue background.

Despite recent advances in fluorescently-labeled targeted molecular agents for intraoperative guidance, the inability to miniaturize fluorescent imagers to the scale where they can be inserted within the tumor cavity, thoroughly imaging the entire surface with high sensitivity, results in tumor cells left behind despite the ability these markers to identify single tumor cells. Here we introduce a fluorescence contact imager with high-rejection angle insensitive filter 114 using amorphous silicon that dispenses with the need for traditional focusing optics. This is made possible by incorporation of a high-rejection angle insensitive filter 114, removing the requirement for tightly controlled incident light necessitated by a conventional optical filter 114, which require optics to guide light, instead relying on the intrinsic absorption properties of amorphous silicon.

Multiple efforts have been made to miniaturize conventional microscopes, however these still remain several centimeters in length. Scaling optics encounters fundamental challenges as fabricating optics at micro-scales becomes increasing difficult and introduces aberration due to imperfections. Attempts to decouple the optics needed for fluorescence imaging from the light gathering to minimize the imager footprint within the patient have centered on fiber optics. However optical fibers face a fundamental tradeoff between flexibility (e.g. bending radius) and imaging area, and cannot efficiently image a small (1-3 cm diameter) tumor cavity due to the large surface area. Contact imagers solve this problem as they rely on proximity to the sample for the requisite spatial resolution (~100 um for approximately 200 cells) and therefore can dispense with optics. Contact fluorescence imagers have relied on direct en face illumination to ensure optimal performance by the optical filter 114s; however this is not possible for intraoperative imaging where oblique illumination is required. Consequently, fluorescence contact imagers to date have largely been used for assays in which the sample is directly printed on the imager and illuminated directly.

To extend use in vivo we require an angle insensitive optical filter 114, which we achieve using the absorptive properties of amorphous silicon demonstrated here. While a-Si is ideal for fluorophores that emit close to 700 nm, including Alexa Fluor 700 and, IR700DX which has been used in multiple cancer imaging studies in both animals and patients, other materials compatible with microfabricated deposition are also possible.

Angle-insensitive filters 114 improve contact-imager performance and simplify fabrication: leveraging the intrinsic absorptive properties of amorphous silicon (a-Si), with a band gap of 1.8 eV, we create an angle insensitive long-pass filter 114 above 700 nm-800 nm (relative to crystalline silicon with a bandgap of 1.1 eV or 1100 nm). A single thin-film layer achieves over 5 orders of magnitude of excitation light rejection, enabling direct on-chip fabrication.

Certain embodiments have implemented interference-based filters 114 (~10 μm fabricated on a 500 μm fused silica substrate serving as the waveguide), commercially fabricated through our industry collaborator Chroma. By epoxying these filters 114 directly on-chip we demonstrate fluorescence detection of labeled cancer cell clusters. These filters 114 are made to any optical specification found in commercial microscopes, extending applicability to a wide range of fluorophores.

Fabricated a-Si filters 114 at 5, 10 and 15 μm thickness (FIG. 26) demonstrating increased rejection and sharper cutoff with increasing film-thickness. Overlaid is the measured fluorescence spectra of IR700DX excited at 633 nm; excitation light is reduced by 6 orders of magnitude while the majority of emission light (>700 nm) is transmitted, making this an appropriate filter 114 for IR700DX. FIGS. 20A-B shows the results of our sensor imaging tissue with integrated a-Si filter 114.

15 μm a-Si films can be patterned directly on-chip, reducing optical bleed an additional 2-orders of magnitude, and increase illumination intensity by 10×. It is possible to verify the SNR increase of 16 dB by measuring the SNR increase of various cell-cluster sizes (range 1-10,000).

Increased a-Si film thickness pushes the long-pass cutoff towards 800 nm for ICG imaging. By measuring the absorption coefficient versus wavelength from our existing filters 114, predicted transmission spectra are plotted in FIG. 18D making a 30-75 μm a-Si film ideal for ICG imaging. The broad absorption spectra of ICG, allows excitation at 675-700 nm, capturing the entire emission spectra.

While the filter 114 is demonstrated with amorphous silicon, other materials are also included for potential use. A subset of materials are listed below, but other materials with bandgaps in the visible, near infrared or infrared wavelengths are also applicable. Furthermore, we also include versions of these materials where the band gap is altered by adding dopants, or changing the deposition parameters (by varying temperature and pressure of deposition). Additionally, we include thickness above 500 nm to act as optical filter 114s (with no upper limit, limited by only the physical ability to deposit a thick later on a host substrate or directly onto the imager surface). These materials are listed below in Table 1, adapted from Kittel, C., Introduction to Solid State Physics, 6th Ed.

TABLE 1

Materials and band-gaps.

| Material | Bandgap | Wavelength |
| --- | --- | --- |
| Amorphous Silicon (aSi) | 1.7 eV | 730 nm |
| Crystalline Silicon (cSi) | 1.1 eV | 1100 nm |
| Gallium Arsenide (GaAs) | 1.4 eV | 880 nm |
| Indium Phosphate (InP) | 1.3 eV | 950 nm |
| Cadmium Selenium (CdS) | 1.85 eV | 670 nm |

Thicker film layers result in a sharper cutoff, allowing the excitation light to be closer in wavelength to the emission light, often increasing efficiency for fluorophores with small Stokes shift.

Other prior art approaches to filter illumination light from the smaller fluorescent signal dispense with interference structure of conventional filters altogether. Leveraging the small feature sizes and spacing inherent in today's modern IC process, subwavelength metal nanostructures fabricated from the metal interconnects common to all IC processes have been used to achieve both angle sensitivity and angle insensitive color filtering.

Optical filters enable increased illumination increasing signal intensity. Identifying fluorescently labeled cells amidst a background of illumination light $10^5$ times, or greater, in intensity, necessitates an optical filter with high-performance out-of-band rejection to prevent pixel saturation. However, the oblique angles of incidence associated with side-coupled illumination degrade performance of conventional multilayer interference filters, resulting in optical bleed through. Along with dark current, this hinders imager performance by consuming pixel capacity, limiting signal integration. Currently, with interference filters, dark current and optical bleed through each consume ~40% of pixel capacity. This improves filter performance 100× by implementing an angle-insensitive filter, allowing for increased illumination (10×) and reduced background (10×). Reduced optical bleed through allows more signal integration, increasing SNR 6 dB. The increased illumination reduces integration time and effectively eliminates dark current contribution by increasing optical sources of signal and background, far outweighing dark current, increasing SNR by 6 dB. Reduced integration time improves SNR an additional 4 dB through averaging multiple images.

In various implementations, fabricated thin-film interference filters 114 for ICG can be directly patterned onto the CMOS imager. In these implementations, a-Si is patterned at temperatures and pressures compatible with CMOS; however fabrication can be decoupled, with a-Si patterned on thinned quartz wafers. It is possible to pattern thicker layers of a-Si; increased material stress limits silicon substrate thinning to 200-300 μm. At 30 μm thickness, ICG is excited at 675 nm for 20% absorption efficiency, while 700 nm excitation through 75 μm a-Si achieves 40%. Alternate embodiments shift the band-gap (transmission cutoff) for a-Si by varying deposition parameters, customizing this filter 114 for fluorophores with emission ≥700 nm. It is understood that autofluorescence from blood and the tissue contributes background. In certain examples, it is possible to quantify the autofluorescence by introducing a variation on spectral unmixing. Taking advantage of the sharp absorption ($\lambda_{abs}$) and emission peaks of IR700DX when compared to the slowly-varying absorption and emission spectra of autofluorescence, we rapidly alternate illumination at $\lambda_{abs}$, exciting both the fluorophore and the tissue autofluorescence, followed by $\lambda_{abs} - \Delta\lambda$ ($\Delta\lambda = 100$ nm), exciting primarily the tissue autofluorescence, and subtract these two values. In certain applications, it is possible to quantify the SNR improvement, and if >3 dB (as it doubles integration time) incorporate it into the imager.

Although the disclosure has been described with reference to preferred embodiments, persons skilled in the art will recognize that changes may be made in form and detail without departing from the spirit and scope of the disclosed apparatus, systems and methods.

What is claimed is:

1. A system for identifying and removing biological material, comprising:
    a) an imager comprising an imaging surface; wherein the imager comprises:
        i) a plurality of pixels;
        ii) nano-gratings; and
        iii) a filter; and
    b) a visualization system in electrical communication with the imager, wherein the imager has an overall thickness of less than 1 mm.

2. The system of claim 1, further comprising an optical filter.

3. The system of claim 1, wherein the imager is operationally integrated with a surgical tool.

4. The system of claim 3, wherein the surgical tool is a scalpel.

5. The system of claim 3, wherein the imager comprises at least one LED or at least one laser diode light source.

6. A lens-free system for identifying and removing a biological material, comprising:
    a) a fluorescence imager comprising:
        i) a plurality of individual pixels and nano-gratings for angle selective imaging;
        ii) an optical filter; and
        iii) at least one wavelength-specific light source; and
    b) a visualization system in electrical communication with the imager, wherein the fluorescence imager has an overall thickness of less than 1 mm.

7. The system of claim 6, wherein the imager is operationally integrated with a surgical tool.

8. The system of claim 6, wherein the imager is a surgical tool.

9. The system of claim 6, wherein the at least one wavelength-specific light source comprises at least one LED and/or at least one laser diode.

10. The system of claim 6, wherein the optical filter is a single material.

11. The system of claim 6, wherein the optical filter is less than about 100 microns thick.

12. The system of claim 6, wherein the optical filter is less than about 50 microns thick.

13. The system of claim 6, wherein the imager comprises at least one laser diode.

14. The system of claim 6, wherein the optical filter comprises an inorganic material that absorbs illumination light by at least 100× more than emission wavelength.

15. A lens-free system for identifying and removing a biological material, comprising:
    a) a fluorescence imager comprising an imaging surface, the imaging surface comprising:
        i) a plurality of individual pixels and nano-grids for angle selective imaging; and
        ii) an optical filter; and
    b) a visualization system in electrical communication with the imager;
    wherein the entire fluorescence imager has an overall thickness of less than 1 mm.

16. The system of claim 15, wherein the optical filter is an angle-insensitive filter.

17. The system of claim 15, wherein the optical filter comprises an inorganic material that absorbs illumination light by at least OD 2 below emission wavelength.

18. The system of claim 15, wherein the optical filter comprises a semiconductor.

19. The system of claim 18, wherein the semiconductor is selected from the group consisting of amorphous silicon, crystalline silicon, gallium arsenide, indium phosphate and cadmium selenium.

* * * * *

UNITED STATES PATENT AND TRADEMARK OFFICE
CERTIFICATE OF CORRECTION

| | | |
|---|---|---|
| PATENT NO. | : 11,576,580 B2 | Page 1 of 1 |
| APPLICATION NO. | : 16/854463 | |
| DATED | : February 14, 2023 | |
| INVENTOR(S) | : Anwar et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 287 days.

Signed and Sealed this
Twelfth Day of September, 2023

*Katherine Kelly Vidal*

Katherine Kelly Vidal
*Director of the United States Patent and Trademark Office*